US012668766B2

(12) United States Patent
Cirit et al.

(10) Patent No.: US 12,668,766 B2
(45) Date of Patent: Jun. 30, 2026

(54) MICROFLUIDIC SYSTEMS AND SUPPORT MODULE

(71) Applicant: Javelin Biotech, Inc., Woburn, MA (US)

(72) Inventors: Murat Cirit, Cambridge, MA (US); Douglas G. Sabin, Marblehead, MA (US); Peter Conway, Groton, MA (US); Jacob Freake, Somerville, MA (US); Corbin Munn, New York, NY (US); Joseph Von Schoppe, Medford, MA (US); Renee Hester, Boston, MA (US); Emily Geishecker, Burlington, MA (US); Shiny Amala Priya Rajan, Woburn, MA (US); Abraham LeMole, Boston, MA (US)

(73) Assignee: Javelin Biotech, Inc., Woburn, MA (US)

( * ) Notice: Subject to any disclaimer, the term of this patent is extended or adjusted under 35 U.S.C. 154(b) by 794 days.

(21) Appl. No.: 17/891,863

(22) Filed: Aug. 19, 2022

(65) Prior Publication Data

US 2023/0058647 A1     Feb. 23, 2023

Related U.S. Application Data

(60) Provisional application No. 63/235,016, filed on Aug. 19, 2021.

(51) Int. Cl.
*C12M 1/00*          (2006.01)
*C12M 1/26*          (2006.01)
(Continued)

(52) U.S. Cl.
CPC ............ *C12M 23/16* (2013.01); *C12M 23/46* (2013.01); *C12M 29/24* (2013.01); *C12M 33/00* (2013.01);
(Continued)

(58) Field of Classification Search
CPC ....... C12M 23/44; C12M 41/48; C12M 23/16
See application file for complete search history.

(56) References Cited

U.S. PATENT DOCUMENTS 11,773,359 B2 * 10/2023 Ingber .............. B01L 3/502715
                                                            29/428
2002/0146817 A1   10/2002 Cannon et al.
(Continued)

OTHER PUBLICATIONS

International Search Report and Written Opinion in International Appln. No. PCT/US2022/075223, mailed on Dec. 6, 2022, 10 pages.
(Continued)

*Primary Examiner* — Nathan A Bowers
(74) *Attorney, Agent, or Firm* — Fish & Richardson P.C.

(57) ABSTRACT

This disclosure describes hardware for microfluidic chips and an associated support module for facilitating operation of one or more microfluidic chips. The microfluidic chips described herein are designed for supporting multiple different tissue types, including kidney tissue, liver tissue, adipose cells, and so forth. Chip geometry facilities fluid flow through one or more channels of the chip with a particular flow rate. For example, shear forces are reduced where needed to ensure proper flow rate of fluid in the channels. The chamber geometry and the geometry of the channels ensures that a desired amount of oxygen is delivered to sample cells or tissues in a controlled manner.

30 Claims, 66 Drawing Sheets

(51) Int. Cl.

| | | |
|---|---|---|
| *C12M 1/34* | (2006.01) | |
| *C12M 1/36* | (2006.01) | |
| *C12M 3/00* | (2006.01) | |
| *C12M 3/06* | (2006.01) | |

(52) U.S. Cl.

CPC ............ *C12M 41/26* (2013.01); *C12M 41/34* (2013.01); *C12M 41/44* (2013.01); *C12M 41/48* (2013.01)

(56) References Cited

U.S. PATENT DOCUMENTS

| | | | |
|---|---|---|---|
| 2007/0154895 A1 | 7/2007 | Spaid et al. | |
| 2008/0064088 A1 | 3/2008 | Shuler et al. | |
| 2008/0248552 A1* | 10/2008 | Castillo Fernandez | ...................... C12M 23/34 435/243 |
| 2010/0216218 A1* | 8/2010 | Huang | ................... C12M 27/02 435/257.1 |
| 2011/0217690 A1* | 9/2011 | Niazi | ..................... C12M 23/58 435/3 |
| 2014/0030752 A1* | 1/2014 | Cuiffi | ..................... C12M 23/12 435/375 |
| 2014/0349392 A1* | 11/2014 | Nelissen | ................ C12M 25/06 435/325 |
| 2018/0051243 A1* | 2/2018 | Hogan | ................... C12M 41/46 |
| 2018/0080570 A1* | 3/2018 | Block, III | ............. C12M 23/16 |
| 2019/0100786 A1* | 4/2019 | Kwon | .................... C12M 25/14 |
| 2019/0330584 A1 | 10/2019 | Rathbone et al. | |
| 2019/0376014 A1* | 12/2019 | Efimov | .................... C12N 9/22 |
| 2021/0156846 A1 | 5/2021 | Cirit et al. | |
| 2021/0189315 A1* | 6/2021 | Zhou | ..................... C12M 23/58 |
| 2021/0198607 A1 | 7/2021 | Wikswo et al. | |
| 2021/0238521 A1* | 8/2021 | Yamanaka | ............. C12M 23/12 |
| 2023/0220323 A1* | 7/2023 | Hashimoto | ........... C12M 23/06 435/289.1 |

OTHER PUBLICATIONS

Kietzmann, "Metabolic zonation of the liver: The oxygen gradient revisited," Redox Biology, Jan. 12, 2017, 11:622-630.

International Preliminary Report on Patentability in International Appln. No. PCT/US2022/075223, mailed on Feb. 29, 2024, 9 pages.

* cited by examiner

Fig. 10A

Air inlet

Vent

Air at desired composition from gas supply

906

Culture media in reox. chamber

Liquid flow in
(from flow sensor)

900

Air

906

908

Water

Liquid flow out
(to pump)

1012

Air

Liquid

1010

906

908

Tl

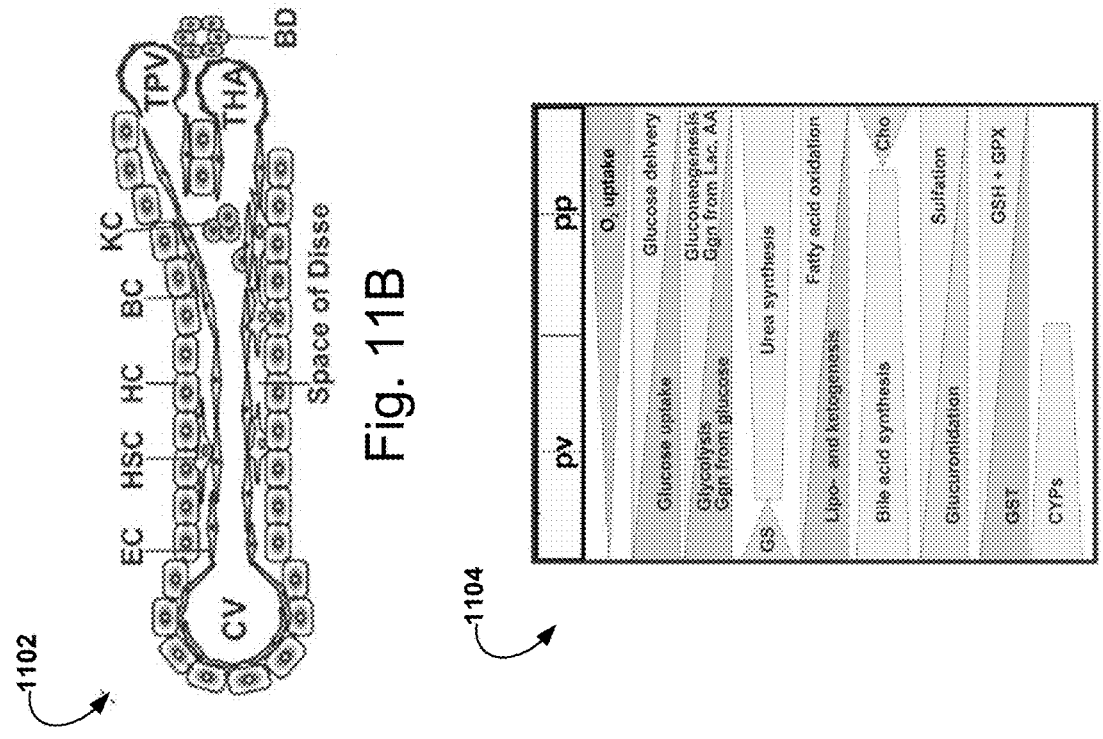
Fig. 11B
Fig. 11C
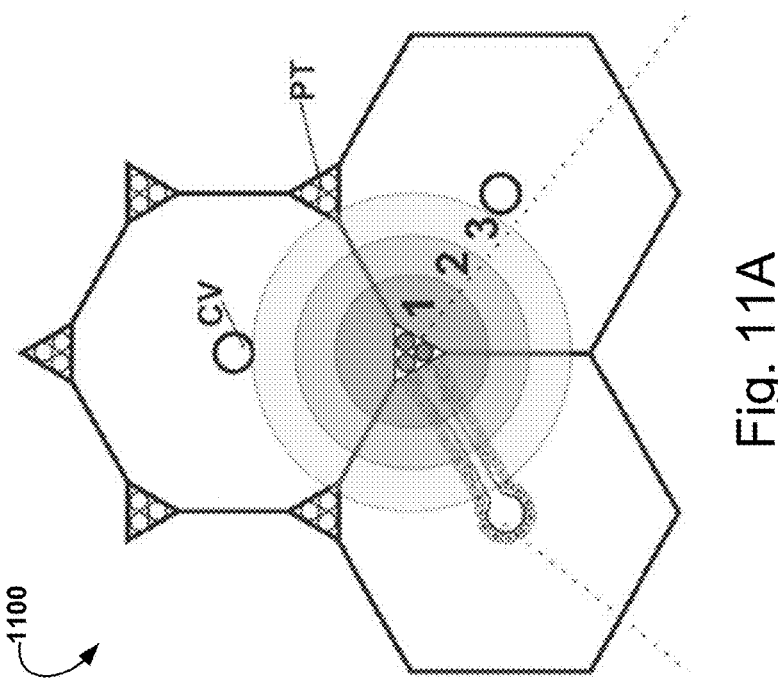
Fig. 11A

1200

1218

1210

1230

1204

1220

1222

1300

1304

1302

1300

1304

1302

3702

3702

MICROFLUIDIC SYSTEMS AND SUPPORT MODULE

CLAIM OF PRIORITY

This application claims priority under 35 U.S.C. § 119(e) to U.S. Patent Application Ser. No. 63/235,016, filed on Aug. 19, 2021, the entire contents of which are hereby incorporated by reference.

FIELD OF THE INVENTION

This disclosure generally relates to microphysiological systems (MPSs). More specifically, this disclosure relates to hardware systems to support and control operations of one or more MPSs either individually or in different combinations with one another. This disclosure relates to hardware designs of a plurality of MPSs for operation either individually or in combination with one another and the hardware support system.

BACKGROUND

A microphysiological system (MPS) (also called a microfluidic chip) includes an interconnected set of two- or three-dimensional cellular constructs that are frequently referred to as organs-on-chips, tissue chips, or in vitro organ constructs. The constructs are typically made with immortalized cell lines, primary cells from animals or humans, or organ-specific cells derived from naïve cells, human embryonic stem cells, and induced pluripotent stem cells (iPSCs). Individually, each construct can be designed to recapitulate the structure and function of a human organ or organ region, paying particular attention to the cellular microenvironment and cellular heterogeneity. When coupled together to create an MPS, these constructs offer the possibility of providing, in vitro, an unprecedented physiological accuracy for the study of cell-cell, drug-cell, drug-drug, and organ-drug interactions, if drug delivery can be properly modeled.

SUMMARY

This disclosure describes hardware for microfluidic systems (also called microfluidic chips or simply chips in this disclosure) and an associated support module for facilitating operation of one or more microfluidic chips. The microfluidic chips include hardware that houses tissue constructs to provide biomimetic cues for long-term culture and physiologically-relevant tissue functions. The microfluidic chips described herein are designed for supporting multiple different tissue types, including lung tissue, kidney tissue, liver tissue, and so forth. Chip geometry facilities fluid flow through one or more channels of the chip with a particular flow rate. For example, shear forces are reduced where needed to ensure proper flow rate of fluid in the channels. The chamber geometry and the geometry of the channels ensures that a desired amount of oxygen is delivered to sample cells or tissues in a controlled manner. Additionally, the geometry of the chambers and channels in the microfluidic chips enables precise control of an amount of a drug or, any other substance, to be delivered to a tissue sample as desired for performing experiments.

The hardware support module (also called a controller) includes controls for controlling operation of a microfluidic chip that is interfaced with the support module. For example, the support module includes a hardware interface for inputting commands for circulation rates, concentration values, sampling rate and timing, pump and valve operation, and so forth.

The microfluidic chips and hardware support module enable one or more of the following technical advantages.

The microfluidic chip enables long-term physiologically relevant tissue culture of healthy and disease tissues. In diseased tissues, human disease hallmarks can be recapitulated during a chip experiment. The tissue then can be used for-omics analysis to understand disease mechanisms and patient variability. In some implementations, in vitro to in vivo translation is used for translation of pharmacodynamics models. The use of -omics analysis provides greater molecular insight relative to standard in vitro assays. The MPSs described herein utilize metabolomics and transcriptomics to classify/stage various diseases (e.g., non-alcoholic fatty liver disease, or NAFLD, Parkinson's disease, and so forth) in vitro and translate these findings to the clinical applications. MPS and -omics technologies are integrated to accelerate metabolite-based biomarker discovery for a noninvasive disease diagnostics using systems biology analysis and a multi-donor multicellular MPSs, such as liver MPS, kidney MPS, brain MPSs, and so forth.

An MPS is relatively low-cost in comparison with animal in vivo studies, can provide high throughput analysis not possible with animal in vivo studies, and provides more relevant results than animal in vivo studies. Specifically, the microfluidic chips described herein enable reconstruction of multi-cellular cytoarchitectures of human tissues and pathophysiologies in a high-content or high-throughput manner. Additionally, subpopulations are established with the microfluidic chips described herein to discover drugs for various subpopulation (e.g., a stratified medicine approach), potentially overcoming the bottleneck of evaluating population responses at preclinical stage (e.g., prior to a phase II or a phase III clinical trial stage).

The MPS integrates several workflows to identify disease modifying biomarkers and/or targets and combination therapies in various sub-populations. The MPS recapitulates disease phenotypes and disease progression using tissue engineered, human-based MPSs for a given tissue type. The emerging multi-scale data (phenotypic and multi-omics) are processed with corresponding computational models to identify molecular dysfunctions for various disease phenotypes and to rank order the potential therapeutic targets associated with disease phenotypes. The disease-modifying potential of the rank-ordered targets is experimentally evaluated using functional genomics approaches enabled by the MPSs, such as CRISPR gene editing. The MPSs enable mechanisms of action-based drug discovery but also stratified medicine at the preclinical discovery stage.

The systems described in this document are configured for precise emulation of human physiological systems. For example, each MPS design is particular to a corresponding physiological system in humans. The geometry and orientation of the microfluidic chambers on each MPS are configured to emulate fluid flow rates and oxygenation rates (among other parameters) that occur in the human body for a given tissue type hosted by the respective MPS. For example, an MPS that hosts human liver tissue is configured to precisely emulate the oxygenation rate for liver tissue in the human body. A geometry (e.g., length, width, depth, etc.) of the chamber hosting the liver tissue is configured so that the liver tissue experiences an identical or nearly-identical environment as would occur in the human body. The tissue receives a precise amount of oxygen at a precise rate, so that a realistic oxygenation gradient is achieved within the tissue.

The exact or near-exact replication of environmental conditions in the human body for tissues hosted in the MPSs is called emulation (or high-fidelity emulation) of the human physiology.

Each MPS is configured to emulate conditions differently depending on which tissue is hosted by that respective MPS. For example, liver cells may experience a first oxygenation rate for a first MPS. In a second, different MPS, muscle tissue experiences a second, different oxygenation rate. Controlling the oxygenation rate, for example, is achieved by altering the geometry of the cell chamber hosting the tissue, adjusting fluid flow rate through the system, and so forth, adjusting a configuration of an associated oxygenation chamber, and so forth as described in greater detail herein.

The MPSs can be formed from a thermoplastic. In some implementations, the thermoplastic includes cyclic olefin copolymer (COC)-based thermoplastic. In some implementations, the thermoplastic includes polycarbonate (PC)-based thermoplastic. At least two layers of the thermoplastic material are heat bonded together, forming the fluid passageways and chambers of the recirculation loop.

Construction from the thermoplastic, as opposed to a polydimethylsiloxane (PDMS)-based plastic, provides several advantages. Thermoplastic materials can be laminated to form channel and chambers that do not absorb drugs. The use of a hard plastic provides mechanical support for pumps and sensors to be placed on the microfluidic chips. The pumps can recirculate the media to emulate, with high fidelity, blood recirculation in a human body. The high-fidelity emulation improves physiological relevance of measurements related to hosted tissues. The emulation enables drug testing by increasing a retention time of the drugs with respect to flow-through systems. The thermoplastic material enables the MPS to be formed from two halves of thermoplastic that are mechanically coupled together (e.g. with screws). Construction of the entire fluid loop from the thermoplastic, as opposed to only a portion of the fluid loop such as the cell chamber, enables recirculation of fluid through a fluid loop that includes the hosted tissue culture. Recirculation of the fluid through the fluid loop enables high fidelity emulation of human physiology. Fluid can be pumped through or across the human tissue to a re-oxygenation chamber that adds a precise amount of oxygen to the fluid. The fluid is then re-pumped through the cell chamber. The closed loop configuration enables more accurate testing of drug absorption in the cell tissue in comparison with open loop configurations in which fluid is pumped across a cell chamber once. The closed fluid loop enables extended emulation of human physiology for a tissue sample. The closed fluid loop can be automatically sampled at various points in time over a course of hours, days, weeks, months, and so forth.

The thermoplastic construction of the fluid loop enables recirculation of the fluid in a closed fluid loop without drug absorption into the thermoplastic. For example, PDMS can absorb up to 100% of drugs (such as lipophilic drugs) in the fluid loop if the microfluidic chip is constructed from PDMS when the fluid is pumped through the cell chamber. In PDMS flow-through microfluidic chips, only a small fraction of pharmaceutical drugs can be tested. In contrast, the thermoplastic material of the microfluidic chips described herein enables testing of a wider variety of drugs with higher precision relative to PDMS-based MPSs. Because drug absorption is limited, the thermoplastic material of the MPS enables a recirculating flow fluid loop at up to relatively fast rates (e.g., several mL/hour), mimicking a human physiology and enabling accurate emulation of drug absorption in the human body. Recirculation of the fluid media extends the duration of drug-tissue exposure (e.g., a five-day or more incubation without a media change).

The microfluidic chips described herein are configured for a reduced shear on cells of the tissue in the fluid loop, even at relatively fast fluid flow rates in the fluid loop. Flow rate of fluid through the cell chamber and the shear stress on the cells in that chamber are directly proportional to one another. A lower shear improves testing outcomes and destroys fewer cells in the tissue. The microfluidic chips described in this specification enable high flow rates (e.g., several ml/hour) while shear on the cells remains below a threshold shear stress value on the cells. Relative to PDMS flow-through microfluidic chips, the microfluidic chips described herein have far faster fluid flow rates (e.g., 100 times faster) while mainlining low shear stresses on the cells. This enables the cells to receive enough oxygen in the microfluidic chip environment and maintain viability in the low-shear stress environment. Generally, the cell chamber constructed from the thermoplastic is shaped to enable a required oxygen concentration (or oxygen concentration gradient) within the tissue in the cell chamber while maintaining low shear stress levels. The thermoplastic does not need to be oxygen-permeable. The tissue in the fluid loop is not oxygen depleted because the geometry of the oxygenation chamber enables the re-oxygenation chamber to supply a required amount of oxygen to the cell chamber and the hosted tissue for absorption by the tissue. In an example, a waterfall shape configuration for the cell chamber minimizes shear at high flow rates, enabling a higher oxygen absorption.

Relative to PDMS, thermoplastic provides advantages for manufacturing the MPS devices. For example, thermoplastic is generally less expensive (10% of the cost of PDMS). The MPS can be formed from injection molding, enabling scalability of manufacture.

The one or more advantages described can be enabled by one or more aspects or embodiments of the platform.

In a general aspect, a microfluidic chip includes a pump configured to pump a fluid medium through a fluid circuit; a cell chamber in the fluid circuit, the cell chamber supporting a plurality cells, the cell chamber configured to receive the fluid medium including oxygen for exposing the plurality of cells to the fluid medium including the oxygen; and a re-oxygenation chamber configured to add oxygen to the fluid medium circulating in the fluid circuit.

In some implementations, the microfluidic chip includes a flow sensor configured to measure a flow rate of the fluid medium in the fluid circuit; and a controller in communication with the flow sensor and the pump, the controller configured to: obtain data specifying a desired flow rate of the fluid medium; receive a signal specifying the flow rate measured by the flow sensor; and generate, in response to receiving the signal specifying the flow rate, a pump control signal configured to cause the pump to pump the fluid medium at the desired flow rate.

In some implementations, the microfluidic chip includes a valve, the valve being moveable to a first position that allows the fluid medium to circulate in the fluid circuit through the cell chamber, and the valve being moveable to a second position that isolates the cell chamber from the fluid circuit to enable seeding of the cell chamber with the cells.

In some implementations, the microfluidic chip includes a sample carousel, the sample carousel comprising one or more sample chambers configured to store a portion of the fluid medium, the one or more sample chambers being removable from the sample carousel to remove the portion of the fluid medium from the fluid circuit.

In some implementations, the re-oxygenation chamber comprises an oxygen permeable membrane for receiving oxygen from an environment outside of the fluid circuit.

In some implementations, the re-oxygenation chamber includes a redistribution cutout.

In some implementations, the fluid circuit comprises a resistive tubing configured to limit a flow rate in the fluid circuit.

In some implementations, the microfluidic chip includes a first oxygen concentration sensor configured to measure oxygen concentration in the fluid medium at an input of the cell chamber; and a second oxygen concentration sensor configured to measure the oxygen concentration in the fluid medium at an output of the cell chamber.

In some implementations, the microfluidic chip includes an air inlet port configured to provide oxygen to the re-oxygenation chamber, and an air outlet port configured to remove air from the re-oxygenation chamber.

In some implementations, the microfluidic chip includes a second fluid circuit comprising a second cell chamber, the second fluid loop configured to circulate second fluid medium that is isolated from the fluid medium of the fluid circuit.

In some implementations, the cell chamber is seeded with liver cells, adipose cells, single liver cell types, or multiple cell types. Generally, any cell type can be seeded in the cell chamber. Shear-sensitive cells are exposed to relatively slow flow rates, and shear-dependent cells can be exposed to higher flow rates.

In some implementations, the cell chamber includes a volume to cell ratio of about 0.5 mL/200,000 to 2 mL/200,000, and wherein a flow rate of the fluid medium is about is based on each of a minimum oxygenation level for a particular cell type and maintaining a shear stress below a threshold level.

In some implementations, the cell chamber comprises a waterfall feature, the waterfall feature including a step from a first level of the cell chamber to a second level of the cell chamber. In some implementations, the step is 2-3 mm in height.

In some implementations, the cell chamber forms part of an insert that is removable from the fluid circuit. In some implementations, the insert includes a platform for perfusion of cells, for seeding cells, or both.

In some implementations, the platform includes a permeable membrane configured to allow the fluid media to pass through and supports the plurality of cells.

In some implementations, the insert includes a top cover configured to be coupled to a top of a substrate to seal the cell chamber.

In some implementations, the insert includes a bottom cover configured to be coupled to a bottom layer to seal the cell chamber, the bottom cover including the cell chamber.

In some implementations, the cell chamber includes a single compartment.

In some implementations, the cell chamber includes a dual-compartment configuration including an apical side and a basal side.

In some implementations, the cell chamber is a first cell chamber, the microfluidic chip further comprising a second cell chamber configured to receive the fluid media in sequence with the first cell chamber.

In some implementations, the microfluidic chip includes a transwell adapter for interfacing the cell chamber with a transwell.

In some implementations, the cell chamber is part of an insert that is configured for seeding the plurality of cells. The microfluidic chip further includes one or more clamps configured to secure the insert; and a seeding cover configured to cover the insert.

In some implementations, the microfluidic chip includes a sampling port configured to enable removal of a portion of the fluid medium from the fluid circuit.

In some implementations, the cell chamber comprises a seed port for seeding the cell chamber and a waste port for removing waste cells from the cell chamber.

In a general aspect, a support module includes a controller; and a support platform configured to receive the microfluidic chip previously described. The support platform configured to couple the microfluidic chip to the controller for communicating data between the controller and the pump of the microfluidic chip.

In some implementations, the pump includes a peristaltic pump. In some implementations, the pump includes a pneumatic pump. In some implementations, the pump includes a diaphragm pump.

In some implementations, the support module includes an oxygen meter port configured to interface an oxygen sensor with the microfluidic chip.

In some implementations, the support module includes a user interface configured to enable a user to input control parameters for controlling operation of the microfluidic chip, the control parameters comprising one or more of a flow rate, an oxygen concentration in the cell chamber, and a pump speed of the pump.

In some implementations, a memory port configured to receive a memory device, the memory configured to store one or more configuration parameters for operation of the microfluidic chip and data received from the microfluidic chip.

In some implementations, the controller is configured to: receive identifier data from the microfluidic chip, obtain one or more control parameters that are associated with the identifier, and automatically control operation of the microfluidic chip in accordance with the one or more control parameters.

In some implementations, the support module includes a filter stand for supporting an oxygen filter of the microfluidic chip.

In some implementations, the support module includes a pH sensor configured to measure a pH of the fluid medium.

In some implementations, the support module includes a user interface configured to enable a user to input control parameters for controlling operation of the microfluidic chip, the control parameters comprising one or more of a pump speed, an oxygen concentration in the cell chamber, and a pump speed of the pump.

In some implementations, the support module includes a memory port configured to receive a memory device, the memory configured to store one or more configuration parameters for operation of the microfluidic chip and data received from the microfluidic chip.

In some implementations, the controller is configured to: receive identifier data from the microfluidic chip; obtain one or more control parameters that are associated with the identifier; and automatically control operation of the microfluidic chip in accordance with the one or more control parameters.

In some implementations, the controller is configured to control operation of a plurality of instances of the microfluidic chip in parallel.

In some implementations, the support module includes a mechanical device configured to interface with a sampling carousel on the microfluidic chip, wherein the mechanical device is configured to control a position of the sampling carousel during operation of the microfluidic chip.

The details of one or more embodiments of these systems and methods are set forth in the accompanying drawings and the description to be presented. Other features, objects, and advantages of these systems and methods are apparent from the description and drawings, and from the claims.

BRIEF DESCRIPTION OF THE DRAWINGS

FIGS. 10A and 10B each show an illustration of an example of a recirculating microfluidic chip.

FIGS. 11A, 11B, and 11C each show representations of oxygen consumption in a re-oxygenation chamber of a microfluidic chip.

DETAILED DESCRIPTION

This disclosure describes microfluidic chips configured for recirculation of a fluid medium and re-oxygenation of cell cultures within the microfluidic chips. This disclosure describes hardware support systems for controlling recirculation of the fluid medium and re-oxygenation of the cell cultures within the microfluidic chips. A MPS can be referred to as organ construct house in a microfluidic chip and organ on chips (OOC). In some implementations, the cell chambers of the microfluidic chip are called compartments. In the microfluidic chips described herein, the microfluidic chip generally includes a fluid circulation loop for recirculating fluid through a cell chamber including cell tissue of a given cell type or types. Generally, the fluid is continuously recirculated through the cell chamber in a closed loop. The fluid loop generally includes a re-oxygenation chamber to re-oxygenate oxygen-depleted fluid medium recirculating through the fluid loop, as the oxygen is absorbed by the cells of cell chamber. The microfluidic chip design can be based on the oxygen requirements of the cells in the cell chamber and the maximum shear stress tolerances and oxygen absorption rates of those cells, which can limit flow rates of the fluid medium.

Figure 1A:
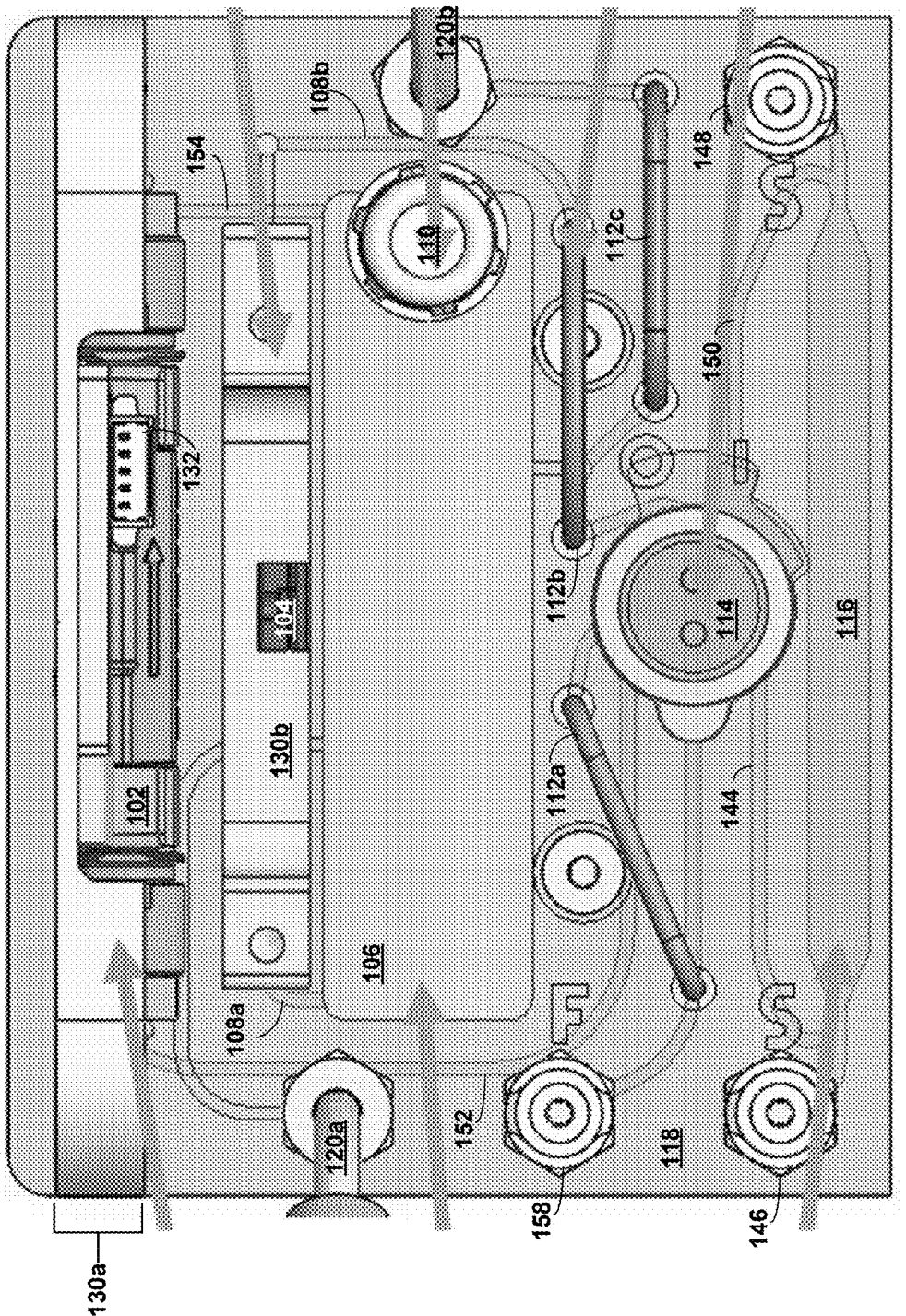
FIG. 1A illustrates a top view of an example microfluidic chip for a recirculating liver chip.

FIG. 1A illustrates a top view of an example microfluidic chip 100 for a recirculating liver chip. The microfluidic chip 100 is configured to emulate organ functionality. The tissue that can be hosted may include liver tissue, adipose tissue, kidney tissue, muscle tissue, or most any tissue type. Generally, depending on the tissue type, a geometry of a cell chamber hosting the tissue is adjusted as described herein. A microfluidic chip 100 is configured to enable preclinical drug discovery and assist in developing treatments for various diseases. A microfluidic chip 100 enables long-term tissue mono- or co-culture (e.g., longer than 4 weeks). The microfluidic chip 100 includes a substrate 118 in which various components, such as a pump 104 in a pump housing 130b and a flow sensor 102 in a housing 130a, are mounted in relation to one another. The substrate 118 includes channels such as ports 108a-b and channels 112a, 112b, and 112c that connect each of the components of the microfluidic chip 100 to form a fluid loop.

The microfluidic chip 100 includes a fluid circulation loop configured to re-circulate fluid in the microfluidic chip through a cell chamber 116 including tissue that is the subject of organ emulation or other experimentation. Generally, the fluid medium is continuously recirculated through the cell chamber 116 in a closed loop. The fluid loop generally includes a re-oxygenation chamber 106 to re-oxygenate oxygen-depleted fluid medium recirculating through the fluid loop, as the oxygen is absorbed by the cells of cell chamber 116. The geometry of the cell chamber 116, loop, re-oxygenation chamber 106, etc. is generally based on the oxygen level requirements of the liver or adipose cells in the cell chamber 116.

The fluid loop includes a pump 104, a flow sensor 102, a re-oxygenation chamber 106, a cell culture chamber 116, a valve 114, and input and output ports such as ports 110, 146, and 148. Port 146 can be a seeing port, and port 148 can be a waste port. The seeding port 146 and the waste port 148 are used in a seeding configuration to introduce a cell culture to the cell chamber 116. In some implementations, the port 158 is used to add additional material to the fluid loop. The fluid loop also includes channels such as channels 108a, 108b, 112a, 112b, 112c, 144, 150, 152, and 154 that connect the flow sensor 102, pump 104, chamber 106, chamber 116, valve 114, and ports 110, 146, and 148 to one another in a continuous loop. This fluid circuit can be configured to introduce substances (e.g., drugs or other substances) to the cell chamber 116 to emulate functionality of in vivo human tests, as subsequently described.

The microfluidic chip 100 includes a pump 104 configured to circulate the fluid medium through the fluid loop of the microfluidic chip. The pump 104 receives fluid through an inlet port 108a, pumps the fluid through an outlet port 108b through a fluid channel 112b to a valve 114. The pump 104 receives fluid through the port 108a from the re-oxygenation chamber 106. The pump 104 is coupled to the substrate 118 of the microfluidic chip 100 by a housing 130b.

The re-oxygenation chamber 106 is configured to enable oxygen to mix with the fluid to reintroduce oxygen at specified concentrations to the fluid medium of the fluid loop. Port 120a and port 120b enable pressure equilibration for the microfluidic chip, while a permeable membrane of the chamber 106 enables air to enter the chamber and mix with the fluid medium, dissolving in the fluid medium and re-oxygenating the fluid medium (as subsequently described). The re-oxygenation chamber 106 is connected to a sampling port 110 that enables samples of the fluid medium to be removed from the fluid loop for analysis. For example, the oxygen concentration, drug concentration, etc. of the fluid medium can be measured by extracted fluid through the sampling port 110. This can enable analysis of how much oxygen or a drug has been absorbed by the cells of the cell chamber 116.

The pump 104 is configured to pump the fluid medium from the re-oxygenation chamber 106 to the valve 114. The valve 114 is configured to change positions (as subsequently described) to enable fluid flow through the valve 114 from the channel 112*b* to the input port 144 of the cell chamber 116. The valve enables fluid to flow from the exit port 150 of the cell chamber 116 to the channel 112*a* or to the channel 152 that leads to the flow sensor 102. The flow sensor 102 is configured to sense a flow rate of fluid in the fluid loop. The flow sensor data is accessible by port 132. Fluid flowing through the flow sensor 102 flows through channel 154 back to the re-oxygenation chamber 106 to complete the fluid loop. The flow sensor 102 is coupled to the substrate 118 by a flow sensor housing 130*a*.

The cell chamber 116 includes tissue that can be subjected to drugs or other materials in the fluid for emulation of tissue functionality. For example, the cell chamber 116 can include most any tissue type. The chamber 116 is connected to an inlet port 144 for receiving fluid from the valve 114 of the circulation loop of the microfluidic chip. The chamber 116 is connected to a cell seeding port 146 for introducing the liver cells or adipose cells to the cell chamber 116. The chamber 116 is connected to a waste port 148 for removing waste material from the chamber or fluid circulating loop of the microfluidic chip 100. The chamber 116 is connected to an outlet port 150 for fluid flow exiting the chamber 116 back to the valve 114.

The cell source can be human primary cells, stem cells or cell lines. Alternatively, primary cells and/or immortalized cell line be used as sources for tissue in the microfluidic chip 100. Generally, primary cells are cells that have been isolated and then used relatively quickly (e.g., immediately) or after cryopreservation. Diseased cells representing one or more stages of a disease can be introduced into the cell chambers of the microfluidic chip 100.

The microfluidic chip 100 is configured for disease modeling by enabling emulation of tissues in controlled environments. For performing a test, there can be an induction of disease in the cells of the microfluidic chip 100 in the prepared liver and/or adipose tissues. The disease progression can be monitored over long periods of time. In some implementations, the microfluidic chip 100 can include cells from diseased patients. Many different mechanisms can be used for on-chip disease induction, as subsequently described.

The microfluidic chip 100 is configured for disease characterization. For example, multi-scale assays can be performed using the microfluidic chip 100. The microfluidic chip 100 enables evaluation of cell construct and tissue construct functions. The microfluidic chip 100 enables a comparison of healthy phenotypes and disease phenotypes. The microfluidic chip 100 enables acquisition of data from pre-determined phenotypic metrics and -omics analysis, as subsequently described.

A computing system (not shown) uses data developed from the MPS 100 to combine MPS models with model-informed drug discovery (MIDD) methodologies in a processing workflow. The processing workflow, described in relation to U.S. patent application Ser. No. 17/104,708, filed on May 27, 2021, incorporated in entirety by reference herein, can be used to develop an understanding of disease diagnostic and response biomarkers. The computational modeling is performed for target (e.g., drugs or drug combinations) discovery using the MPS data of the MPS 100 and systems biology (SB) and quantitative systems pharmacology (QSP) based models. These models are configured to identify molecular abnormalities for diseased cells or tissues. The models link the molecular data to the phenotypic data. Here, phenotypic data can include clinical information regarding disease symptoms, as well as relevant demographic data (if applicable), such as age, ethnicity and sex.

The microfluidic chip 100 is configured to emulate portions of the liver or fatty tissue of a human. Data obtained from this emulation is used by the computing system model to validate a physiological relevance and identify molecular changes (e.g., of various NAFLD phenotypes). For example, the microfluidic chip 100 can be configured to identify and validate cell-specific targets for NAFLD.

The microfluidic chip 100 is configured for drug target discovery and drug development. Each platform 100, 115 combines a tissue-engineered MPS "on-chip" model. Data generated by analyzing the behavior of the tissue of the microfluidic chip 100 can be used to establish metabolically dysfunctional (MetS) MPSs and spheroid models for the liver and adipose tissue of a human. In an example, the primary human parenchymal and non-parenchymal liver cells can be sourced from a single donor for all aims and experiments to minimize the risk of adverse allograft interactions (e.g. Kupffer cell allo-antibodies). Metabolic dysfunction can be induced by culturing the microfluidic chip 100 in a defined, serum-free medium containing disease-relevant concentrations of glucose, fructose, insulin, FFAs, and TNF-$\alpha$ (multi-hit medium (MHM)) and then compared to microfluidic chips cultured in a physiologically healthy medium (PHM). Details of this analysis are described in U.S. patent application Ser. No. 17/104,708, filed on May 27, 2021, incorporated in entirety by reference herein.

Figure 1B:
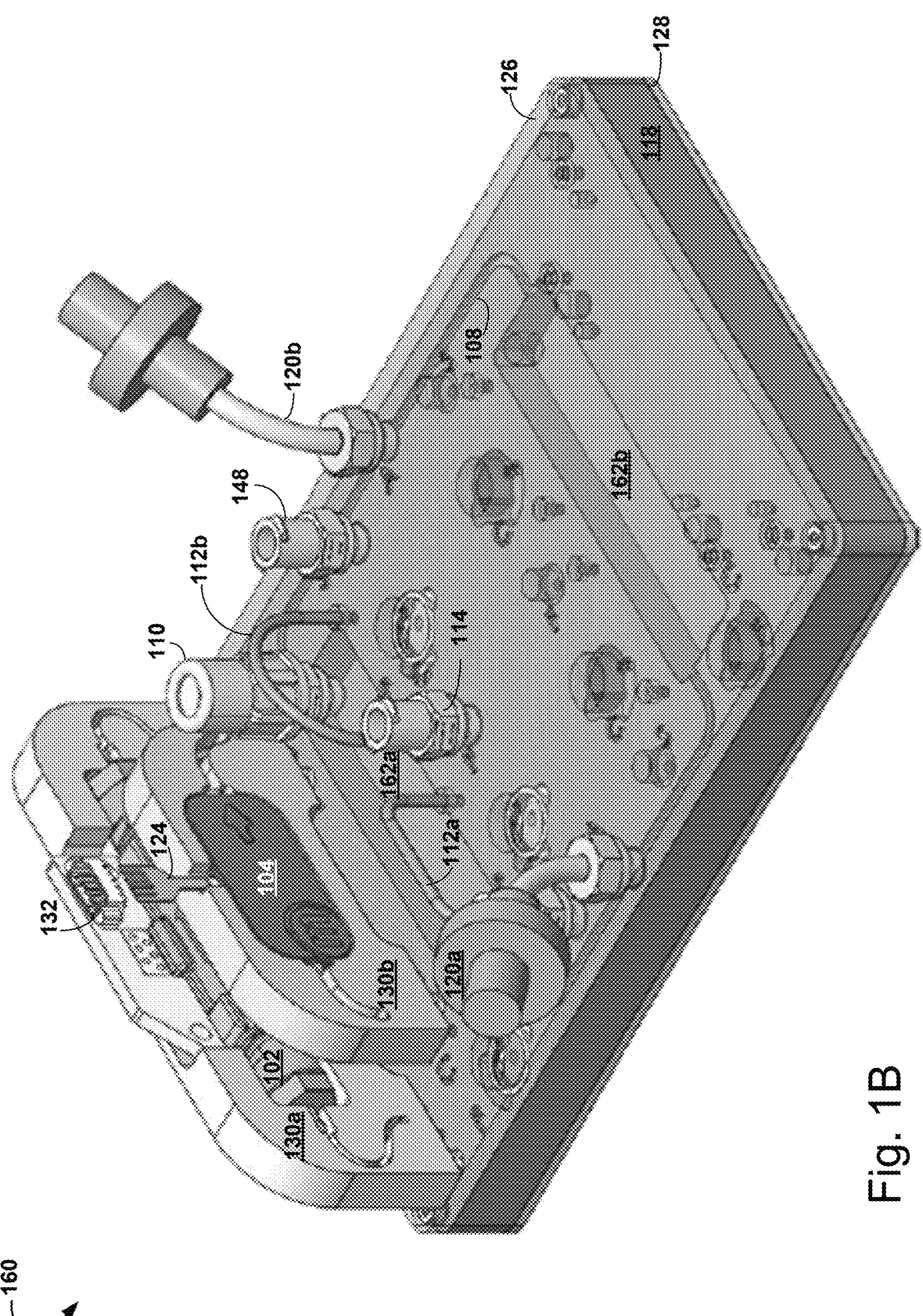
FIG. 1B illustrates a perspective view of the microfluidic chip of FIG. 1A.

FIG. 1B illustrates a perspective view of a microfluidic chip 160 similar to the microfluidic chip 100 of FIG. 1A. The microfluidic chip 160 includes the fluid circulation loop similar to that of microfluidic chip 100, including the fluid pump 104, the flow sensor 102, the port 120*a* and the port 120*b*, valve 114, and sampling port 110. The microfluidic chip 160 includes two re-oxygenation chambers 162*a*, 162*b*, similar to the re-oxygenation chamber 106 of microfluidic chip 100. Each of the re-oxygenation chambers 162*a*, 162*b* are connected to the port 120*a* and the port 120*b* for pressure equilibration. While FIG. 1B shows two MPS fluid loops in a single chip. The fittings (e.g., pumps, valves etc.) are not shown for the second MPS. Chamber 162*a* is for upper half MPS, and chamber 162*b* is for the bottom half. Here, cell culture chambers are not shown for clarity of the other components.

The perspective view of the microfluidic chip 160 shows the substrate 118 below a top layer 126 and a bottom cover 128 below the substrate 118. The substrate 118 includes a spacer between the top layer 126 and the bottom layer 128 and gives height to the cell chamber 116. The bottom cover 128 forms a base for the microfluidic chip 160. The bottom cover 128 supports the various chambers and channels of the microfluidic chip 160 of the microfluidic layer. The bottom cover 128 is a solid platform that stabilizes the microfluidic chip 100 and provides a foundation for the microfluidic chip.

The substrate 118, or the microfluidic layer 118, includes the chambers and channels of the microfluidic chip 100 for fluid flow through the system. For example, the liver and/or adipose cells and tissues are hosted in these chambers and/or channels as needed to emulate tissue functionality. The microfluidic layer is patterned into a polymer material (e.g., a polycarbonate (PC)) as subsequently described. The microfluidic layer is laminated between the bottom cover 128 and the top layer 126. The microfluidic chip 160 enables mono-cultures and co-cultures of various liver and adipose types in 2D and 3D in the chambers to be sealed by the layers 126 and 128.

The top layer 126 includes interconnecting tubes (e.g., 112a-c). In an example, the tubes of the top layer 126 are resistive tubing to control flow rates. For example, the tubes 112a-c can control fluid flow at the desired rate so that tissue functionality is accurately emulated.

Generally, the top layer 126, the bottom cover 128, and the microfluidic layer 144 are fabricated into thermoplastic materials. The fabrication can include one or more processes such as laser/plotter cutting, CNC machining, and microinjection molding. The microfluidic chip 160 can be fabricated using thermoplastics such as polymethyl methacrylate (PMMA), polycarbonate (PC), polysulfone (PSU), or cyclic olefin copolymer (COC). In some implementations, the hardware platform 140 is PDMS-free to minimize undesirable non-specific adsorption of lipophilic molecules. The bottom cover 128 can be laminated with a gas permeable material to accurately reflect the incubator conditions. While three layers are shown, a fourth layer (not shown) can be included. The fourth layer includes a membrane layer between the top layer 126 and the microfluidic layer 118.

Figure 1C:
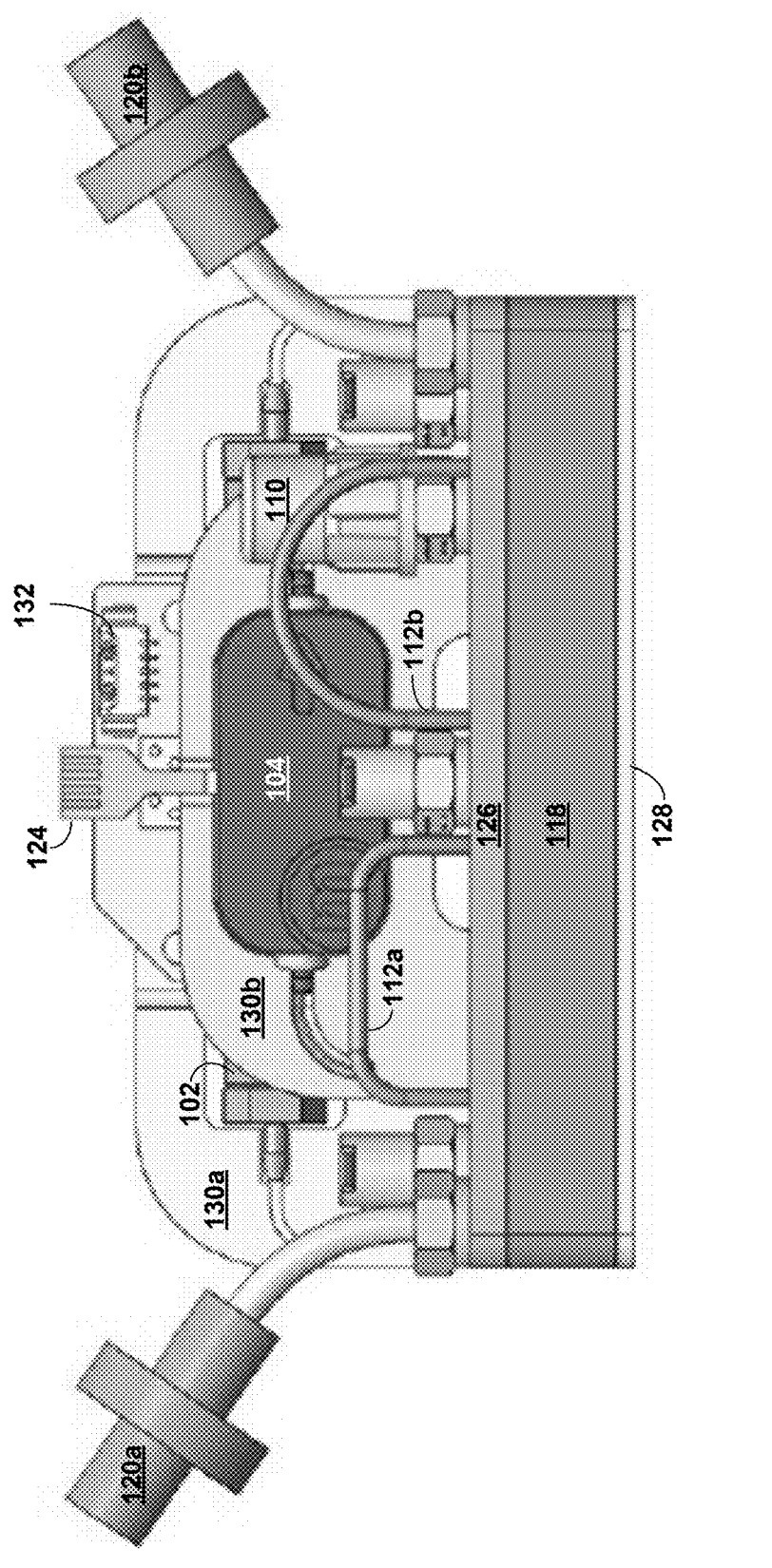
FIG. 1C illustrates a side-view of the microfluidic chips of FIGS. 1A-1B.

FIG. 1C illustrates a side-view of the microfluidic chips 100 of FIG. 1A. The geometry of the layers 126, 118, and 128 is shown. The tubes 112a-b protrude from the substrate 118 and the top cover 126.

The control port 124 of the pump 104 is shown more clearly in FIG. 1C. The control port 124 enables a remote device (such as a hardware support module, subsequently described) to send data to and receive data from the pump 104. For example, a control signal for a pump rate can be sent by a controller to the pump 104 using the port 124, and the pump 104 can report back a pump rate or acknowledgement to the controller.

Similarly, the flow sensor 102 can be electrically connected to a controller (not shown) using a control port 132. The control port 132 includes one or more pins for reading flow rate values from the flow sensor 102. The flow rate values indicate to the controller what the actual flow rate is of the fluid medium in the fluid circuit. In some implementations, multiple flow sensors 102 or pumps 104 can be provided and controlled in parallel by the remote device controller.

Figure 2A:
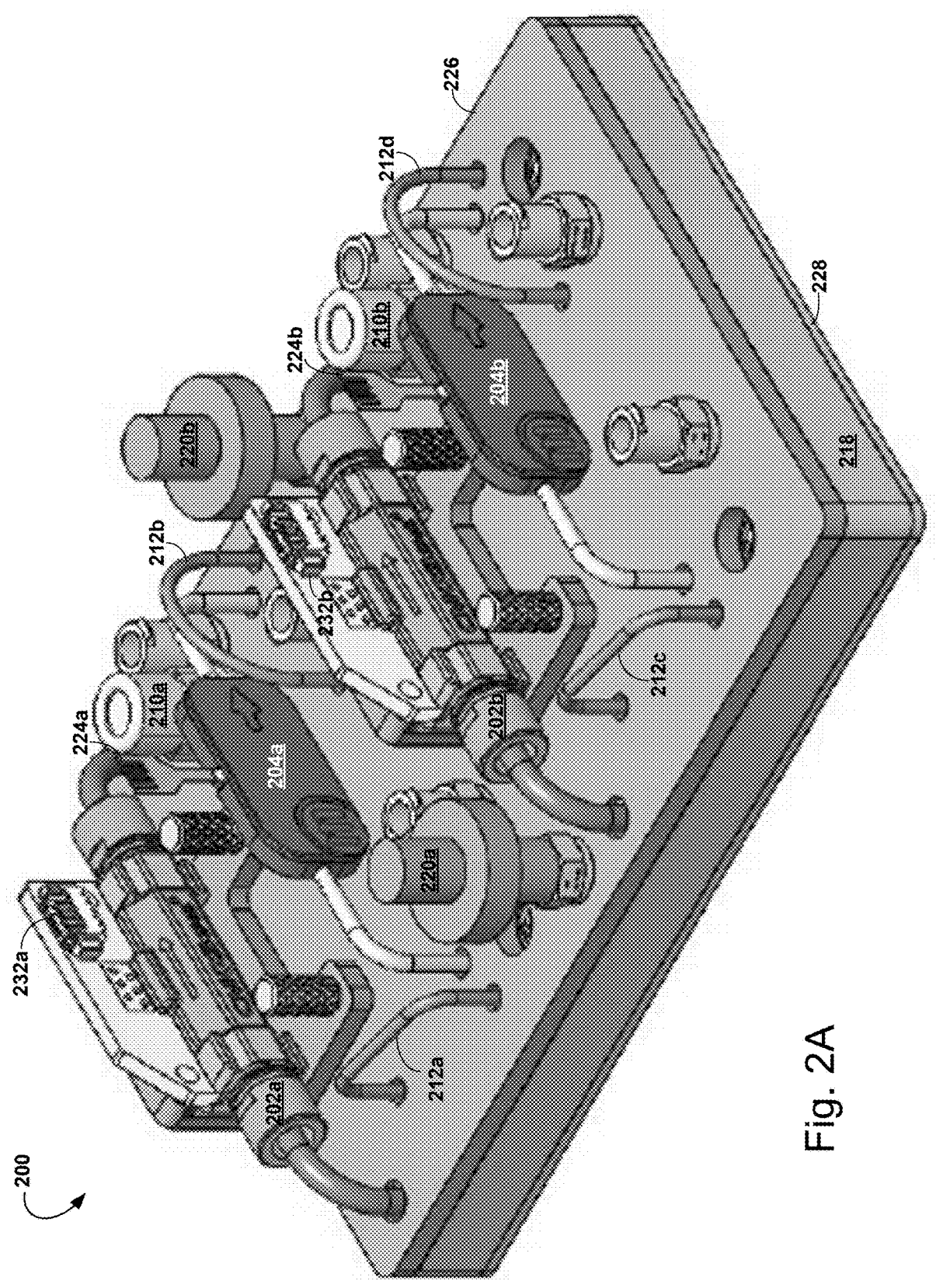
FIG. 2A illustrates a perspective view of an example microfluidic chip.

FIG. 2A illustrates a perspective view of an example microfluidic chip 200. The microfluidic chip 200 is similar to microfluidic chip 100, except that microfluidic chip 200 is configured for two fluid circuits. The two fluid circuits can operate independently from one another (e.g., to perform two individual experiments). In some implementations, a single controller (not shown) can be configured to operate both fluid circuits.

A first circuit includes flow sensor 202a, pump 204a, channels 212a-b, and sampling port 210a. The first circuit also includes a re-oxygenation chamber (not shown) and a cell culture chamber (not shown), which are each under the top cover 226 in the substrate layer 218, as described in relation to FIGS. 1A-C. In this example, the flow sensor 202a is similar to flow sensor 102. In this example, pump 204a is similar to pump 104. In this example, channels 212a-b are similar to channels 112a-b. In this example, sampling port 210a is similar to sampling port 110. In this example, connector port 232a is similar to connector port 132. In this example, control port 224a is similar to control port 124.

A second circuit includes flow sensor 202b, pump 204b, resistive elements 212c-d to control flow rate, and sampling port 210b. The first circuit also includes a re-oxygenation chamber (not shown) and a cell culture chamber (not shown), which are each under the top cover 226 in the substrate layer 218, as described in relation to FIGS. 1A-C. In this example, the flow sensor 202b is similar to flow sensor 102. In this example, pump 204b is similar to pump 104. In this example, resistive flow elements 212c-d are similar to resistive flow elements 112a-b. In this example, sampling port 210b is similar to sampling port 110. In this example, connector port 232b is similar to connector port 132. In this example, control port 224b is similar to control port 124. Ports 220a and 220b are configured equilibrate air pressure.

Figure 2B:
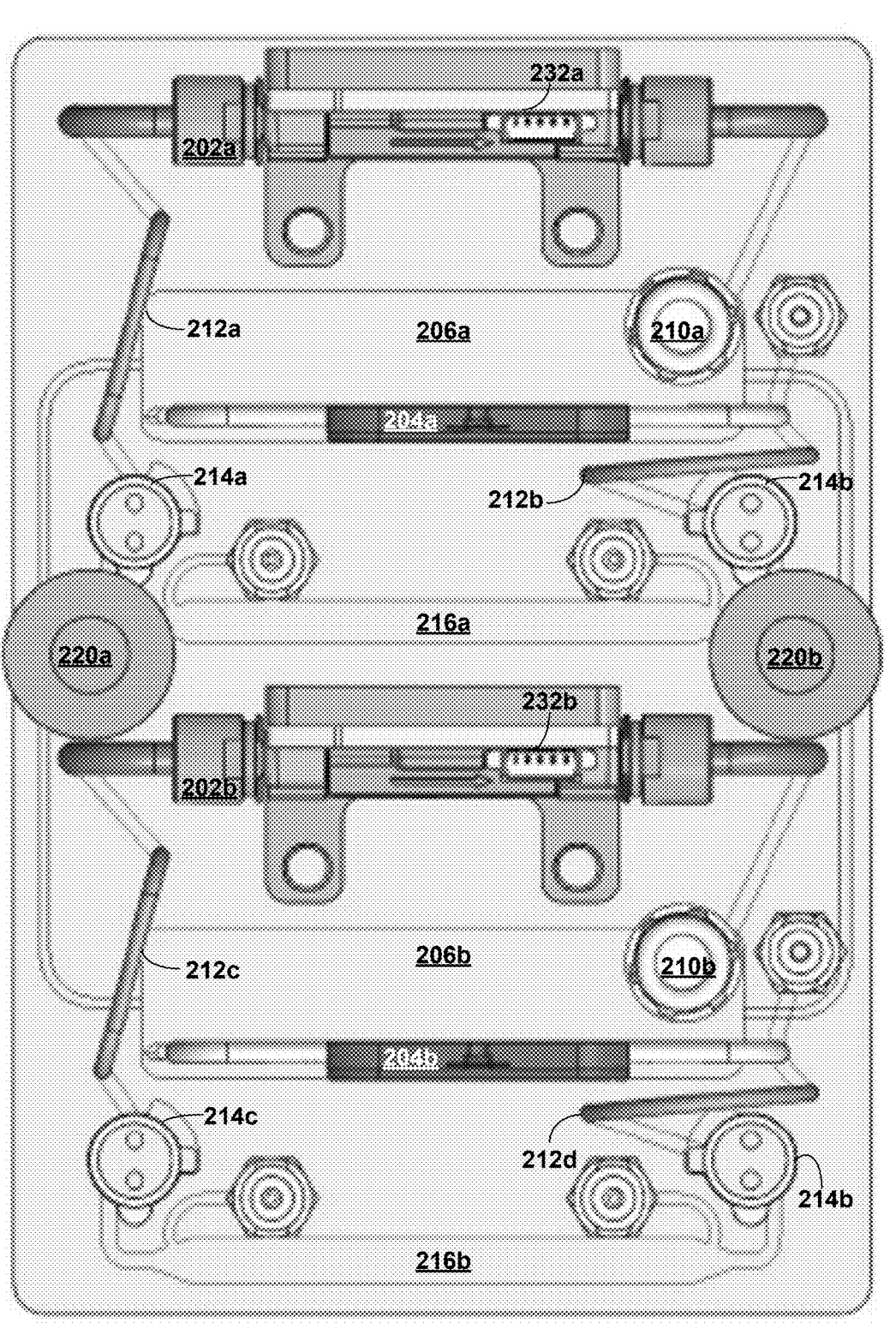
FIG. 2B illustrates a top view of the microfluidic chip of FIG. 2A.

Turning to FIG. 2B, a top view of the microfluidic chip 200 of FIG. 2A is shown. In FIG. 2B, the top cover 226 is removed to show a first re-oxygenation chamber 206a and a first cell chamber 216a of the first fluid circuit. The microfluidic chip 200 also includes a second re-oxygenation chamber 206b and a second cell chamber 216b of the second fluid circuit. In an example, and in a similar manner as described in reference to the fluid circuit of FIGS. 1A-1C, the pump 204a circulates fluid through the first cell chamber 216a and the first re-oxygenation chamber 206a. In parallel, in a similar manner as described in reference to the fluid circuit of FIGS. 1A-1C, the pump 204b is configured to circulate fluid through the second re-oxygenation chamber 206b and the second cell chamber 216b.

The pressure equilibration ports 220a-b are each connected to both of the fluid loops. The valves 214a-b of the first circuit and the valves 214c-d of the second circuit are used for seeding and cell perfusion. The valves 214a-d can be actuated or opened manually to move from respective first positions to second positions to enable cell seeding and perfusion, and subsequently sealing the fluid loop. In some implementations, the first and second fluid circuits can be controlled through a user interface, as described in relation to FIG. 6C.

Figure 3A:
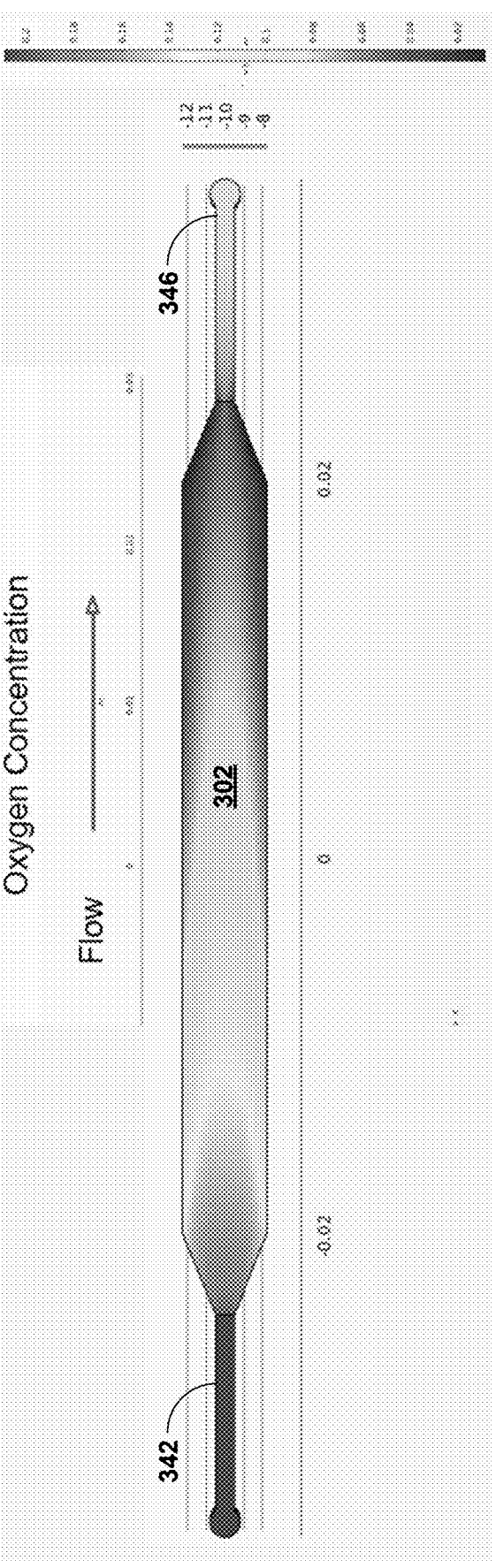
FIG. 3A illustrates a computational fluid dynamics (CFD) model for a chamber of a microfluidic chip showing oxygen concentration.

Turning to FIG. 3A, a diagram 300 shows a representation of computational fluid dynamics (CFD) for a cell chamber 302. Chamber 302 can be similar to chamber 116 previously described. The cell chamber can be designed using computational fluid dynamics (CFD) to provide physiologically relevant oxygen tension to the liver culture, while minimizing the shear stress (e.g., less than 0.05 dyne/cm$^2$). In some implementations, the cell culture area can be approximately 40 millimeters (mm) by 5 mm and hold up to a million cells. However, other sizes for cell chambers are possible, and the fluid flow rate can be adjusted based on the cell chamber geometry and size, as described herein. The laser-cut PC layers are laminated with an optimized bonding protocol (e.g., a thermal bonding protocol, a solvent-based bonding protocol, etc.). The chips are perfused with pneumatic pumps (or displacement pumps) with a wide range of flow rates (e.g., 0-100 mL/day). The microfluidic chip 100 is characterized for long-term culture biocompatibility (e.g., greater than 28 days) and validated using cell morphology, cell viability, and cytotoxicity assays. For the chamber 302, there is relatively low oxygen on edges where fluid is flowing slowly. The low concentration areas grow along the fluidic path due to continued oxygen consumption from the cells as flow moves from left to right in the diagram 300.

Figure 3B:
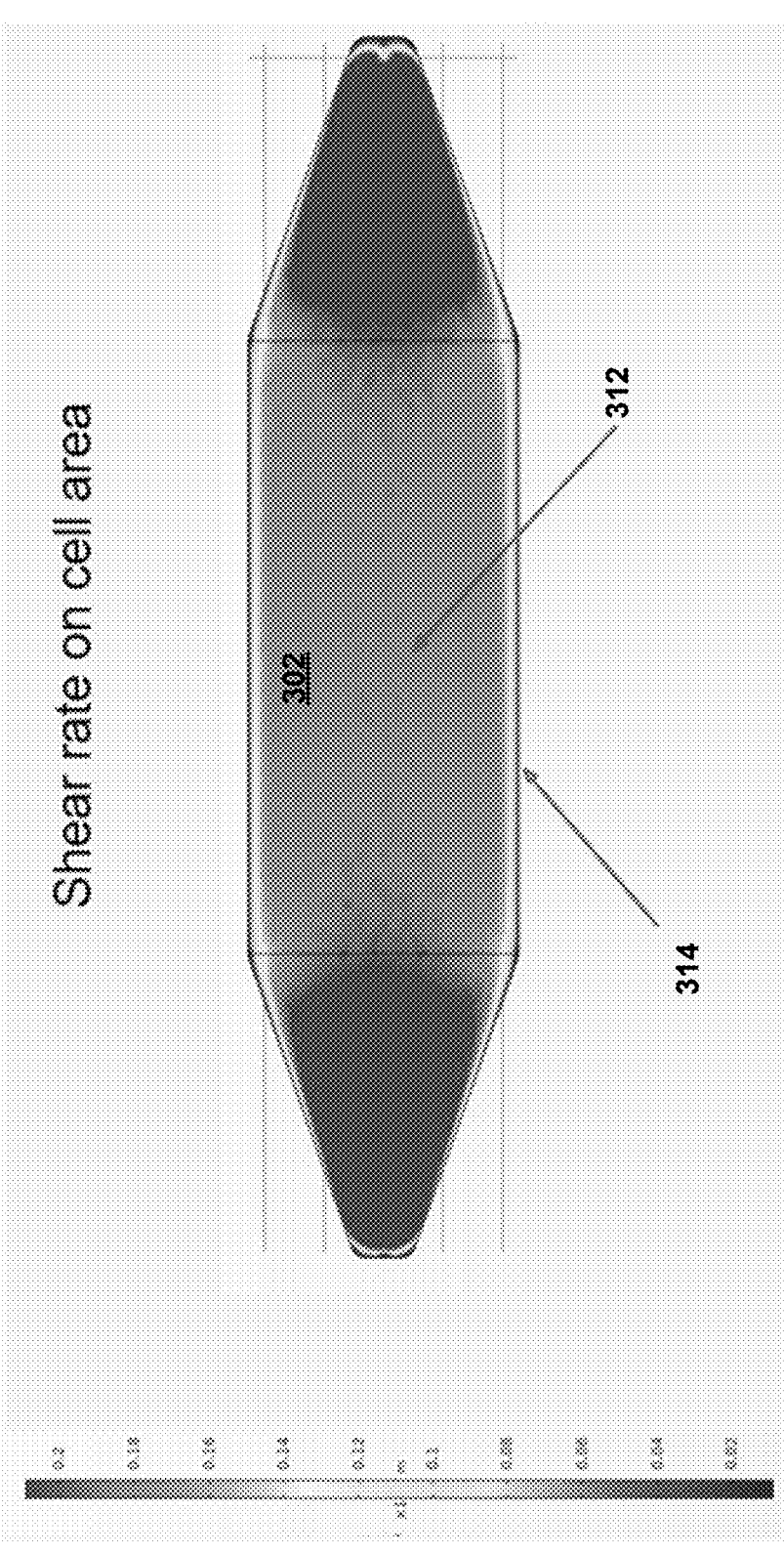
FIG. 3B illustrates a CFD for a chamber of a microfluidic chip showing shear rate.

FIG. 3B illustrates a CFD diagram 310 for a chamber 302 (e.g., cell chamber 116 of microfluidic chip 100 of FIG. 1) showing shear rate of fluid flow in the chamber. In the example chamber geometry shown in FIG. 3B, the fluid has a high shear rate on the walls 312 of the chamber and a low shear rate in the corners 314 of the chamber 302. This example is shown for liver tissue, but other tissues can be used (with different flow rates and resulting shear stress values).

Generally, there are several considerations for determining the design of the microfluidic chip system, such as the geometry of the cell chamber 302 or other design parameters. Here, the geometry refers to the shape of the cell chamber and fluid channels, which can include shapes that affect fluid flow, surface area of the cell, cell area, and so forth.

A second consideration for determining values of design parameters for the cell chamber 302 is an amount of oxygen delivery. The oxygen delivery level is controlled based on the values of the geometric or flow rate parameters that are chosen. A sufficient oxygen level is provided to the cell chamber by the flow of the fluid medium. The sufficient oxygen level ensures that the cells of the tissue are exposed to oxygen-containing media (>1%). Generally, a flow rate parameter is selected. The flow rate is the amount of fluid medium passing through the cell chamber 302, such as by the pumps 104, 204*a-b* of microfluidic chips 100, 200. Higher flow rates enable more oxygen to be present in the channel over a given time. A channel height parameter is determined. The channel height or chamber height is a geometric size of the chamber 302. A higher height value results in an increased size of an oxygen gradient. As a result, the oxygen concentration various more in the cell chamber 302, and it is more difficult to enable oxygen to reach the entire cell chamber 302. The example of a gradient is shown in FIG. 3A, in which the portion of the cell chamber 302 near the outlet port 346 has a lower oxygen concentration than the portion of the cell chamber near the inlet port 342.

The amount of oxygen delivery is determined based on the cell type. Generally, each particular cell type is associated with a particular oxygen consumption requirement. The oxygen requirement parameter based on the OCR of the cells. Generally, cells having a lower OCR consume less oxygen. The sufficient oxygen level in the oxygenation chamber can be satisfied with less oxygen. A re-oxygenation chamber surface area can be smaller for these low OCR cell types. A lower flow rate may be required as well.

The amount of oxygen delivery for the cell chamber 302 is based on a number of cells in the cell chamber and a surface area of the cell. Generally, for some tissue types, a minimum seed density is needed to form a viable tissue. A cell density includes a number of cells in a given cell surface area. The cell number is equal to the seeding density multiplied by the surface area. By decreasing a number of cells in the cell chamber 302, if there is a constant seeding density, less oxygen is required for the cell chamber 302.

The third consideration for controlling oxygen levels includes a shear stress. The shear stress refers to shear forces exerted on the cells by fluid flow in the cell chamber 302. FIG. 3B shows an example diagram including example shear levels in the chamber 302. Generally, hepatocytes prefer low shear stress for proper morphology (development). Therefore, shear stresses are minimized in the cell chamber 302 by design of the geometry. Additionally, flow rates are minimized by adjustment of the geometry of the cell chamber 302. For shear stress, the following parameters have the following corresponding effects. For example, changing a flow rate has a linear effect on the shear stress (increasing proportionally). Changing the channel width has a linear effect on the shear stress (inversely proportional). Changing the channel height has a squared effect (inversely proportional). Changes to the geometry of the chamber may affect required flow rates. For example, if a height of the chamber is increased, the oxygen gradient increases, and flow rate is increased to compensate (as previously described).

The exact geometries of chambers and fluid channels of the microfluidic chip depend on the cell type and particular application of the microfluidic chip. This cell chamber 302 can be for the liver recirculating microfluidic chip, such as microfluidic chip 100. The cell chamber 302 have include the following metrics. For example, a shear stress range can be less than $0.05$ dyne/$cm^2$. In some implementations, an OCR range is between 0.06-0.4 nanomols per second per one million cells. In some implementations, a seeding time is between 60-90 minutes for complete oxygen depletion when there is no top membrane. In some implementations, the total cell number is between about 200,000-400,000. The seeding density can be about 200,000 cells per square centimeter. A volume to cell ratio range (mL/cell number) is about 0.5 mL/200,000 to 2 mL/200,000. An example of a typical cell chamber inlet oxygen level is about 37.5-45% absolute saturation (AS). A maximum cell chamber inlet oxygen level is 100% A.S. A typical cell chamber outlet oxygen level is 25-18% A.S. A minimum oxygen level in the cell chamber is 3% A.S. These typical oxygen levels are used to determine the exact geometries of the cell chambers for various microfluidic chips, based on the application (e.g., cell type). The oxygen levels are used to determine fluid medium flow rates, in combination with the channel and cell geometry and maximum shear levels, to control the oxygen level in the cell chamber. While these parameters are examples for the liver cells in the microfluidic chip 100, different cell types or microfluidic chip types have different typical ranges and values for oxygen levels for the cell chamber and thus geometries of the channel and the cell chamber. Thus, these metrics are representative for a particular microfluidic chip type, but other microfluidic chips may have different typical dimensions for the cell chamber and fluid channels.

General values for oxygen levels are now described for various implementations. For example, if there are at least 200,000 cells, and the seeding density is about 200,000 cells per $cm^2$, the surface area of the chamber is 1 $cm^2$. The result is that the minimum chip volume is about 0.5 mL, and the maximum chip volume is about 2.0 milliliters (mL). In another example, if there are at least 400,000 cells, and the seeding density is about 200,000 cells per $cm^2$, the surface area of the chamber is 2 $cm^2$. The result is that the minimum chip volume is about 1.0 mL, and the maximum chip volume is about 4.0 mL. These are examples of general ranges for surface area and chip volume based on seeding density. They are also ranges for the amount of cells and the volume-to-cell ratios. These ranges provide a framework for particular solutions for cell chamber geometry and corresponding flow rates.

Figure 4:
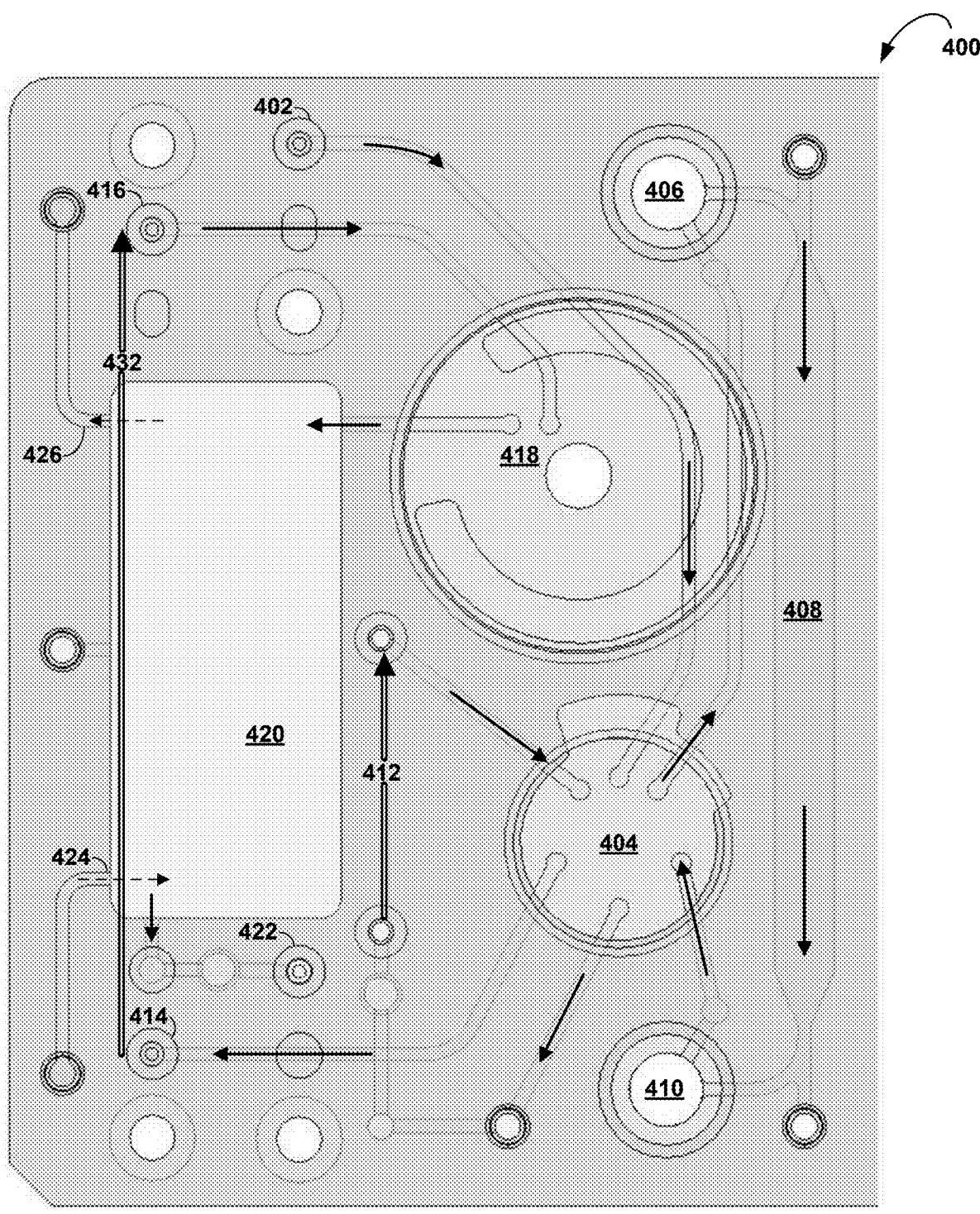
FIG. 4 illustrates an example media flow path through a microfluidic chip.

FIG. 4 illustrates an example media flow path through a microfluidic chip 400 for a recirculating liver chip, including a media sample carousel 418. The particular components of the fluid loop, such as a pump, a flow sensor, air inlet and outlet ports, control ports, etc. can be similar to those of the microfluidic chips 100, 200. For example, similar to micro-fluidic chips 100, 200, microfluidic chip 400 includes a fluid circulation loop for recirculating fluid through a cell chamber 408 including cell tissue. Similar to microfluidic chips 100, 200, the microfluidic chip 400 includes a re-oxygenation chamber 430 to re-oxygenate oxygen depleted fluid medium recirculating through the fluid loop, as the oxygen is absorbed by the cells (e.g., liver cells) of cell chamber 408. For example, the flow sensor (e.g., shown by path 432) can include the same hardware and control port as flow sensor 102 of FIG. 1A. For example, a pump (not shown) can be similar to pump 104 of FIG. 1A. The substrate of microfluidic chip 400 including the channels and chambers can be similar to substrate 118 of FIG. 1A. Though bottom and top layers are not shown in FIG. 4A (just a substrate layer), these layers can be included in a similar configuration to respective layers 128 and 126 of FIG. 1B. In other words, the configuration of the fluid circuit is different in microfluidic chip 400 than in microfluidic chips 100 and 200, including the geometry of the flow channels and chambers and position of these elements in the substrate. However, the overall characteristics of the microfluidic chip 400, including the design constraints for the cell chamber 408, are similar to those previously described in relation to chamber 302 and microfluidic chips 100, 200. However, given that the microfluidic chip 400 includes a different type of cells (generally liver cells), the specific design characteristics of the fluid circuit vary from the microfluidic chips 100, 200.

The fluid circuit of microfluidic chip 400 is now described. Direction of flow of the fluid medium is shown by solid arrows. Direction of air flow from the air inlet 424 and the air outlet 426 are shown by dashed arrows. The fluid circuit includes a pump (not shown) having a pump exit 402. Fluid medium is pumped through the pump out the pump exit 402 along a channel to a valve 404. The valve 404 can be similar to valve 114 of FIG. 1A. The valve 404 directs fluid flow of the fluid medium depending on where in the fluid circuit the fluid is coming from. The valve 404 directs fluid medium from the pump exit 402 to the inlet oxygen sensor 406 near a cell chamber 408 inlet.

The oxygen sensor 406 measures the oxygen level in the fluid medium at the inlet of the cell chamber 408 before the oxygen is absorbed in the cell chamber 406. The fluid medium passes through the chamber 408 and is absorbed by the cells as previously described. The geometry of the cell chamber 408 is determined based on the design parameters described in relation to FIGS. 3A-3E. Once the fluid medium passes through the cell chamber 408, the fluid medium passes through an outlet oxygen level sensor 410. The outlet oxygen level sensor is configured to measure the oxygen level at the outlet of the cell chamber 408. Therefore, a difference between the inlet oxygen level to the chamber 408, measured by sensor 406, and the outlet oxygen level of the chamber 408, measured by oxygen sensor 410, can be determined.

The oxygen-depleted fluid medium passes through the valve 404 to be directed to the flow sensor. In some implementations, the fluid passes through a resistive tube 412 which is configured to limit flow rate to a maximum flow rate. The fluid medium passes through the resistive tube 412 and then is directed in a channel to the flow sensor inlet 414. The fluid passes through the flow sensor which measures the flow rate of the fluid medium in the fluid circuit. The fluid medium passes through an outlet 416 of the flow sensor.

In some implementations, the fluid circuit of microfluidic chip 400 includes a sample carousel 418. The sample carousel 418 can enable sampling of the fluid medium for analysis outside of the microfluidic chip 400. For example, sample vials can collect some fluid medium. The vials can enable testing of drug levels in the fluid to determine how much of a drug is being absorbed by the cells of the cell chamber 408. Other similar tests can be performed on the fluid. In an example, at given time points, samples (e.g., 25-50 μL) are be collected for each vial of the carousel. The carousel is connected to a motor which rotates the carousel to move the sample vials at a given time. The motor will be on the controller and touching the bottom of the chip, driven by the controller. The samples can be used for drug quantification and bio-molecular assays.

Once the fluid medium passes through the sample chamber(s) 418, fluid medium enters the re-oxygenation chamber 420 (also called a reservoir). The fluid mixes with air from the air inlet 424, which flows into the re-oxygenation chamber 420 and out the air outlet port 426. Once the fluid is mixed with the oxygenated air, the air is circulated back through the pump at pump inlet 422. The fluid medium passes through the pump to pump outlet 402 to recirculate through the microfluidic chip 400.

Figure 5:
FIG. 5 illustrates an example schematic of a media flow path through a microfluidic chip for a recirculating.

FIG. 5 illustrates an example schematic 500 of a media flow path through a microfluidic chip. The fluid flow path is similar to that previously described in relation to FIG. 4, though each of the elements of the flow path are described in further detail and can be in a different order. More specifically, FIG. 5 shows a feedback control system for controlling the media flow rate in the circuit 500.

The fluid circuit begins at the diaphragm pump 520 outlet and passes through a re-oxygenation chamber 502 (also called a reservoir). A buffer level sensor measures buffer levels in the reservoir 502. Additionally, a pressure is regulated for air above the fluid to control flow rate. An oxygen/$CO_2$ supply and vent regulate the pressure of the air at 100 mBar. The air pressure is adjusted by pumping at an intended flow rate by the pump 520. The liquid level in the reservoir 502 is monitored. An air pressure is adjusted in the air above the fluid to control the flow rate from the reservoir 502. In another option, the pressure in the reservoir 502 is static. To control the flow rate, the liquid level (e.g., buffer level) is monitored in the reservoir 502. If the liquid level is too low, the liquid is refilled by the pump 520 to maintain flow rate.

The fluid circulates through the reservoir 502 to the infeed oxygen sensor 504 (similar to sensor 406). The fluid flows through channel 506, similar to cell chamber 408 described previously. The cell chamber 408 can include a seeding port and a waste port, similar to chamber 308 described previously. An outlet oxygen sensor 510 measures oxygen levels after absorption by the cells in the chamber 506. This is similar to sensor 410 described in relation to FIG. 4.

The circuit 500 includes a sample extraction device 512. The sample extraction device 512 can be connected to a sample carousel (e.g., carousel 418 of FIG. 4) and enables portions of the fluid medium to be extracted from the fluid loop for analysis outside of the fluid loop, as described in relation to FIG. 4. The sampling chamber can enable samples of up to 25-50 μL to be taken from the fluid loop for each sample.

The fluid circuit can include a particle filter 514. The particle filter is configured to remove particles (e.g., cells removed from cell chamber, etc.) from the fluid medium. The fluid then passes through a resistive tubing coil 516 to regulate the fluid flow rate. The fluid medium passes through a pump reservoir 518 to add buffer material to the fluid medium. The buffered solution then circulates back through the pump 520 to recirculate through the circuit 500.

For feedback control, an integral-based control feedback system can be used. For example, the feedback is based on an integral of the error of the flow rate. An frequency adjustment for the pump is provided:

$$co = co_{bias} + \frac{K_c}{T_i} \int e(t)dt, \tag{1}$$

wherein the feedback loop equation is provided by:

$$\text{Frequnecy}_n = \text{Frequency}_{n-1} + K*\text{Error}_n \tag{2},$$

wherein K is a gain factor (constant) that is determined to increase response time without decreasing system stability. For example, a high gain results in a fast response, but can cause instability due to over-correcting. A lower gain results in a slower, but more stable, response. In some implementations, rather than adjusting pump frequency, pump voltage can be adjusted to change a pump strength.

Figure 6A:
FIGS. 6A-6B show examples of a hardware support module for microfluidic chips.
Figure 6B:
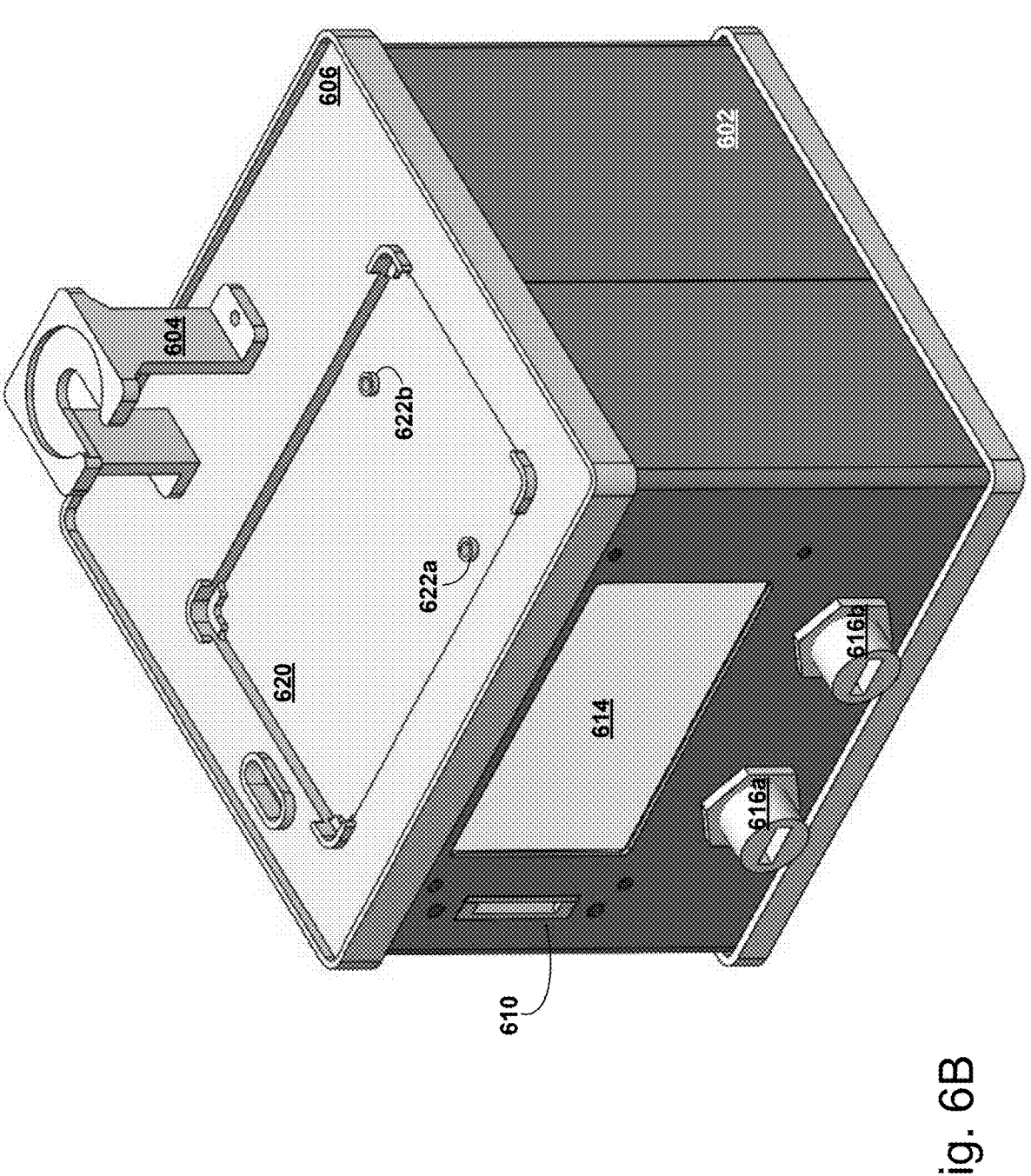

FIGS. 6A-6B show examples of a hardware support module 600 for microfluidic chips. The control module 600 is configured to receive a microfluidic chip 612 (e.g., any of the microfluidic chips described herein).

The support module 600 enables a user to perform flow control for one or multiple microfluidic chips. The support module 600 can be used to autonomously control the flow rate (e.g., with a controller in the support module). In some implementations, the support module 600 allows a user to adjust control parameters (e.g., through a user interface). The support module 600 can be configured to save flow data, control parameters, experimental measurements and metadata, and any system settings. A port 610 enables interfacing of the support module 600 to a removable non-transitory computer readable medium, such as a secure digital (SD) card, USB-based solid state memory, or any other memory medium. In some implementations, the support module 600 comprises a transceiver or other wireless communication device to transmit data to and receive data from a remote computing device.

The support module 600 includes a platform 606 for supporting one or more microfluidic chips. The example shown in FIG. 6 includes a single microfluidic chip. However, one or more additional microfluidic chips of the same or varying configurations from the microfluidic chip 612 or each other can be simultaneously supported for implementations including additional ports for additional microfluidic chips. The support module 600 can control each microfluidic chip individually or in combination with one another.

The support module 600 includes a user interface an interactive display 614. The user interface 614 can include a touch screen enabling a user to set any control parameter for the microfluidic chip 612 to set up the precise experimental conditions for the cells in the cell chamber of the microfluidic chip 612. For example, the user can set the flow rate for the microfluidic chip 612 (and other microfluidic chips) for simultaneous control/operation by the controller of the support module 600. Additionally, the user interface 614 is configured to display data measured from the microfluidic chip 612, such as flow conditions, oxygen levels, buffer levels, or any other data measured in the microfluidic chip, in real time. The support module 600 includes a stand 604 to support a sterile filter, which is part of the microfluidic chip 612. Ports 616a-b are available for connecting additional sensors, air mixtures, computing devices, and so forth. For example, ports 616a-b can be universal serial bus (USB) ports or other such I/O ports.

FIG. 6B shows the support module 600 with the microfluidic chip 612 removed. The slot 620 for the microfluidic chip 612 includes oxygen meter locations 622a-b for interfacing oxygen sensors with the microfluidic chip 612. The integrated oxygen sensing of the module 600 is performed using optical oxygen sensors that read oxygen sensor dots integrated into the microfluidic chip 612.

The support module 600 includes a controller (not shown). The controller is configured for closed loop feedback control for controlling the flow rate, as previously described in relation to FIGS. 4-5. The controller is configured to activate a piezo pump (e.g., pump 104 of FIG. 1A) and a micro-flow meter (e.g., the flow meter 102 of FIG. 1A). The controller of the support module 600 receives the sensor data from the flow meter of the microfluidic chip 612, determines a signal (voltage) to send to the pump, and causes the control signal to be sent to the pump to control operation of the pump. The controller is configured to perform precise flow control at flow rates specified by the user or associated with a particular microfluidic chip. For example, the user can input the control parameters into the module 600 through the user interface 614. In another example, the microfluidic chip 612 may have an identifier that is readable by a sensor of the support module 600. For example, the identifier can include a QR code, radio frequency ID (RFID), or other near field communication mechanism that is readable by a sensor of the module 600. The controller can receive the identifier and select the appropriate control flow settings for automatic configuration when the microfluidic chip 612 is placed on the slot 620. In some implementations, the flow rate is configured to be as low as 1 mL per hour across a variety of process conditions.

The support module 600 can be configured according to one or more of the following features. The support module 600 can include an automatic loading process. The module 600 is configured to store control settings (e.g., from a previous operation). If the module 600 loses power or operations are interrupted, such as due to power failure or user interruption. The module 600 is configured to access the memory storing the settings (e.g., non-volatile memory). The module 600 can thus resume control of fluid flow when the support module 600 is restarted.

The support module 600 can include a controller configured to operate a plurality of pumps, either on a same microfluidic chip 612 (e.g., microfluidic chip 200) or on different microfluidic chips connected to the support module 600. For example, the controller is configured for operation of four pumps with control for different flow rates using an I2C multiplexer. Additional pumps can be added (e.g., up to 8, up to 16, etc.).

The controller is configured for automated data processing of flow sensor data. The controller is configured to preprocess the flow sensor data to remove noise due to air bubbles or other interference. The controller can be configured to detect potential flow stoppage, such as due to bubbles, and generate an alert for presentation to a user. For example, the alert can include an audible alarm, push notification on a remote device, and so forth. The alert can also be generated for other errors with the support module 600 or the microfluidic chip 612, such is if a connection to the pump or flow sensor is lost, if data includes values outside an expected range, after a period of time has elapsed, if pressure of air exceeds a threshold, or if any other error occurs. The controller can be configured to identify the particular error and attempt remediation of the error. For example, if bubbles are detected, the controller is configured to modulate a pump drive voltage to prevent stoppage of flow.

The support module 600 is configured to read sensor data and display, in real time (e.g., within a few seconds of receiving the sensor data from the sensors of the microfluidic chip 612), the sensor data on the display 614. For example, the module 600 is configured to read multiple oxygen sensors (e.g., up to 8 or two per chip). The module 600 is configured for automated sampling control. For example, for microfluidic chip 400, up to 5 samples are available to be taken. If four microfluidic chips are connected to the module 600, then 20 samples can be taken overall, each using separate control. The controller can rotate the sample carousel for incrementing the sample chambers to collect additional samples automatically, as subsequently described. The controller is configured for automatically controlling the sampler position using one or more position sensors, such as Hall-effect sensors and multiple magnets. The controller is configured to adjust flow settings, sampling rate and timing, and oxygen levels without stopping flow in the microfluidic chip 612.

Figure 6C:
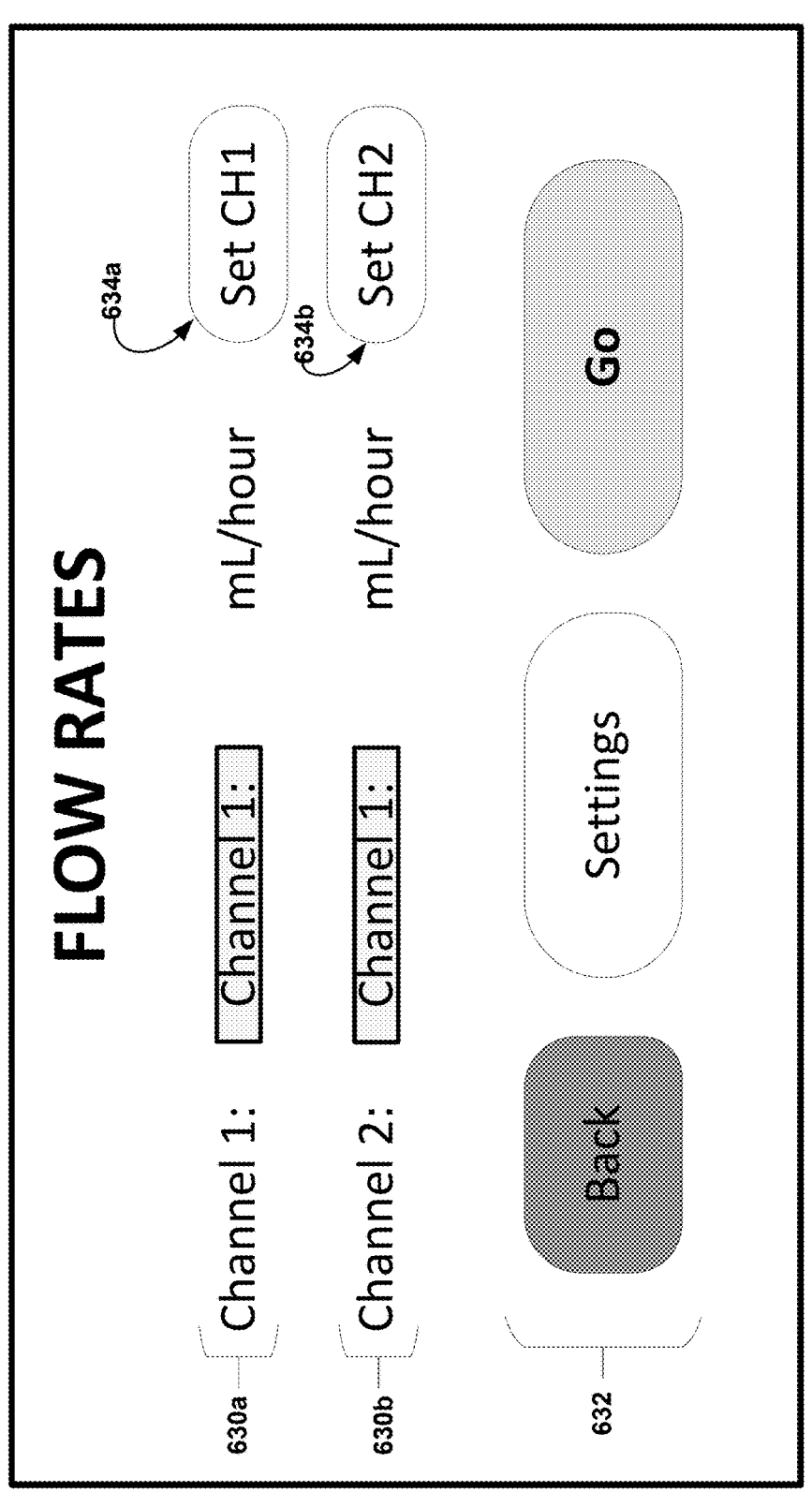
FIG. 6C shows a user interface for the support module of FIGS. 6A-6B.

FIG. 6C shows an example screen for the user interface 620. For example, the screen 620 is configured for setting or monitoring flow rates for a two channel (e.g., two cell chamber) microfluidic chip, such as microfluidic chip 200. The screen 620 shows two readouts 630a-b, one for each respective fluid circuit in the microfluidic chip or microfluidic chips. A control 634a enables control of the flow rate for channel 1, and a control 634b enables flow rate control for channel 2. Additional controls 632 include buttons that allow for navigation between different screens for setting various control parameters or reading different data from different sensors of the one or more microfluidic chips.

Figure 6D:
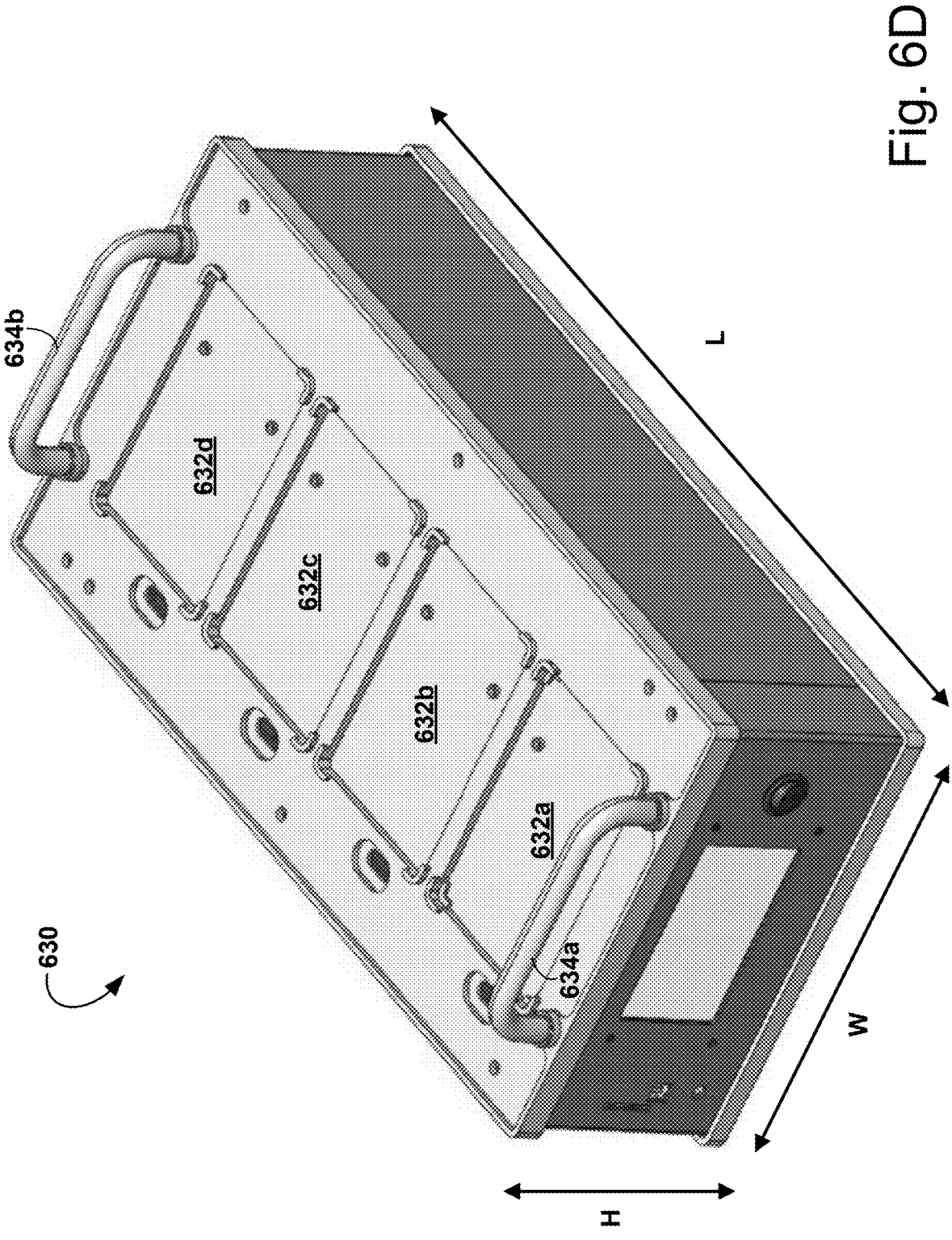
FIG. 6D shows a support module that supports operation of four microfluidic chips.

FIG. 6D shows an example support module 630 configured to support four microfluidic devices. For example, the support module 630 includes four slots 632a-d, each being similar to slot 620. The support module 630 enables parallel, automated control of a plurality of microfluidic devices. For example, a high-throughput test of metabolism of a given drug can be performed on several instances of a microfluidic device in parallel. In some implementations, the support module 630 can support operation of different types of microfluidic devices in parallel. The data generated from each of the microfluidic devices can be stored in a communal memory storage of the support module 630 or in discrete storage associated with a particular slot 632a-d. Handles 634a-b enable transport of the support module 630.

The support module 630 is shown with four slots 634a-d. However, the support module 630 can be scaled up to any number of slots. For example, the support module 630 can include up to twelve slots. Additional slots are also possible, with a constraint being that the support module 630 size be smaller than that of an associated incubator. For example, the four slot support module 630 of FIG. 6D is about 9 inches in width W and 17.7 inches in length L, and 6.3 inches in height H. However, these sizes can be increased to accommodate additional slots. A typical incubator size is 20 inches long, 22 inches wide, and 27 inches in height. The support module 630 can be scaled up within these values. The support module can be larger for larger incubators.

Figure 6E:
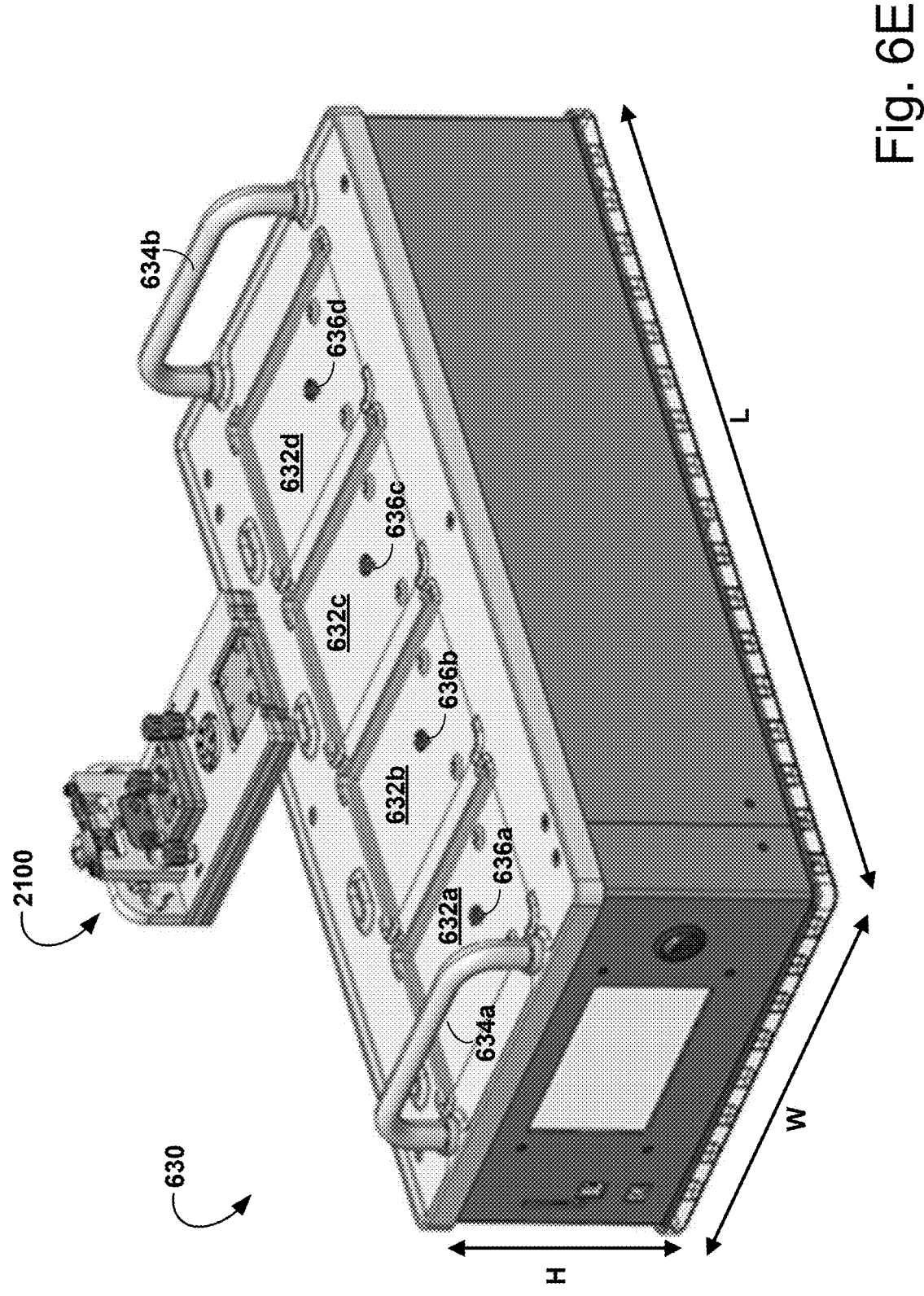
FIG. 6E shows a support module and an example microfluidic chip instance for including on the support module.

FIG. 6E shows an illustration of a perspective view of the support module 630 with an example instance of a microfluidic chip 2100, described in detail in relation to FIGS. 21A-21G below. In some implementations, the microfluidic chip can include microfluidic chip 2000, described in relation to FIGS. 20A-20C below. The microfluidic chip 2100 is configured to interface with the support module 630 in one of slots 632a-d, as described in relation to FIG. 6D. In some implementations, different types of microfluidic chips can be concurrently interfaced with the support module 630 in respective ports 632a-d. These different microfluidic chips can be simultaneously controlled by a controller in the support module 630 for high-throughput experimentation. As previously described, the number of ports can be greater than 4, and can include 8, 12, 16, etc.

Each of the ports 632a-d includes a respective mechanical device 636a-d. The mechanical devices 636a-d can each include a gear or other arm. The mechanical devices 636a-d are each configured to interface with a respective sampling carousel of the microfluidic chip hosted in a given port. A mechanical device 636 rotates the carousel during operation of the microfluidic chip to adjust a sampling chamber position. The mechanical device 636 is controlled by the controller of the support module 630. The controller rotates the sampling carousel during operation of the microfluidic chip to change which sampling chamber is within the fluid loop of the microfluidic chip. The controller can control the position of the sampling carousel by sending a signal to the mechanical device 636 to actuate the mechanical device and rotate the interfaced sampling carousel as needed.

Figures 7A, 7B, 7C:
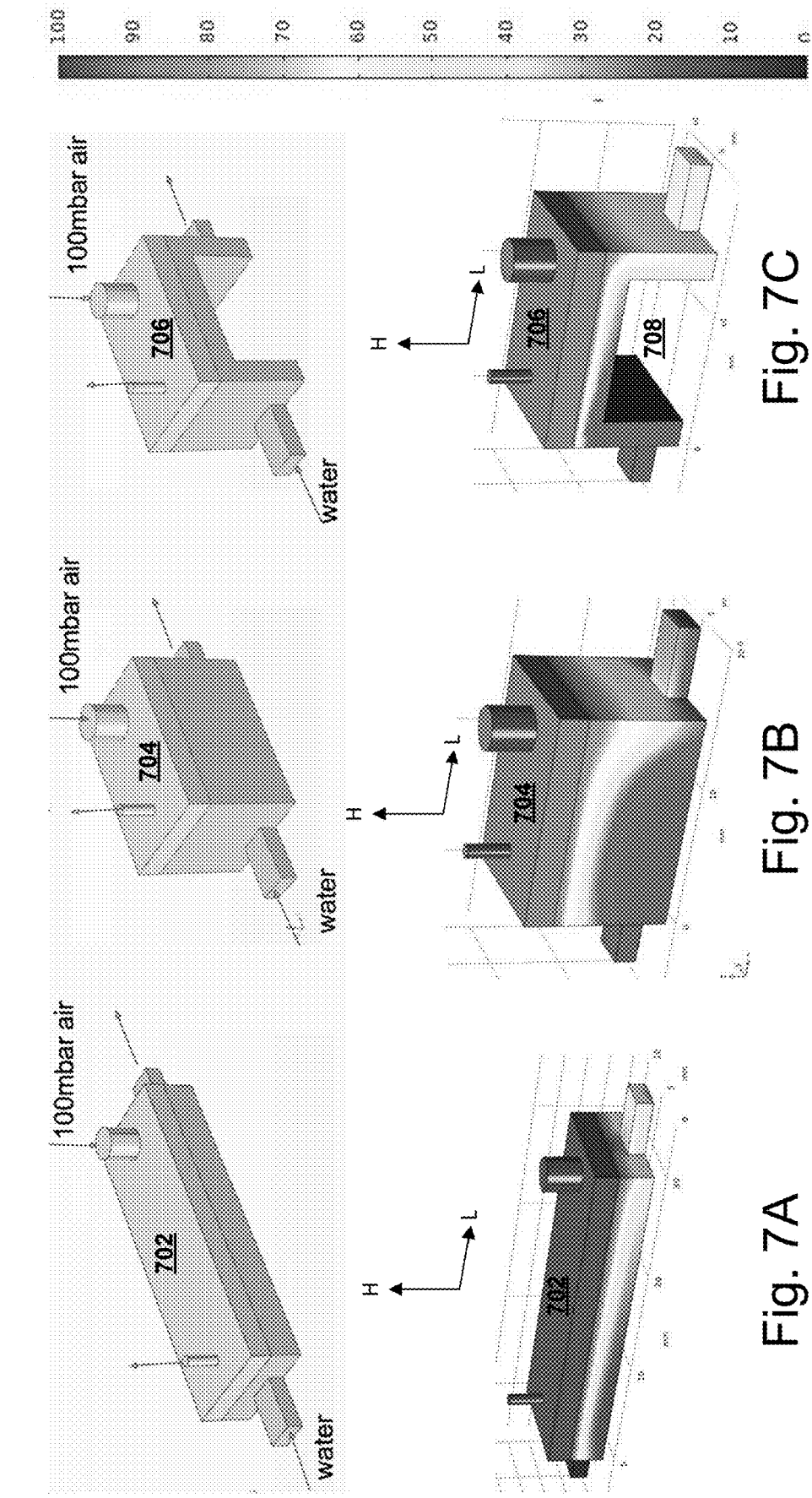
FIGS. 7A, 7B, and 7C each illustrate an example geometry of re-oxygenation chambers for re-oxygenating cell cultures in a recirculating microfluidic chip.

FIGS. 7A, 7B, and 7C each illustrate an example geometry of re-oxygenation chambers 700 for re-oxygenating cell cultures in a recirculating microfluidic chip. The re-oxygenation chambers are configured to perform re-oxygenation of culture media in the recirculating circuit of a microfluidic chip. Different geometries result in different diffusion rates from the air to the fluid medium. CFD modeling is shown in each of FIGS. 7A-7C to show results of simulated rectangular geometries at different flow rates (between 2-8 mL/hour). This shows oxygen exchange efficiency using an inlet air supply including 21% oxygen. The air flow is modelled as an incompressible laminar flow approximation. Diffusion of oxygen in the water is isotropic at $2.75 \times 10^{-9}$ meters per second at 37° C. In these models, there is a fully developed flow at water inlet. Each of devices 7A-7C is shown in a coordinate plane of H=height and L-length.

FIG. 7A shows a re-oxygenation chamber 702 having a long, narrow design. The length is relatively long in comparison to the height (e.g., 3:1 ratio or greater). The relatively long length (L) and short height (H) of re-oxygenation chamber 702 1 is more efficient at exchanging oxygen than a relatively short length and larger height of re-oxygenation chamber 704 of FIG. 7B. For example, re-oxygenation chamber 702 has an oxygen concentration of 51% DO, while re-oxygenation chamber 704 has an exit oxygen concentration of 13% DO.

FIG. 7C shows a re-oxygenation chamber 706 with a relatively short length L and relatively larger height H (e.g., ~2:3 ratio). Re-oxygenation chamber 706 has a redistribution cutout 708 that improves re-oxygenation efficiency from the re-oxygenation chamber 704 with a shorter design, having an exit oxygen concentration of 42% DO. To further increase exit oxygen concentration, complex geometries can be used, such as serpentine geometries.

Figure 8A:
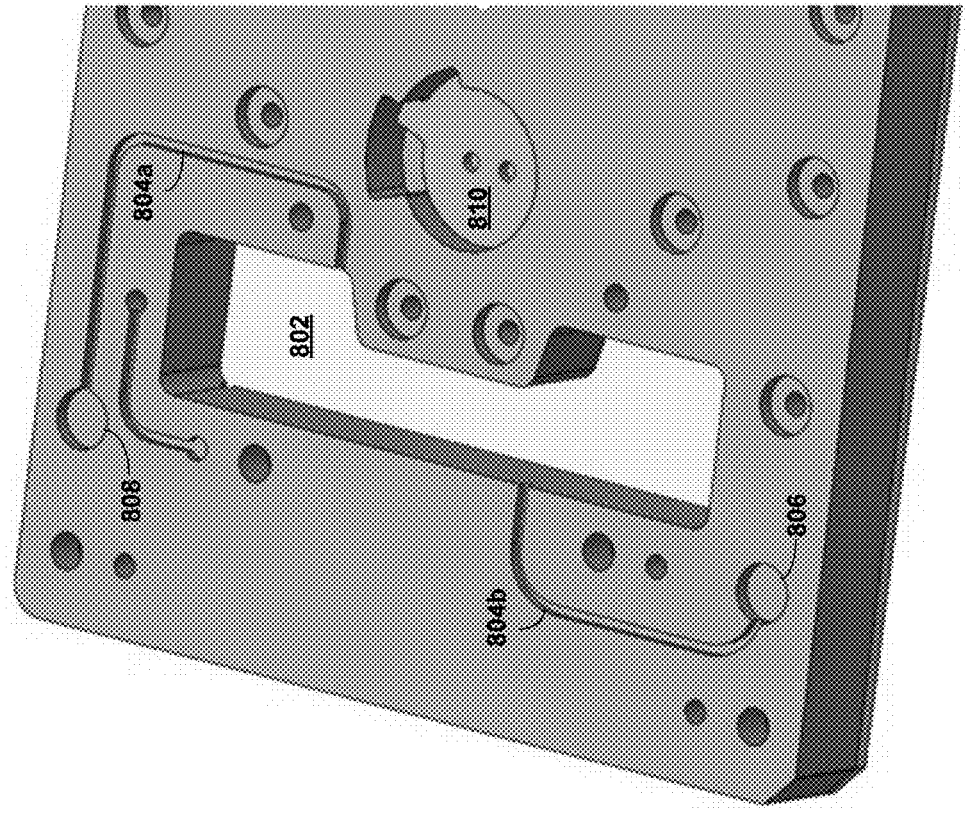
FIGS. 8A-8B each illustrate perspective views of example oxygenation compartments for a recirculating microfluidic chip.
Figure 8A:
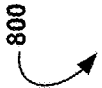
Figure 8B:
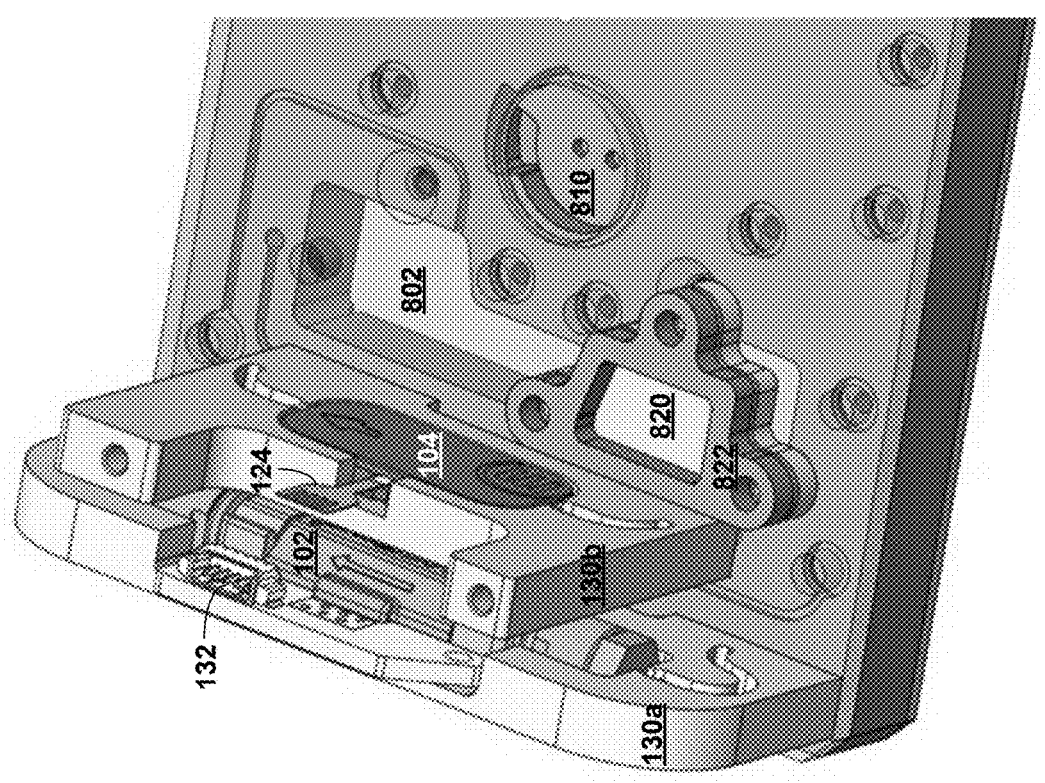
Figure 8B:
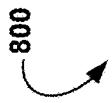

FIGS. 8A-8B each illustrate perspective views of example re-oxygenation chambers (also called oxygenation compartments) for a recirculating microfluidic chip. FIG. 8A shows a portion of a microfluidic chip 800 with the re-oxygenation chamber 802. The microfluidic chip 800 has an air input path 804b from air input port 806, and an air output path 804a from air output port 808. The valve 810 can be similar to valve 114 of FIG. 1A. The re-oxygenation chamber 802 is cut from the substrate of the microfluidic chip 800. In some implementations, the air channels 804*a-b* introduce lab-mixed gas having a composition of 5% $CO_2$, 21% $O_2$, and 74% $N_2$ to oxygenate media in the re-oxygenation chamber 802.

FIG. 8B shows a perspective view of the re-oxygenation chamber 802 with other components of the microfluidic chip 800 shown, such as the pump 104, the flow sensor 102, housings 130*a-b*, and control ports 124, 132. The microfluidic chip 800 has an oxygen permeable membrane 820 that is coupled to the re-oxygenation chamber 802 with a clamp 822. Rather than introducing air from the ports 806, 808, air from the atmosphere contacts the permeable membrane 820. Oxygen is allowed into the re-oxygenation chamber 802 to allow oxygen into the chamber.

Figure 9:
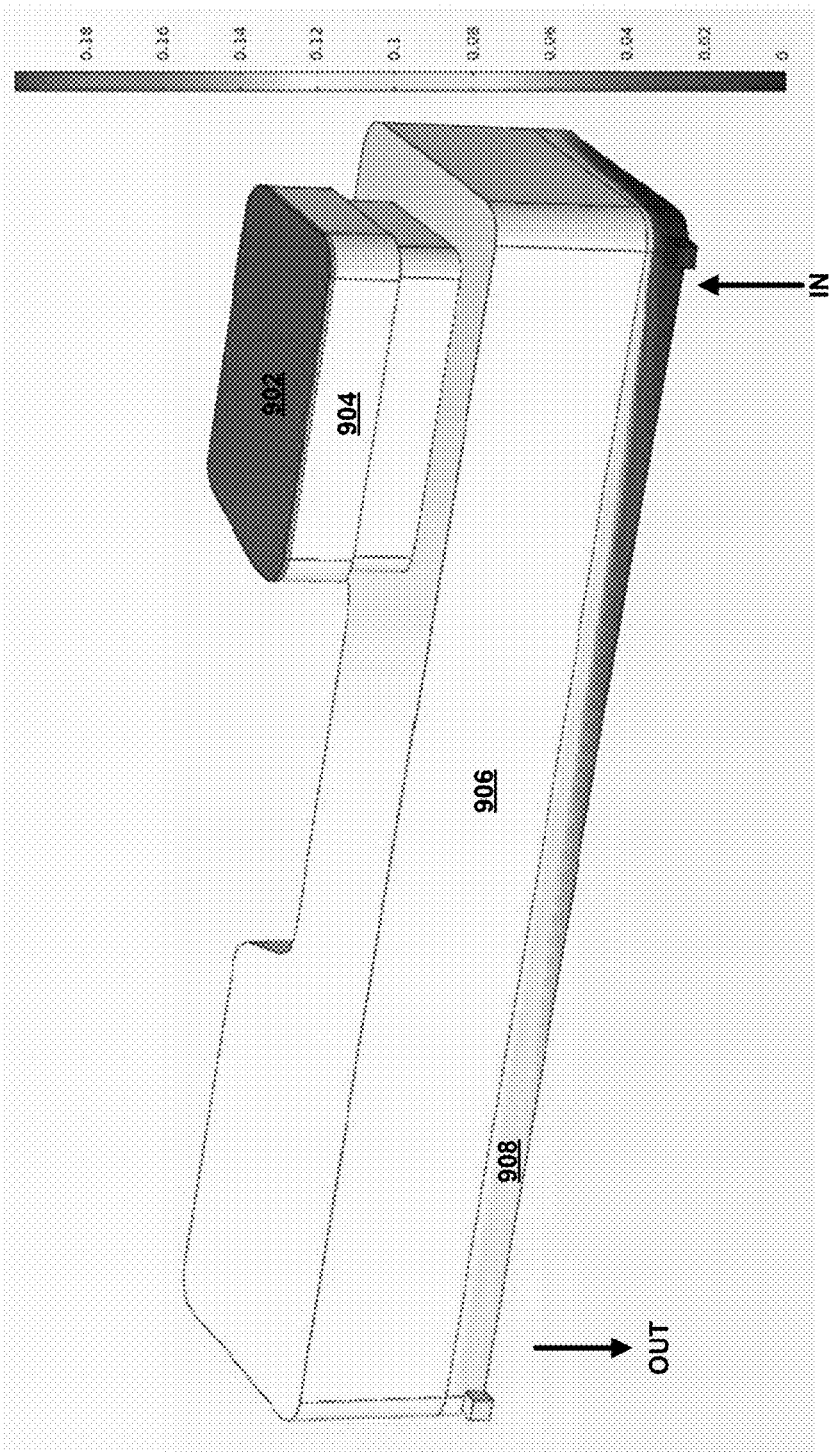
FIG. 9 shows a perspective view of the example oxygenation compartment of FIGS. 8A-8B.

FIG. 9 shows a perspective view of the example oxygenation compartment 900, similar to re-oxygenation chamber 802 of FIGS. 8A-8B. Specifically, FIG. 9 shows a computational fluid dynamics model of oxygen diffusion into the re-oxygenation chamber The re-oxygenation chamber 900 includes a portion 906 filled with air, and a portion 908 filled with fluid medium from the fluid circuit. The oxygen concentration increases from right to left as the medium moves from the input to the output ports. Air enters the re-oxygenation chamber 900 through the membrane 902 and through passage 904. Because the membrane allows oxygen into the chamber, the air 906 above the media 908 reaches an oxygen concentration of ~67% and is well distributed in the chamber. The media oxygen gradient increases from almost no oxygen in the oxygen depleted medium from the cell chamber to about 47% out from the re-oxygenation chamber 900.

Figures 10A, 10B:
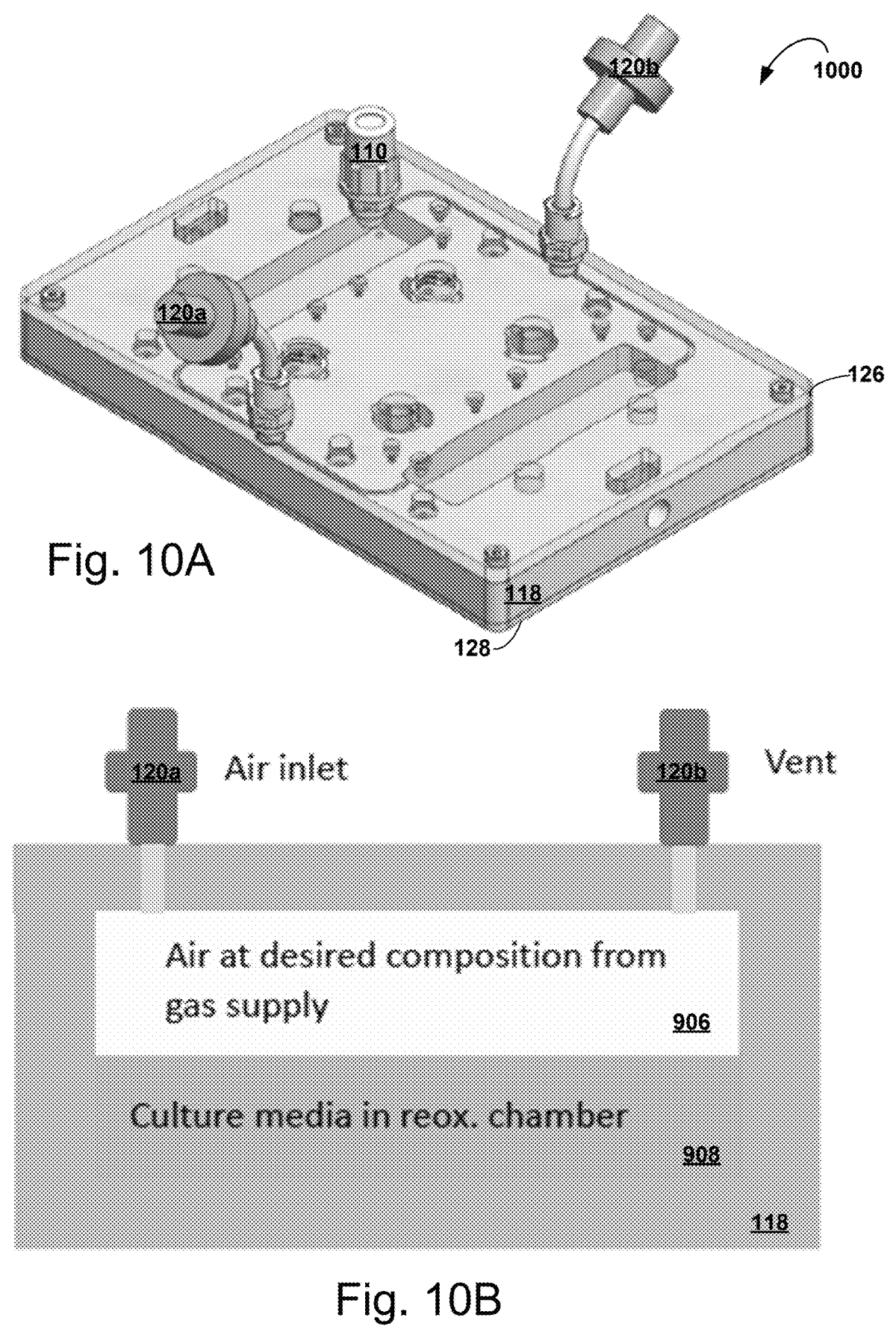
Figures 10C, 10D:
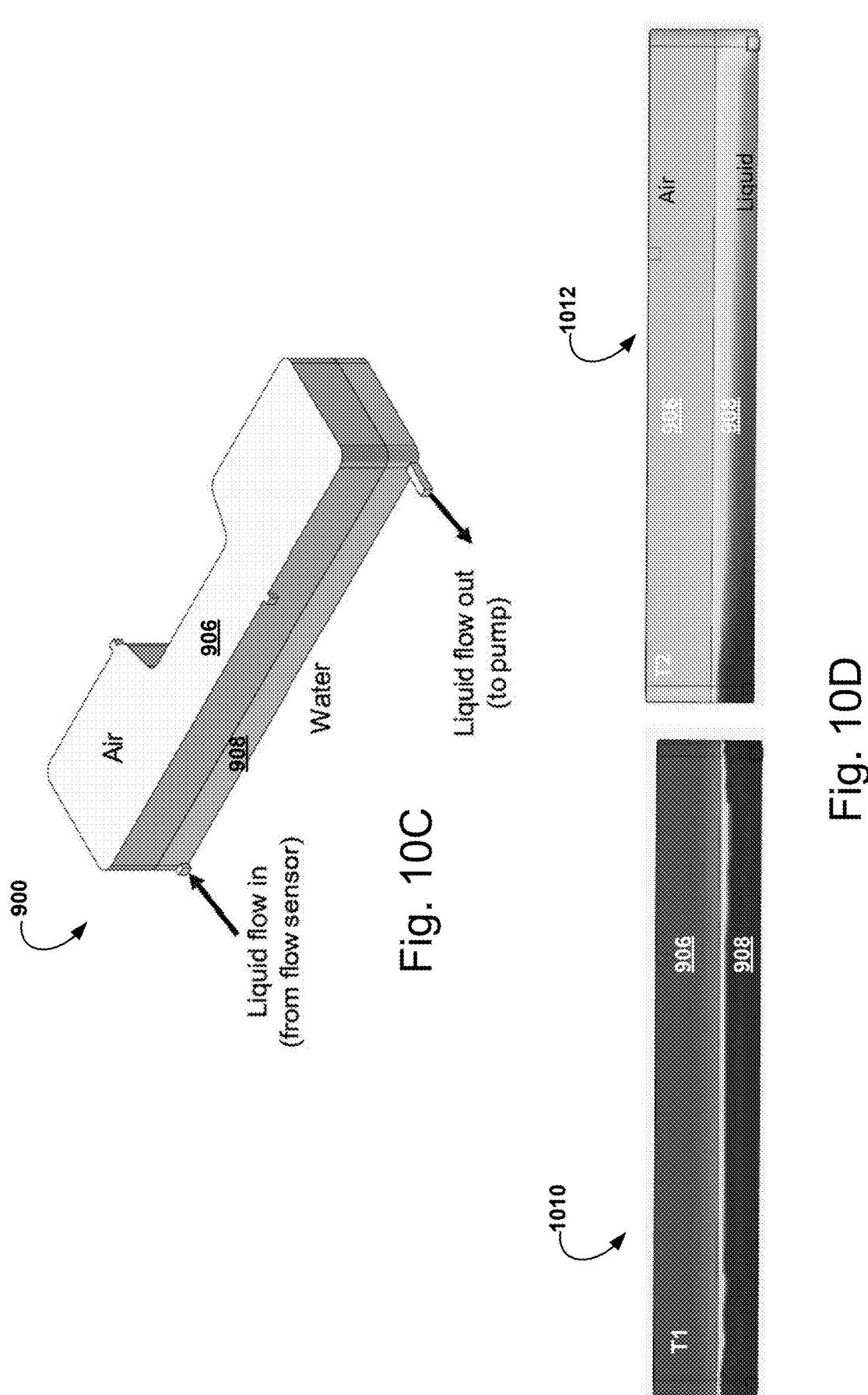
FIGS. 10C and 10D each show an illustrations of CFDs of an example re-oxygenation chamber for the recirculating microfluidic chip.

FIGS. 10A and 10B each show an illustration of an example of a recirculating microfluidic chip 1000 for testing the re-oxygenation chamber 900 of FIG. 900. FIGS. 10C and 10D each show an illustrations of CFDs of an example re-oxygenation chamber 900 for the re-oxygenation chamber of the microfluidic chip. The re-oxygenation chamber 900 is filled to an initial volume of about 2 mL (~2 mm fluid depth). The air pressure of region 906 is about 10 mBar.

The design of the re-oxygenation chamber 900 is based on the following design parameters. The re-oxygenation chamber 900 air turnover rate can be adjusted. Increasing the air turnover rate increases the oxygen content delivered to the cells in the cell chamber. The initial oxygen content in the air can be adjusted. Increasing the initial value increases the oxygen content delivered to the cells. Various custom air mixes are possible to control an amount of oxygen in the re-oxygenation chamber air. A volume of the liquid or fluid medium in the re-oxygenation chamber can be adjusted. The volume affects a liquid height and air volume in the re-oxygenation chamber 900, affecting re-oxygenation rate. Decreasing the volume generally increases the oxygen content delivered to the cells. The liquid flow rate can be adjusted. Decreasing the flow rate increases the oxygen content delivered to the cells by the medium. Generally, the liquid flow rate is determined based on cell zonation and shear requirements previously described, rather than re-oxygenation chamber operation. The oxygen content at the air inlet can be adjusted. The re-oxygenation chamber 900 geometry can be adjusted. Each of these can be used to tune the amount of oxygen supplied to the cell chamber.

The re-oxygenation chamber 900 CFDs of FIG. 10D show a first CFD 1010 at a first time T1 and a second CFD 1012 at a second time T2 later than T1. At time T1, there is no gradient of oxygen in the re-oxygenation chamber 900. At time T2 there is a gradient of oxygen in the re-oxygenation chamber 900. The CFDs are used to model oxygen concentration in the air volume, liquid volume, and outlet of the re-oxygenation chamber and its movement via diffusion and liquid flow over time.

FIGS. 11A, 11B, and 11C each show representations of oxygen consumption in a re-oxygenation chamber of a microfluidic chip. Generally, differential biosynthesis or biotransformation is a function of liver lobule localization. The microfluidic chip can be used for testing phase I enzymes and phase II enzymes. Phase I enzymes often catalyze oxidation, reduction, and hydrolysis reactions. Most phase II enzymes catalyze conjugation reactions: UDP-glucuronosyltransferases (UGTs), sulfotransferases (SULTs), or glutathione S-transferases (GSTs). Drugs are often metabolized by sequential reactions involving phase I and II enzymes. The microfluidic chip can also be designed for emulating gluconeogenesis (GNG) is a metabolic pathway that results in the generation of glucose from certain non-carbohydrate carbon substrates. The microfluidic chip can be configured to emulate bile acid and fatty acid metabolism. The microfluidic chip is designed to establish an oxygen gradient for emulation of emulation of zonal oxygen gradient for in vitro human liver tissue culture.

In a human, the liver has three different zones. Each zone has distinctive characteristics (enzyme expression levels (CYPs, UGTs), metabolic activity (glycolysis, gluconeogenesis, bile acid synthesis etc.). One of the major drivers of the zonation is the oxygen tension between periportal (pp) and perivenous (pv) regions. The microfluidic chips described herein can be configured to emulate oxygen tension, similar to the liver zonation, to derive differential zones on chips. This functionalizes the tissue similar to in vivo, such as CYP and UGT activities for PK testing, metabolic activities (abnormalities) to study human diseases.

Figures 12A, 12B, 12D:
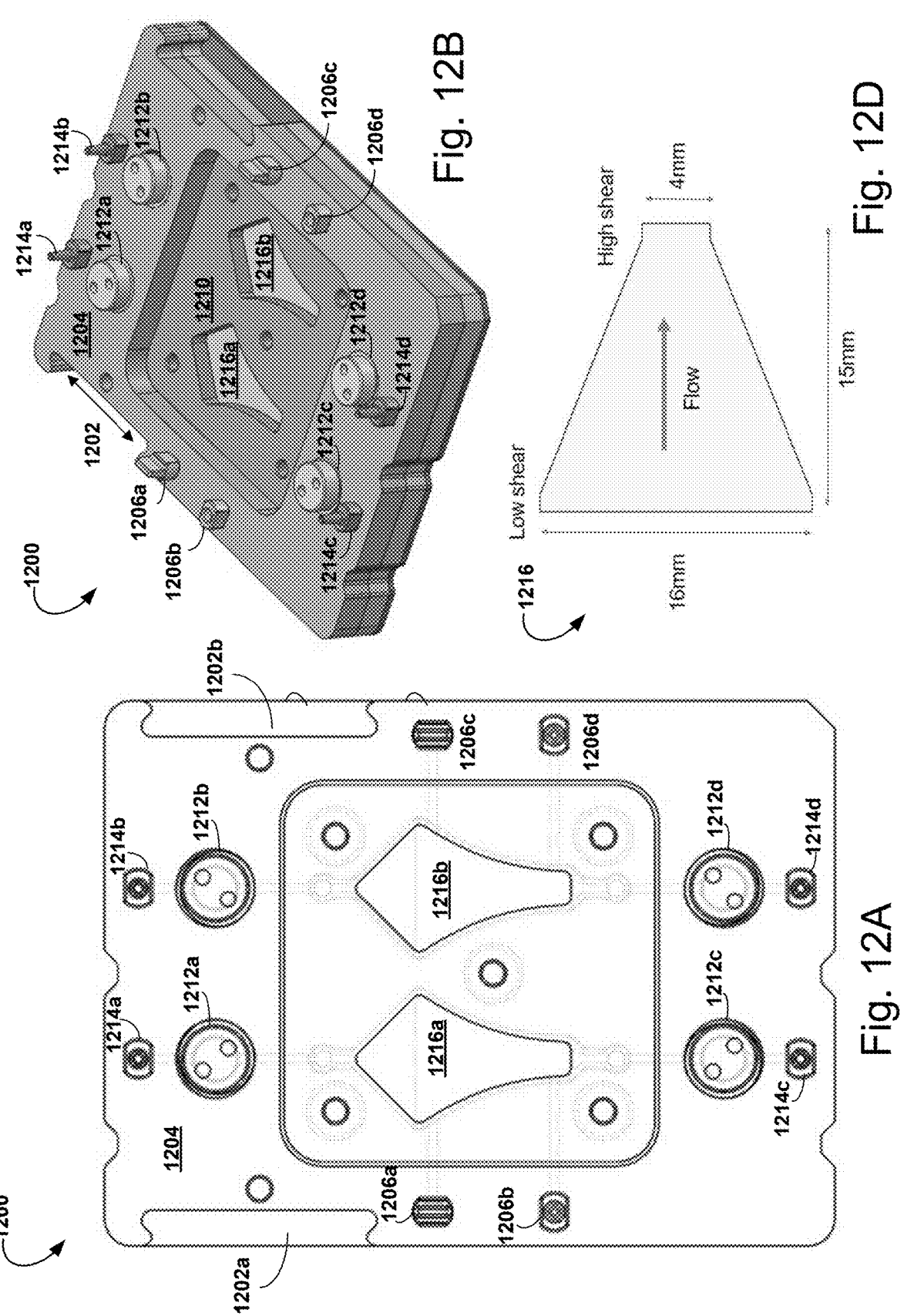
FIG. 12A shows a top view of a microfluidic chip for determining an optimal shear rate.
FIG. 12B shows a perspective view of the microfluidic chip of FIG. 12A.
FIG. 12D shows a diagram of the cell chambers of microfluidic chip.
Figure 12C:
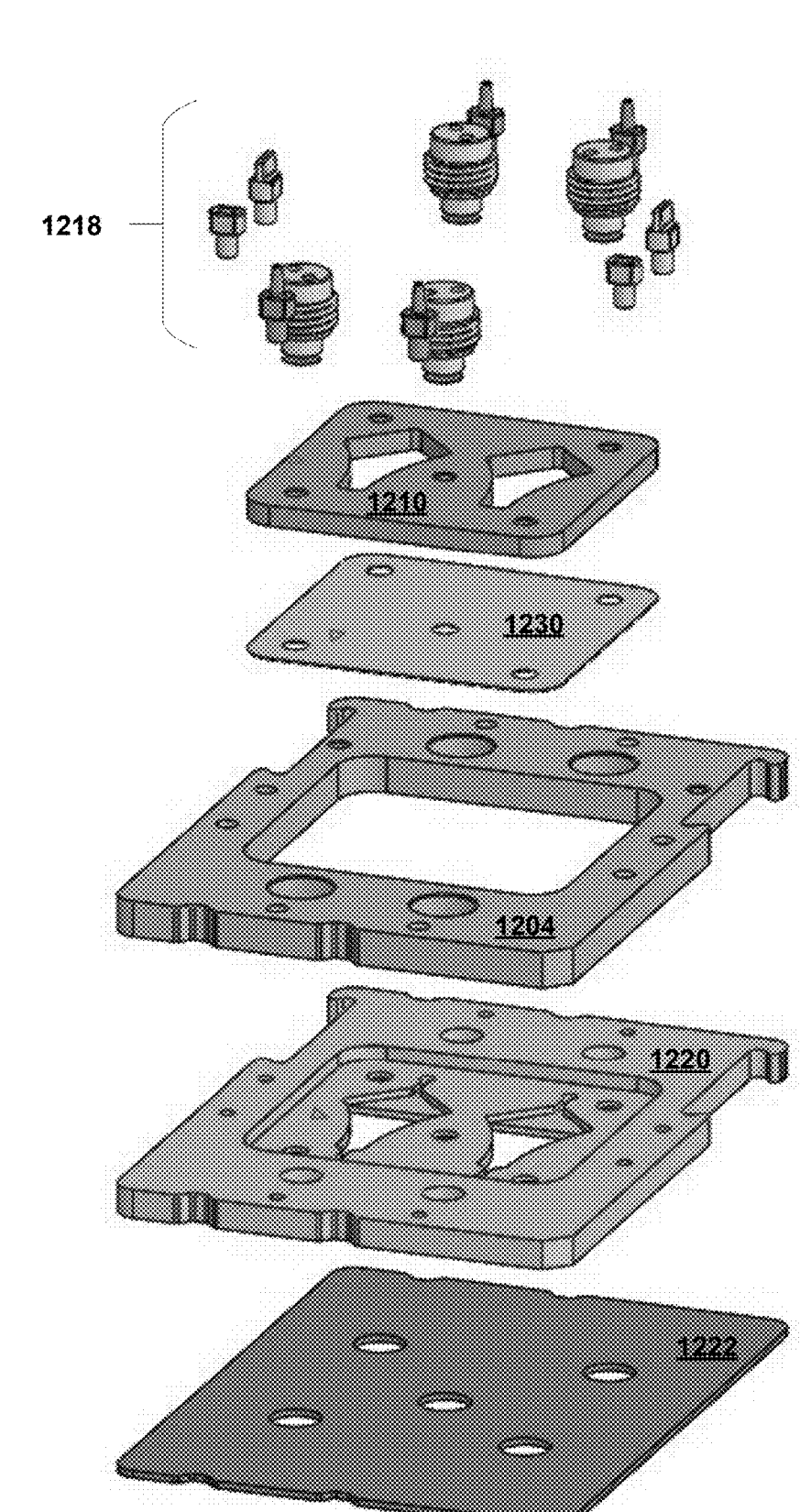
FIG. 12C shows an exploded view of the microfluidic chip of FIGS. 12A-12B.

FIG. 12A shows a top view of a microfluidic chip 1200 configured for determining an optimal shear rate for the cell chambers. FIG. 12B shows a perspective view of the microfluidic chip of FIG. 12A. FIG. 12C shows an exploded view of the microfluidic chip of FIGS. 12A-12B. FIG. 12D shows a diagram of the cell chambers of microfluidic chip 1200. The microfluidic chip 1200 is a test bed for testing chamber geometries, and can also be a modular unit (also called an insert) for including different cell chambers in a recirculating loop, such as that for microfluidic chips 100, 200, etc. as previously described.

The microfluidic chip 1200 of FIGS. 12A-12D includes modular pump mounts 1202*a-b* on each side of the microfluidic chip substrate 1204. The microfluidic chip 1200 includes inlet ports 1214*a-b* and exit ports 1214*c-d*. Ports 1214*a-d* are for flow of the fluid medium through the cell chambers 1216*a-b* for a recirculating fluid loop. The ports 1206*a-b* are seeding an waste ports for chamber 1216*a*, and ports 1206*c-d* are seeding and waste ports for chamber 1216*b*. Each chamber 1216*a*, 1216*b* is associated in the fluid flow path with an inlet oxygen concentration sensor 1212*a*, 1212*b*, respectively. Each chamber 1216*a*, 1216*b* is associated in the fluid flow path with an outlet oxygen concentration sensor 1212*c*, 1212*d*, respectively.

FIG. 12C shows an example exploded view of the layers of microfluidic chip 1200. Ports 1218 interface with a substrate layer 1204. A clamp layer 1210 fastens the oxygen permeable membrane 1230 of the cell chambers 1216*a-b* to the substrate layer 1204. A geometry of the cell chambers 1216*a-b* is formed by the cell substrate layer 1220. This can be shaped to shape the cavities inside the cell chamber 1216*a-b* to test various shear outcomes for different geometries. A bottom layer 1222 forms a cover for the microfluidic chip 1200.

The microfluidic chip 1200 platform enables various geometries of the cell chambers 1216*a-b* to be tested and operated in parallel. The microfluidic chip 1200 can be used to test a range of shear stresses in one channel to observe the effect of shear on PHH and determine the optimum shear range. FIG. 12D shows an example geometry of a chamber such as cell chambers 1216*a-b*. Generally, for microfluidic chip 1200, the chamber can be oxygenated through an oxygen-permeable membrane to isolate shear as a variable and provide sufficient oxygen during seeding. Generally, shear increases by a factor of 4 along the length of chamber 1216*a-b*. In some implementations, flow rate can be adjusted to test different shear ranges (e.g., a linear relationship).

Example cell chamber dimensions are now described. In some implementations, the cell chamber channel total height is 3 mm. In some implementations, the surface area of well is 1 cm². In some implementations, the cell chamber total height is 2 mm. Examples of specific dimensions are provided in Table 1.

TABLE 1

| Example Dimensions for a single channel of microfluidic chip 1200 | | | | |
| --- | --- | --- | --- | --- |
| Category | Surface Area [mm^2] | Height [mm] | Volume (mm^3) | Volume (mL) |
| Cell Channel (Waterfall bottom and Above) | 152.00 | 2.00 | 304.00 | 0.30 |
| Cell Channel (Waterfall Tops) | 101.40 | 1.00 | 101.40 | 0.10 |
| Paths | 41.74 | 1.00 | 41.74 | 0.04 |
| Inlet/Exit Ports | N/A | N/A | 80.11 | 0.08 |
| Total Flowing | 295.14 | Variable | 527.25 | 0.53 |
| Seeding Paths | 23.20 | 1.00 | 23.20 | 0.02 |
| Seeding Ports | N/A | N/A | 111.21 | 0.11 |
| Total Dead | | | 134.41 | 0.13 |
| Total Volume | | | 661.66 | 0.66 |

Figures 13A, 13B:
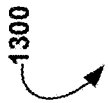
FIGS. 13A-13B each show an illustration of an example waterfall configuration of a cell chamber channel in a microfluidic chip for reducing shear rate on cells in the chamber by a fluid flow in the fluid loop.

FIGS. 13A-13B each show an illustration of an example cell chamber wall 1300 geometry in microfluidic chip 1200 of FIGS. 12A-12D for reducing shear rate. The wall 1300 forms a surface over which the fluid medium flows during microfluidic chip 1200 operation. As shown in the CFD of FIG. 13B, the wall has a low shear rate. For example, the wall 1300 has a waterfall geometry. The waterfall (or step) geometry reduces shear and maximizes oxygenation of the cells in the cell chamber 1216*a-b*. The cells are on the bottom surface 1302 of the wall. The location of the cells in the chamber 1216*a-b* are controlled to live in a specified area due to gravity. The taper 1304 in the chamber channel increases the shear along the length of the cell chamber. For this configuration, at any flow rate more than 1 mL per hour through the chamber 1216*a-b*, oxygen is present in every area of the cell channel.

Figure 13C:
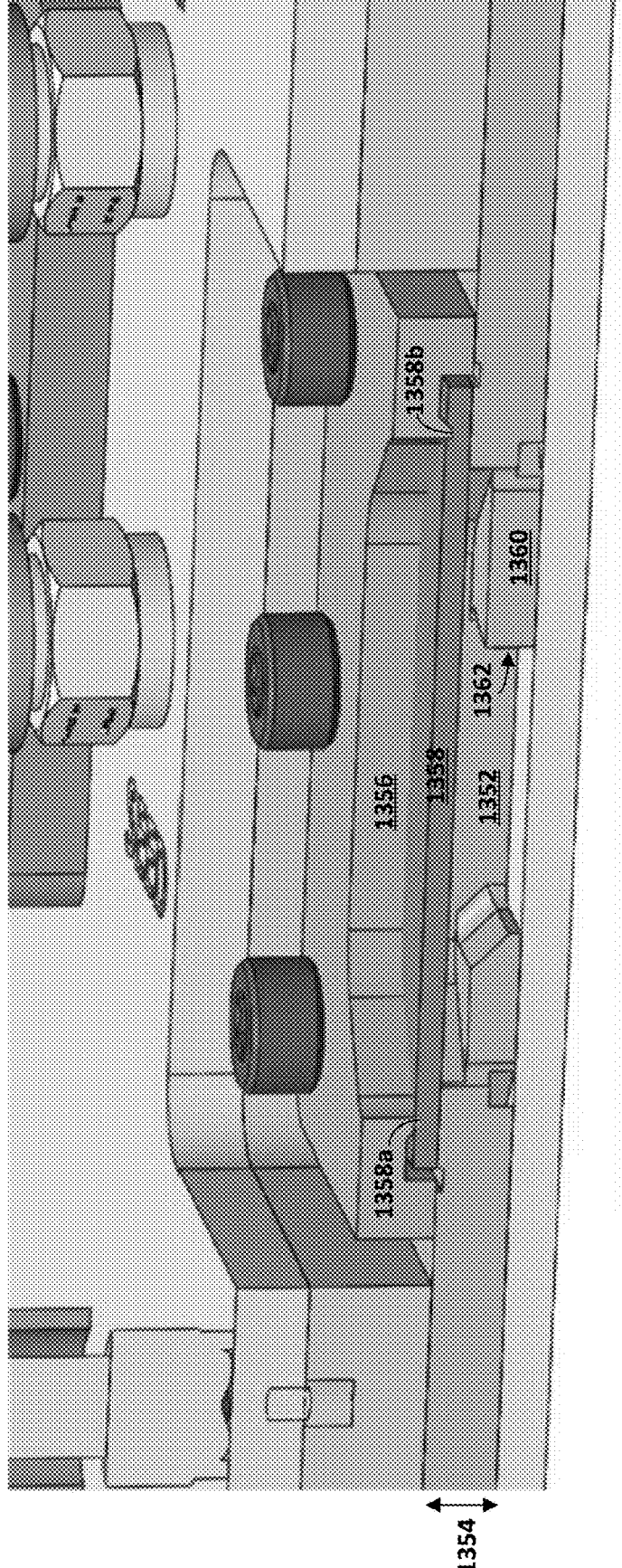
FIG. 13C shows an example of a portion of an MPS chip including a cell chamber channel having a waterfall geometry in a cell chamber insert.

FIG. 13C shows an example of an insert portion 1350 of a microfluidic chip including a cell chamber channel having a waterfall geometry as shown in FIGS. 13A-B. The cell chamber wall 1300 is in the channel 1352 of the cell chamber. The cell chamber wall layer 1354 is formed into the waterfall geometry within the channel 1352. A cover 1356 holds a membrane 1358 in place over the channel 1352. The membrane 1358 is seeded with a tissue, such as a liver tissue, muscle tissue, kidney tissue, etc. The cover 1356 holds the membrane 1358 in tension over the channel 1352, such as by notches 1358*a-b*. The thickness of the cell chamber wall layer 1354 determines a thickness of the cell chamber channel 1352 and a height of a wall 1362 of the waterfall feature 1360. In some implementations, the wall

1362 is 1 mm high. In some implementations, the wall 1362 is 2 mm high. In some implementations, the wall 1362 is between 1 mm-2 mm high.

Figures 14A, 14B, 14C:
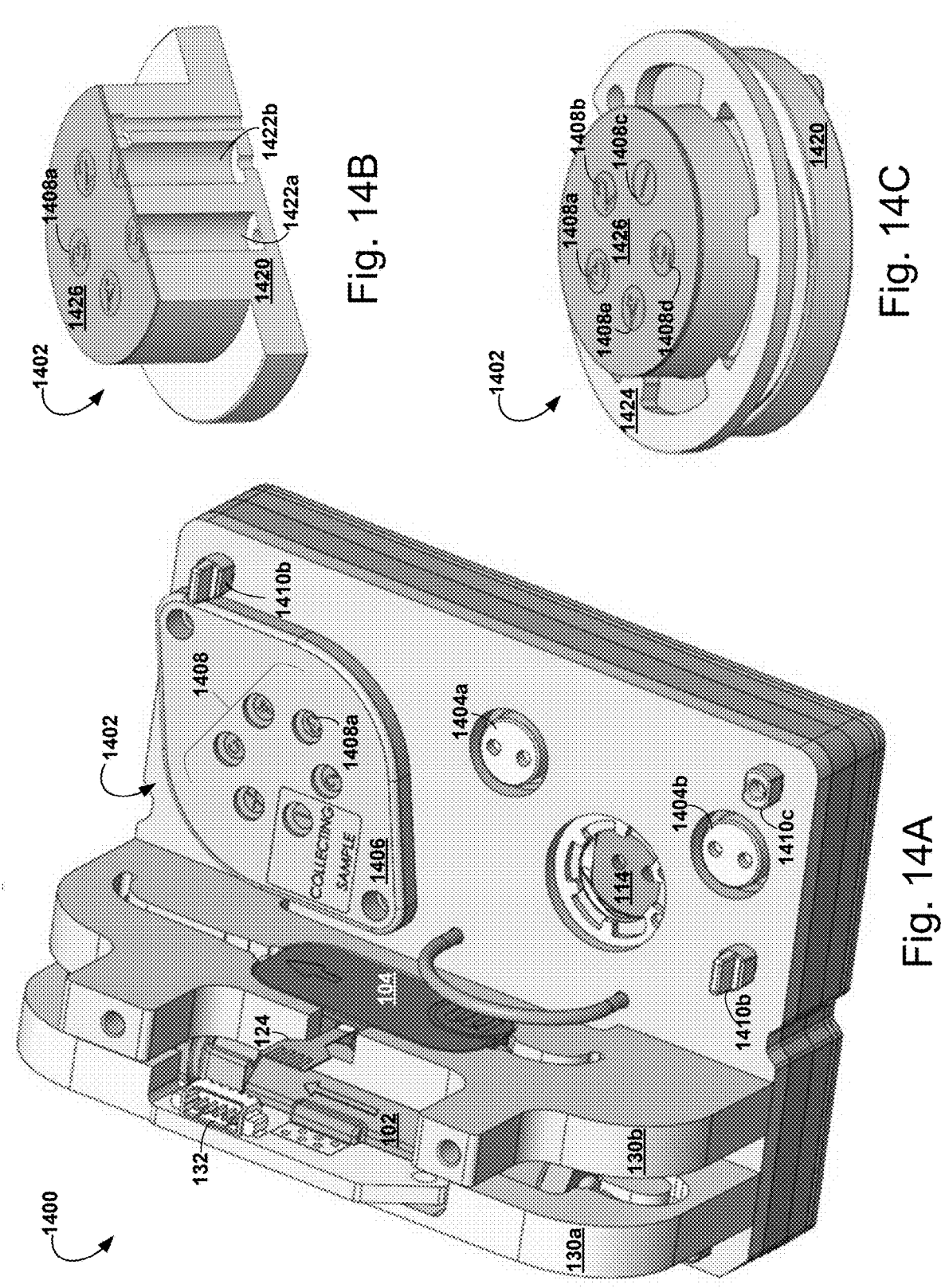
FIG. 14A show an example microfluidic chip including a sample carousel for sampling fluid medium from the microfluidic chip.
FIGS. 14B, 14C, and 14D each show a perspective view of the sample carousel of FIG. 14A, or portions thereof.
Figure 14D:
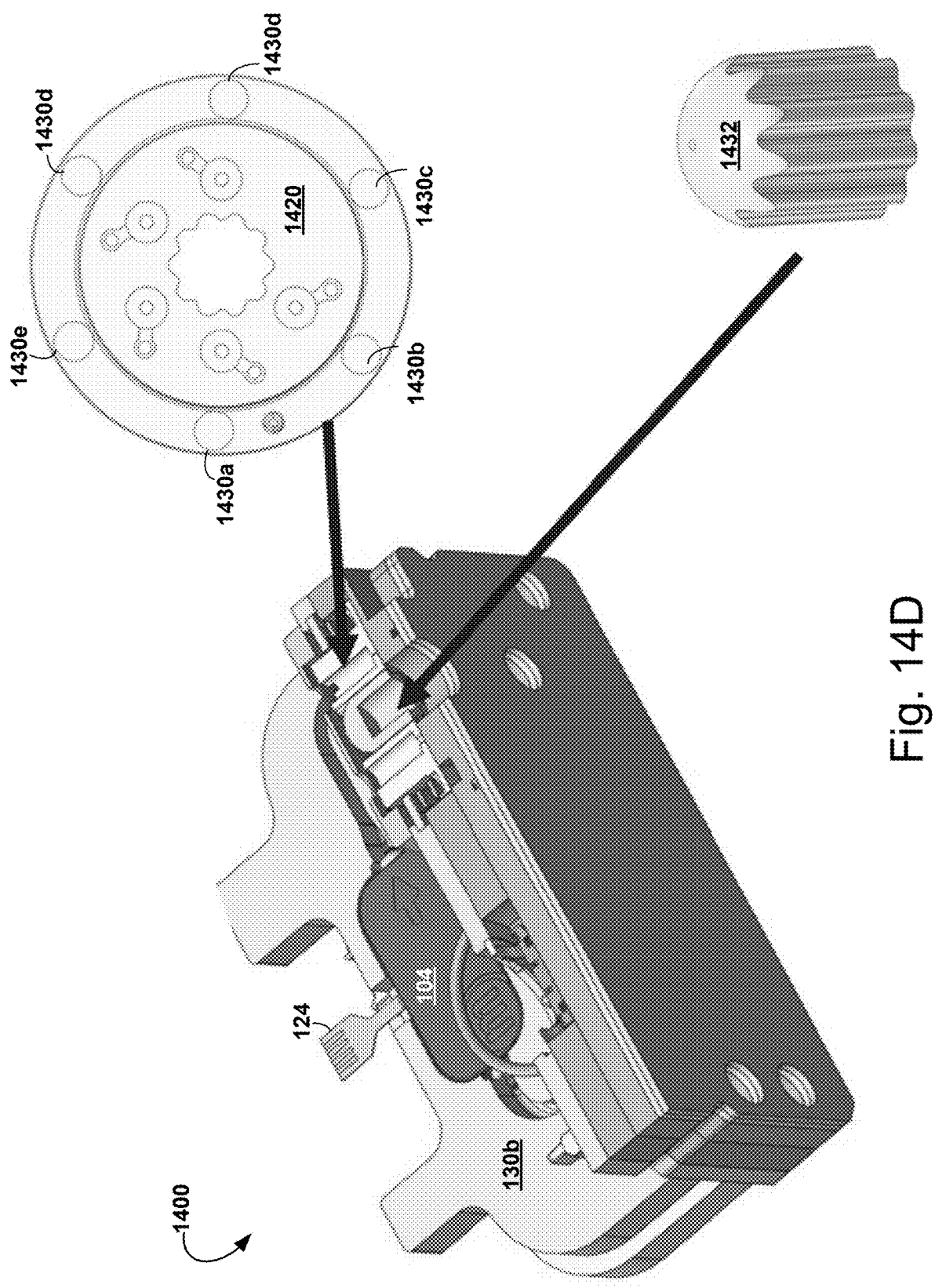

FIG. 14A show an example microfluidic chip 1400 including a sample carousel 1402 for sampling fluid medium from the microfluidic chip 1400. FIGS. 14B, 14C, and 14D each show a perspective view of the sample carousel of FIG. 14A, or portions thereof. microfluidic chip 1400 includes the pump 104, flow sensor 102, and substrate layers as described previously for microfluidic chips 100, 200, etc. herein. Input and output ports 1410*a-b* are visible from the perspective top view of the microfluidic chip 1400. Oxygen concentration sensors 1404*a-b* are accessible from the top of the microfluidic chip 1400.

The sample carousel 1402 of the microfluidic chip 1400 is configured to house a plurality of sample chambers 1408 (also called vials). In some implementations, the number of sample chambers 1408 can vary, but for this example, five chambers 1408*a-e* are shown. The carousel is configured to be controlled by the controller of support module 600. A cover 1406 prevents manual rotation of the carousel. Each chamber 1408*a-e* is stamped with a number so that samples can be tracked once removed from the carousel.

The controller is configured to rotate the carousel base 1420 to collect an additional sample of fluid medium. Each chamber volume (e.g., volumes 1422*a-b*) in the base 1420 holds several μL of fluid. When the carousel rotates, a new chamber 1408 is put in the fluid flow path for collecting fluid. A heat sealed foil cover can seal the chambers 1408 to prevent leaks of the fluid circuit to the outside environment. The controller is configured to rotate the base 1420 by sensing a position of the base 1420 using magnets 1430*a-e* corresponding to the chamber 1408*a-e* locations. A stepper motor pinion 1432 is incremented by the controller to rotate the base to position a new chamber 1408*a-e* in the flow path. Holes in the cover 1406 allow any sample to be extracted from the carousel 1402.

Figure 15A:
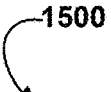
FIGS. 15A-15B each show an illustration of an example microfluidic chip including an integrated fluid valve device.
Figure 15B:
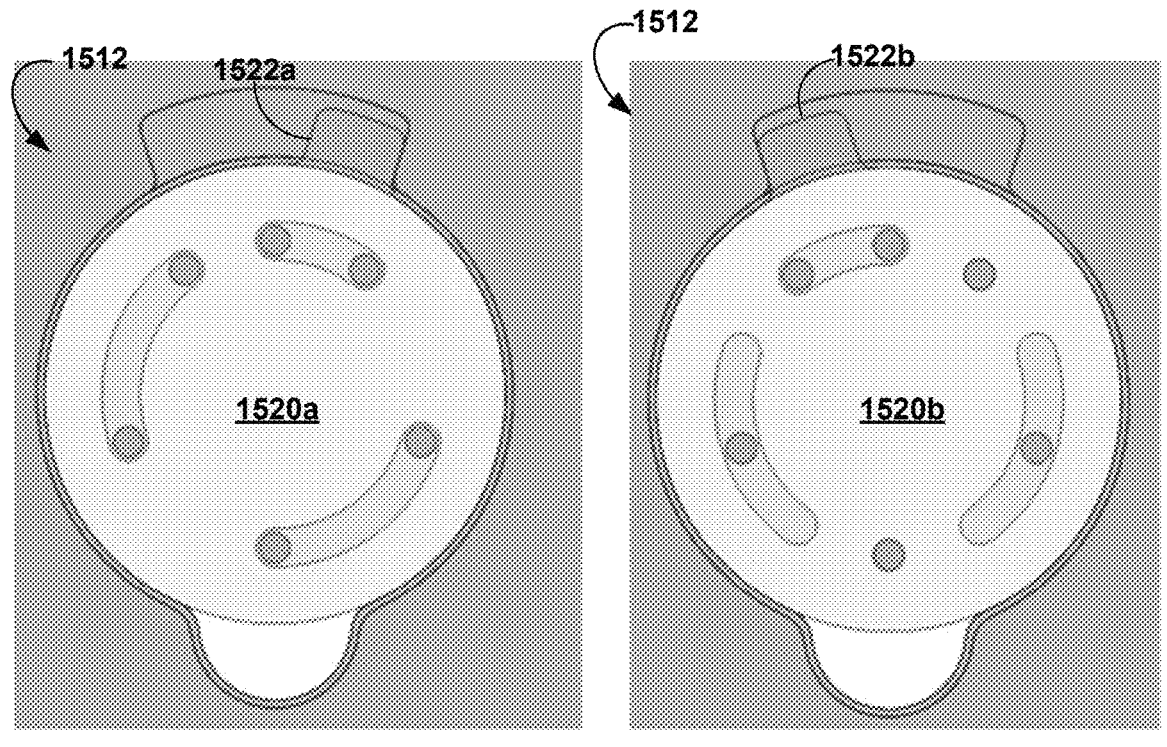
Figure 15B:
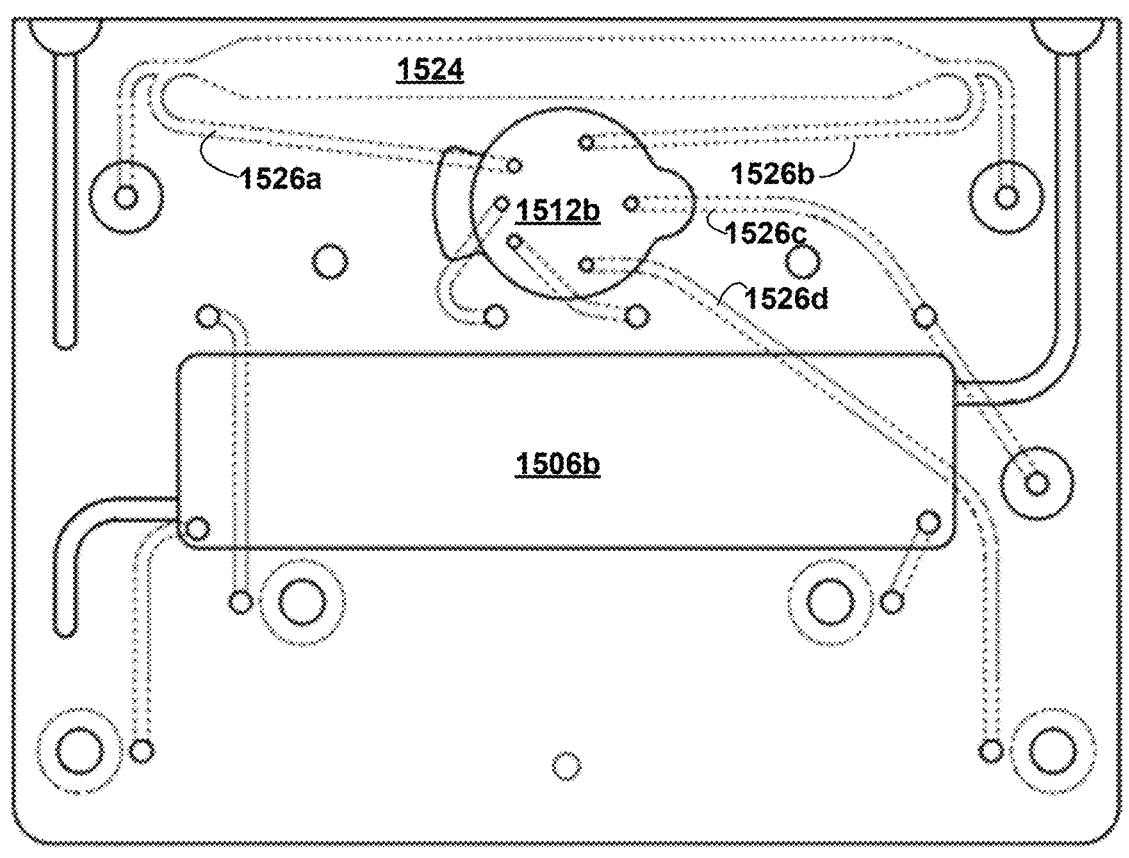

FIGS. 15A-15B each show an illustration of an example microfluidic chip 1500 including an integrated fluid valve device. Similar to microfluidic chip 200, microfluidic chip 1500 includes two fluid circuits for re-oxygenation of the fluid medium for passing through two cell chambers 1506*a-b*. The microfluidic chip 1500 includes two pumps 1504*a-b*, flow sensors 1502*a-b*, housings 130*a-d*, cell sampling ports 1510*a-b*, flow paths 1508*a-d* and 1514*a-b*, and re-oxygenation chambers 1506*a-b*.

The microfluidic chip 1500 includes valves 1512*a-b* with rotating portions 1518*a-b*. Valves 1512*a-b* are shown in greater detail in FIG. 15B. The valves 1512*a-b* are configured to move from a first position 1520a to a second position 1520b to enable fluid flow or prevent fluid flow. The valve 1512b, for example, is configured to allow fluid flow between the re-oxygenation chamber 1506b and the cell chamber 1524. Flow paths 1526a and 1526b flow from the cell chamber 1524 to the valve. When the valve is open, fluid flows through the circuit. When the valve is closed, fluid does not flow through the circuit. The valve 1520b can isolate the cell chamber 1524 and switch between seeding and recirculation modes. The valve 1512 is incorporated into the fabricated chip. To simplify user experience and reduce a number of separate valves, the valve 1512 includes three sub-valves for isolation of fluid circuit portions such as the re-oxygenation chamber 1506b and the cell chamber 1524. There are two valve positions including a normal flow (e.g., I or 1520a) and a second position 1520b (O or seeding & flushing).

Figures 16A, 16B:
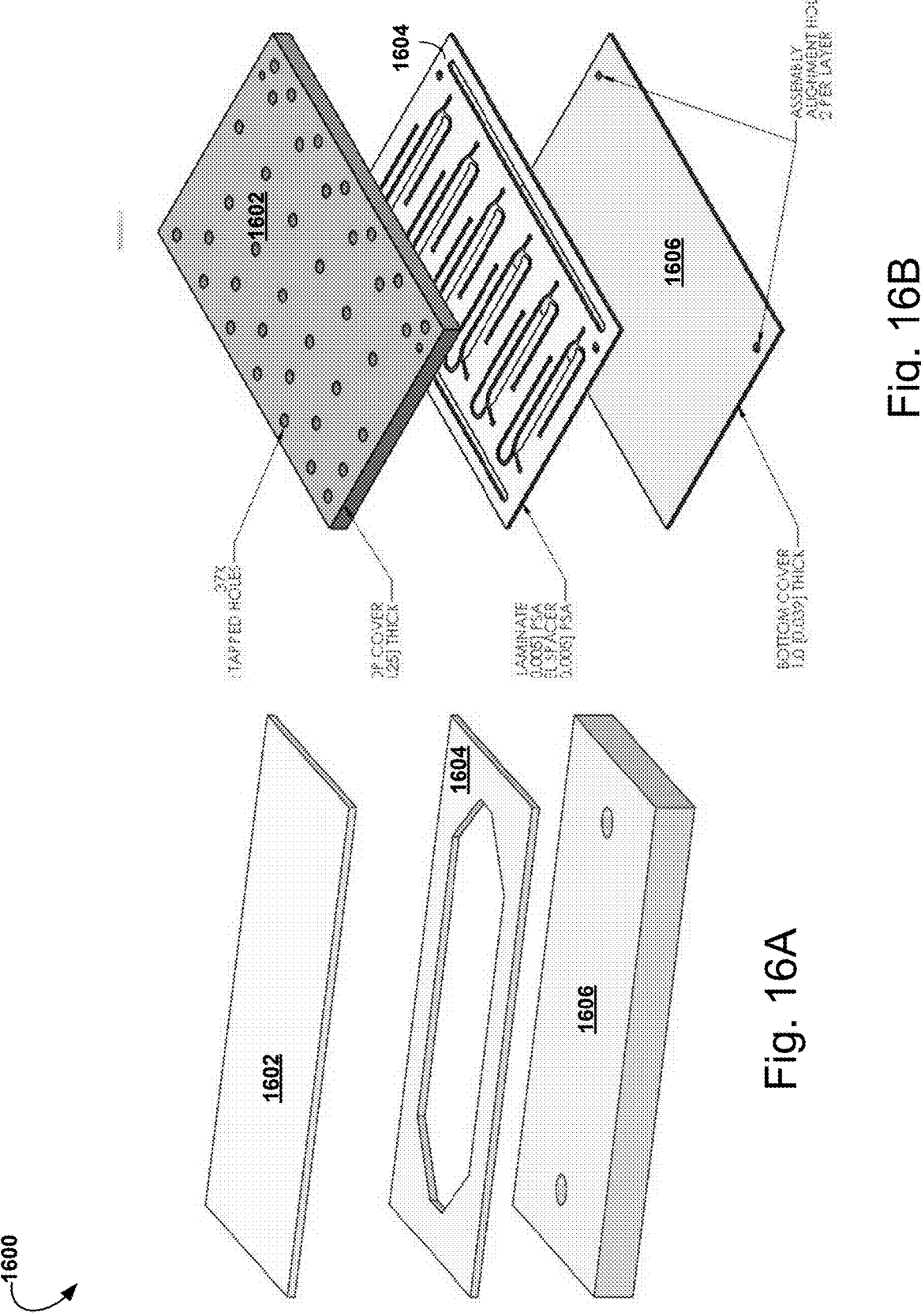
FIGS. 16A-16B each show an illustration of chip layers for fabrication of an example microfluidic chip.

FIGS. 16A-16B each show an illustration of chip layers for fabrication of an example microfluidic chip, such as microfluidic chip 100, 200, etc. described herein. The top layer 1602, described as layer 126 in FIG. 1A, is a top cover for the components of the fluid loop. The layer 1604, described as the substrate 118 of FIG. 1A, is configured to have cut out portions forming the fluid circuit itself. The bottom layer 1606 is a bottom cover, similar to layer 128 of FIG. 1A. An alternative perspective view of layers 1602, 1604, and 1606 is shown in FIG. 16B. Generally, microfluidic chip devices are fabricated with a stacked lamination approach. Layers are machined from thermoplastics (such as polycarbonate or cyclic olefin copolymer) and bonded together using pressure-sensitive adhesive or diffusion bonding. Each cavity (e.g., for cell chambers, etc.) is created by a plastic spacer with a pressure-sensitive adhesive or diffusion bonding.

Figure 17:
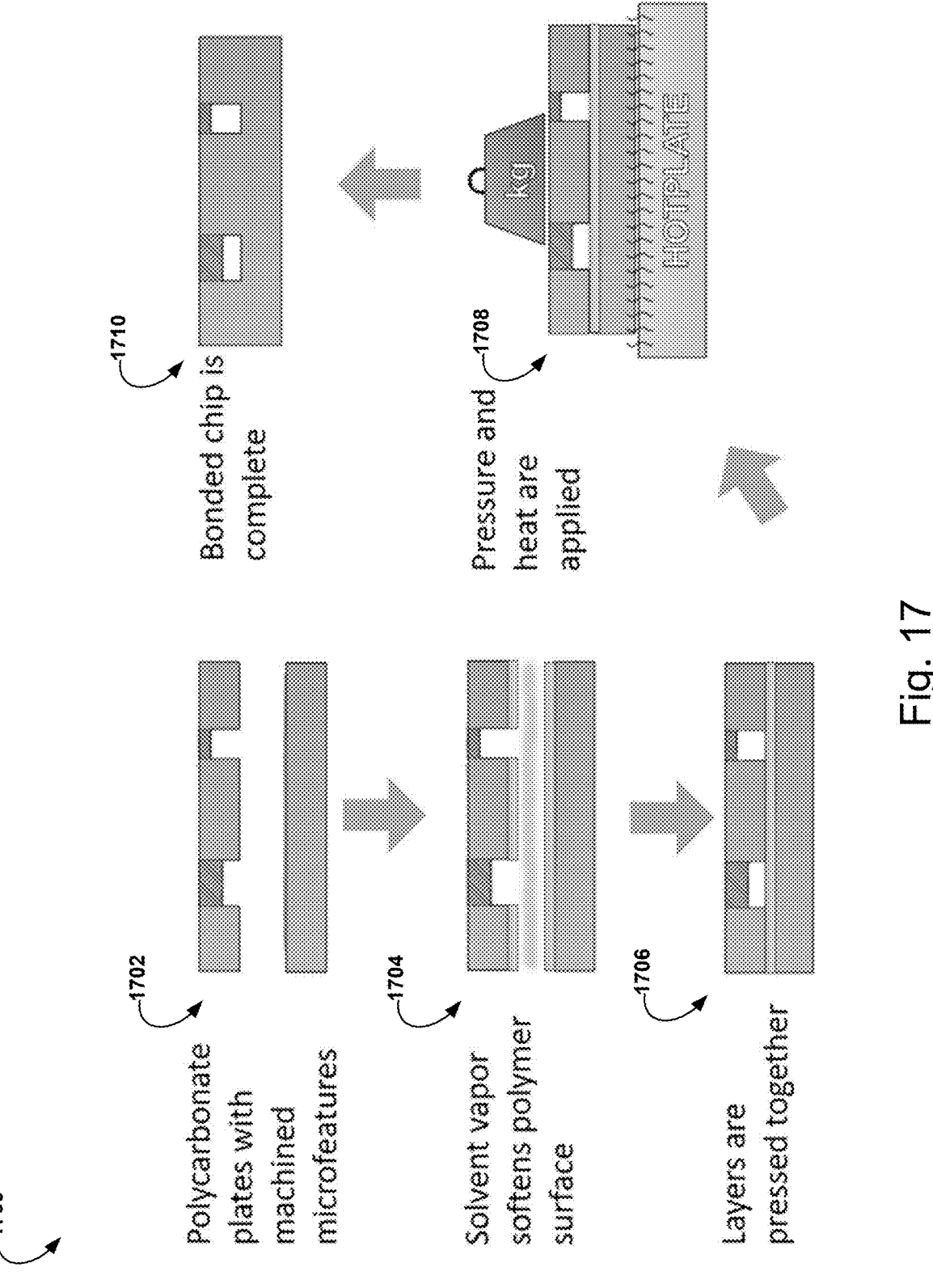
FIG. 17 is a flow diagram that illustrates an example process for fabrication of a microfluidic chip or a portion thereof.

FIG. 17 is a flow diagram that illustrates an example process 1700 for fabrication of a microfluidic chip or a portion thereof. Polycarbonate plates are machined or formed (1702) with micro features. These features include chambers, cavities, channels, etc. for fluid flow as described herein. The features form the fluid circuit loop for the microfluidic chip. The features are machined into the substrate layer.

Once the geometry of the fluid loop is determined, a solvent vapor is configured to soften (1704) the polymer surface of the machined substrate layer and the top and bottom covers. The softened surfaces of each layer are configured to adhere or meld with one another to form a solid, watertight and airtight seal. The layers are pressed together (1706) to form the seal. Pressure and heat are applied (1708) over time to the layers. The layers are bonded (1710) by the pressure and heat annealing process applied to the layers over a period of time. The result is a solid device with channels within the substrate for controlled fluid flow as described herein. A successful result can include a single, solid optically clear material with channels within the material.

In some implementations, the process parameters can include the following. The polycarbonate plates are machined to form. The softening solvent can include Dichloromethane (DCM). The DCM can be 6 mL at 28.3 in a mercury vacuum. The layers are soaked in the DCM solvent for approximately 30 minutes. The press temperature is about 255° F. The clamp pressure is about 375 pounds per square inch (psi). The formed substrate can be backed with glass on either or both sides. A sheet of silicone is included against the platen. In some implementations, a polycarbonate membrane can be stretched across holes in the substrate layer. The membrane material between the layers melts and turns optically clear.

Figure 18A:
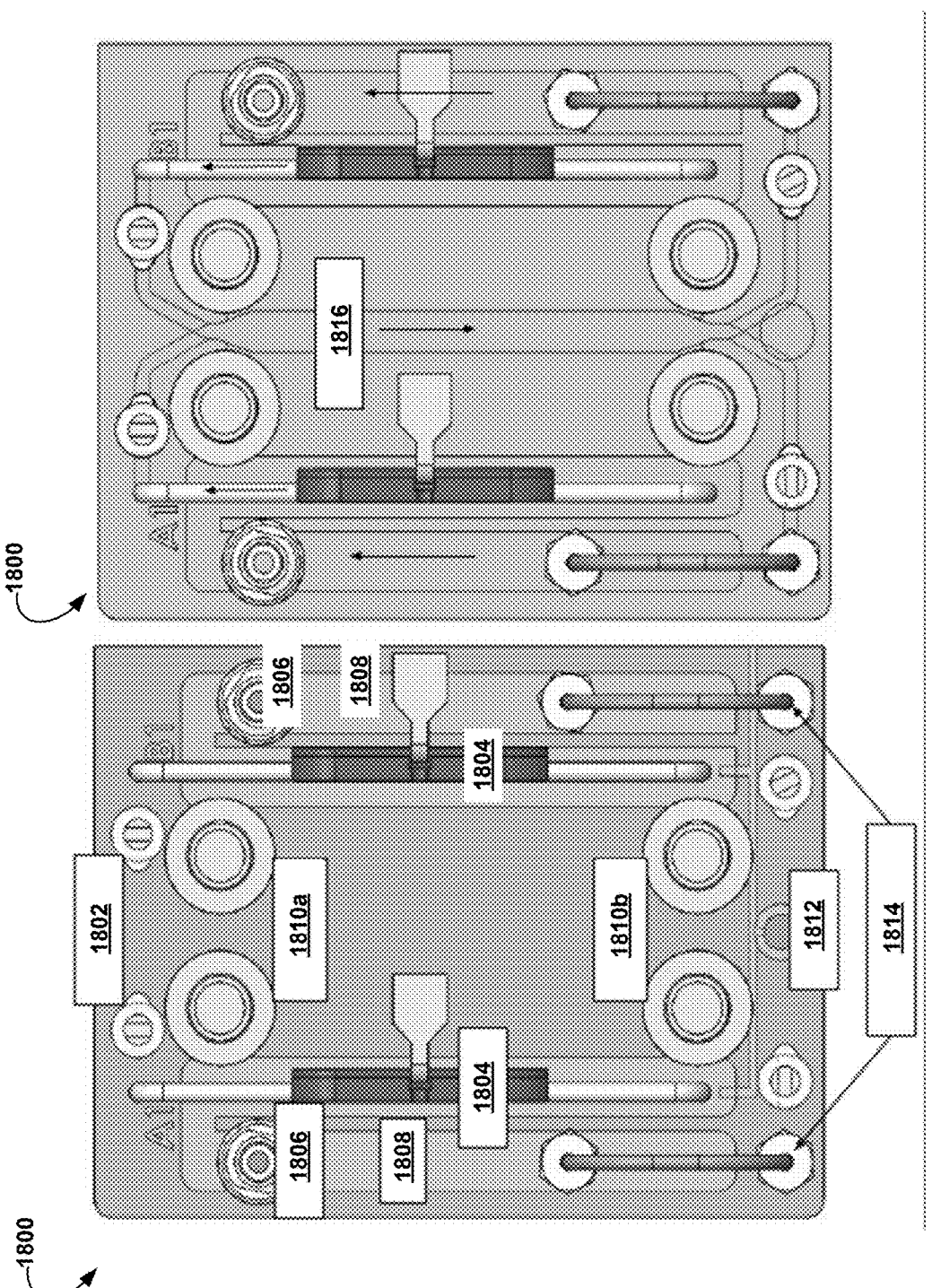
FIG. 18A shows an example top view of a two-compartment microfluidic chip.

FIG. 18A shows an example top view of a two-compartment microfluidic chip 1800. The two-compartment microfluidic chip 1800 is similar to the microfluidic chips previously described. FIG. 18A shows two different top level views of the chip 1800. A cell culture chamber 1816, shown in the left view, is divided with a porous membrane. The microfluidic chip 1800 includes the cell chamber 1816 within a fluid loop including isolation valves 1802, a pump 1804, an access port 1806, a re-oxygenation chamber 1808, an air inlet 1812, and resistive channels 1814, described in relation to other implementations of microfluidic chips herein.

The microfluidic chip 1800 includes the cell chamber 1816 having two seeding inlet ports 1810a and two seeding outlet ports 1810b. The cell chamber supports both apical and basal fluid loops. The fluid media are independently circulated to a re-oxygenation chamber, which can support dual-flow microfluidic chips. As shown in FIG. 18A, there are two instances of each of isolation valves, pump 1804, chamber 1808, access port 1806, and resistive channels 1814, one for the basal loop and one for the apical loop, and each connected to an inlet seeding port 1810a and an outlet seeding port 1810b.

Figure 18B:
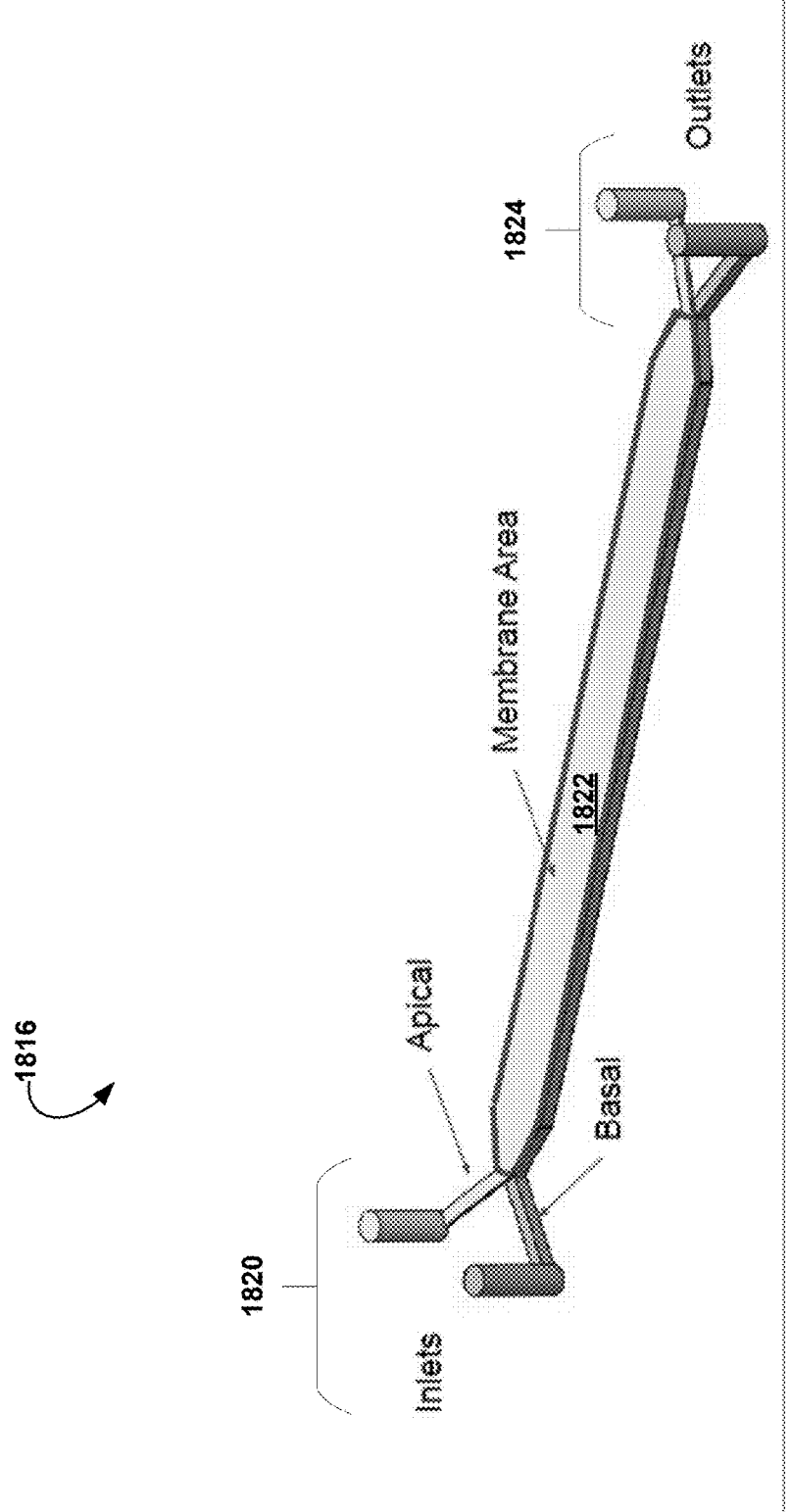
FIG. 18B shows an example cell chamber.

FIG. 18B shows an example cell chamber 1816 of FIG. 18A for apical and basal fluid loops. Two inlets 1820 are shown, including one each for the basal and apical loops. Two outlets 1824 are shown, including one each for the apical and basal loops. The internal chamber 1822 is divided into an apical side (top) and a basal side (bottom), separated by a membrane, which generally is semi-permeable to enable drug penetration from the apical side to the basal side, or vice versa. Each of the apical and basal loops can be controlled independently.

Figure 19:
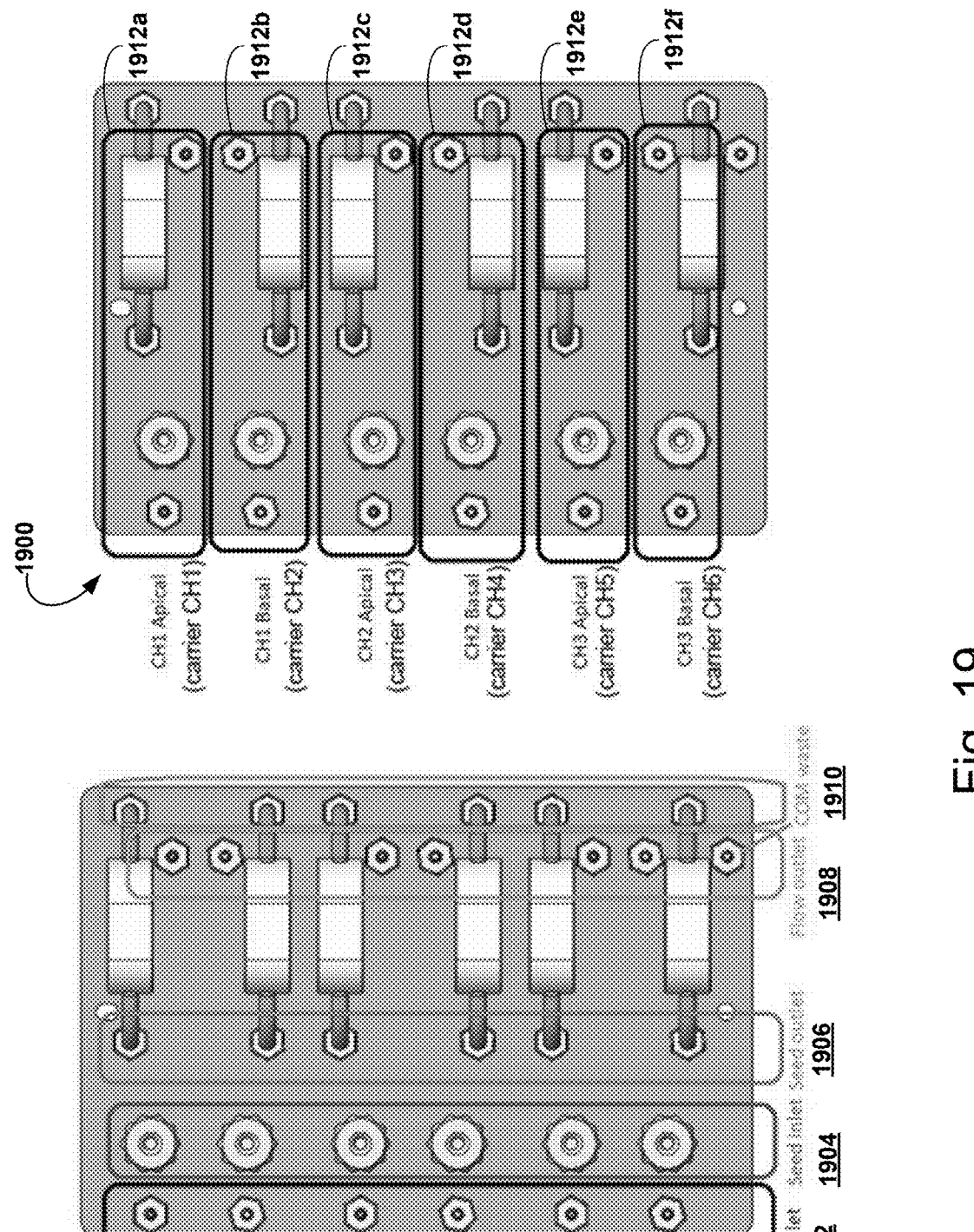
FIG. 19 shows an example microfluidic chip.

FIG. 19 shows an example microfluidic chip 1900 with a series of fluid loops included. Chip 1900 includes an array of flow inlets 1902, an array of seed inlets 1904, an array of seed outlets 1906, an array of flow outlets 1908, and an array of waste ports 1910 for each respective loop 1912a-f. Each loop includes a respective pump, re-oxygenation chamber, etc., as previously described. FIG. 19 also shows three pairs of apical and basal loops configured to share cell chambers.

Figure 20A:
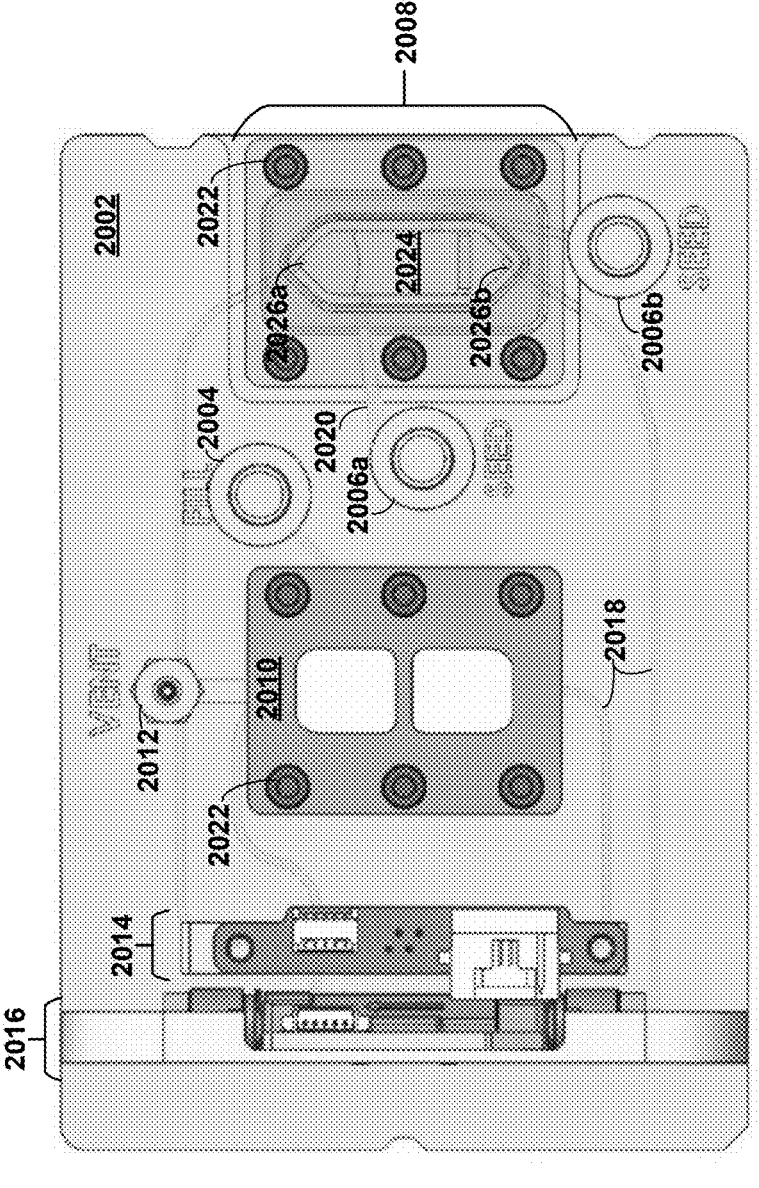
FIG. 20A shows an illustration of a top-view of an example microfluidic chip without a valve and including a cell chamber insert.

FIG. 20A shows an illustration of a top-view of an example microfluidic chip 2000. Similar to the microfluidic chips previously described in relation to FIGS. 1-19, the microfluidic chip 2000 includes a flow sensor 2016, a pump 2014, a re-oxygenation chamber 2010, a cell chamber 2024, and fluid passageways 2018 that together form a fluid loop. A cell chamber insert 2008 is configured to house the cell chamber 2024. A substrate 2002 is formed of thermoplastic. The substrate 2002 is configured to mechanically support the elements of the fluid loop. The fluid loop is a closed loop for recirculation of the fluid medium through the fluid loop.

The cell chamber insert 2008 is removable from the microfluidic chip 2000. The cell chamber insert 2008 can be fastened to the microfluidic chip 2000 using fasteners 2022. The cell chamber insert 2008 is removable to enable a user to seed and/or perfuse cells and tissue in the cell chamber 2024 away from the microfluidic chip 2000. Once the tissue is prepared, the cell chamber insert 2008 can be added to the microfluidic chip 2000. In some implementations, the microfluidic chip 2000 is reusable with different instances of the insert 2008, while the insert itself is disposable. Different examples of the insert 2008 are described in further detail herein. For example, the insert 2008 can be a top-mounted insert mounted on top of substrate 2002 (e.g., insert 3001 of FIG. 30A), or a bottom-mounted insert mounted onto a bottom layer of the microfluidic chip 2000 (e.g., insert 2901 of FIG. 29A).

As previously described, the re-oxygenation chamber 2010 is configured to add oxygen to the fluid medium in a precise concentration. The concentration emulates a concentration of oxygen that would be available to tissue in the cell chamber 2024 if the tissue were in the human body. The pump 2014 pumps the fluid media through the fluid loop at a controlled rate (e.g., 1-2 mL/hour). The flow rate is set to a slow flow rate to minimize shear experienced by the tissue in the cell chamber 2024. The fluid media is pumped from the pump 2014 through the cell chamber 2024, through the flow sensor 2016, through the re-oxygenation chamber 2010, and back to the pump. As previously described, the fluid recirculates though the cell chamber 2024 repeatedly in a closed, recirculating fluid loop.

The re-oxygenation chamber 2010 is configured to provide a particular concentration of oxygen to the fluid medium, as described previously in reference to FIGS. 1-19. The re-oxygenation chamber 2010 can be modular with respect to the rest of the microfluidic chip 2000. For example, the re-oxygenation chamber 2010 can be fastened to the substrate 2002 with fasteners 2022. The re-oxygenation chamber 2010 can be removed and replaced with another instance of the re-oxygenation chamber without replacing the other hardware elements (e.g., the pump 2014, flow sensor 2016, etc.) of the microfluidic chip 2000.

The cell chamber 2024 hosts the tissue for emulation of tissue functionality. For example, as previously described, the tissue is configured to experience an emulated in vitro environment within the cell chamber 2024. In some implementations, the cell chamber 2024 is a modular portion (also called an insert 2008) that can be added or removed from the microfluidic chip 2000 using fasteners 2022. This portion includes a semi-permeable membrane that hosts a cell/tissue culture. The insert enables the tissue to be cultured independently from the microfluidic chip 2000, and then added to the fluid loop once the tissue is mature for experimentation. For example, a first cell culture can be swapped for a second cell culture without replacing the remaining hardware (e.g., the pump 2014, flow sensor 2016, etc.) on the microfluidic chip. Fluid enters the cell chamber 2024 at port 2026*a* and exits at port 2026*b*.

The microfluidic chip 2000 includes several ports for adding or removing cells, drugs, or fluid medium to the fluid loop. The microfluidic chip 2000 includes a fill port 2004 that enables a user to fill the fluid loop with fluid medium. The microfluidic chip 2000 includes seeding ports 2006*a-b*. In some implementations, the seeding port 2006*a* enables a user to seed an apical side of the cell chamber 2024, and the seeding port 2006*b* enables a user to seed a basal side of the cell chamber 2024. The tissue of the cell chamber 2024 can be seeded directly within the cell chamber 2024, rather than being cultured in another environment and later added to the cell chamber. The passage 2020 from the port 2006*a* to the cell chamber 2024 is generally straight. The straight passage 2020 prevents or reduces cell death during injection of the cells into the fluid loop. For example, during injection, a pipette creates high-flowrate (e.g. 300 μl in 60 sec injection). With such a flowrate, the cells generally hit curves in a seeding channel. The cell-wall interaction can cause cell death for the injected cells. For a straight geometry, cell death is minimal. In some implementations, the seeding ports 2006*a-b* are threaded with metal to extend a life of the microfluidic chip 2000. Generally, the components of the ports 2006*a-b* otherwise include molded thermoplastic. A vent 2012 enables air to escape from the fluid loop as fluid media is introduced.

The microfluidic chip 2000 does not have a valve, such as valve 114 of MPS 1400 described previously. The microfluidic chip 2000 is formed from a plurality of layers that are mechanically fastened together. In some implementations, the layers, including substrate 2002, are formed from thermoplastic. In some implementations, the thermoplastic includes cyclic olefin copolymer (COC)-based thermoplastic. In some implementations, the thermoplastic includes polycarbonate (PC)-based thermoplastic. At least two layers of the thermoplastic material are heat bonded together, forming the fluid passageways 2018 and chambers 2010, 2024 of the recirculation loop.

Construction from the thermoplastic, as opposed to a polydimethylsiloxane (PDMS)-based plastic, provides several advantages. The thermoplastic material enables the microfluidic chip 2000 to be formed from layers of thermoplastic that are mechanically coupled together (e.g. with screws). Construction of the entire fluid loop from the thermoplastic, as opposed to only a portion of the fluid loop such as the cell chamber 2024, enables recirculation of fluid through a fluid loop that includes the hosted tissue culture. Recirculation of the fluid through the fluid loop enables high fidelity emulation of human physiology. Fluid can be pumped (e.g., by pump 2014) through or across the tissue to the re-oxygenation chamber 2010 that adds a precise amount of oxygen to the fluid media without any exposure to oxygen outside of the fluid loop. The fluid media is then re-pumped through the cell chamber 2024. The closed loop configuration enables more accurate testing of drug absorption in the tissue in comparison with open loop configurations in which fluid media is pumped across a cell chamber once. The closed fluid loop enables extended emulation of human physiology for a tissue sample. The closed fluid loop can be automatically sampled at various points in time over a course of hours, days, weeks, months, and so forth.

The thermoplastic construction of the fluid loop enables recirculation of the fluid in a closed fluid loop without drug adsorption into the thermoplastic. Adsorption includes an adhesion of the drug (e.g., a lipophilic drug) or fluid media to the channels of the microfluidic chip 2000. This process creates a film of the drug on the surface of the fluid channels and within the cell chamber 2024. For example, PDMS can absorb up to 100% of drugs in the fluid loop if the microfluidic chip 2000 is constructed from PDMS when the fluid is pumped quickly through the cell chamber. The thermoplastic material of the microfluidic chip 2000 enables testing of a wider variety of drugs with higher precision relative to PDMS-based MPSs. Because drug adsorption is limited, the thermoplastic material of the microfluidic chip 2000 enables a fast flow fluid loop (e.g., several mL/hour), mimicking a human physiology and enabling accurate emulation of drug absorption in the human body. For example, the cell chamber geometry enables a reduced shear on the cells of the tissue in the fluid loop (even for fast flow recirculating systems), relative to a higher shear experienced by cells in other cell chamber geometries. A lower shear improves testing outcomes and destroys fewer cells in the tissue. Flow rates for PDMS-based cell chambers are relatively slower to reduce shear on the cells. The microfluidic chip 2000 enables higher oxygenation rates relative to PDMS-based flow through systems that do not have a waterfall feature. This raises oxygenation levels supplied to the cells in the cell chamber relative to those PDMS-based flow through systems, and avoids cell death near the cell chamber exit (e.g., caused by depleted oxygen levels near the cell chamber exit).

Figure 20B:
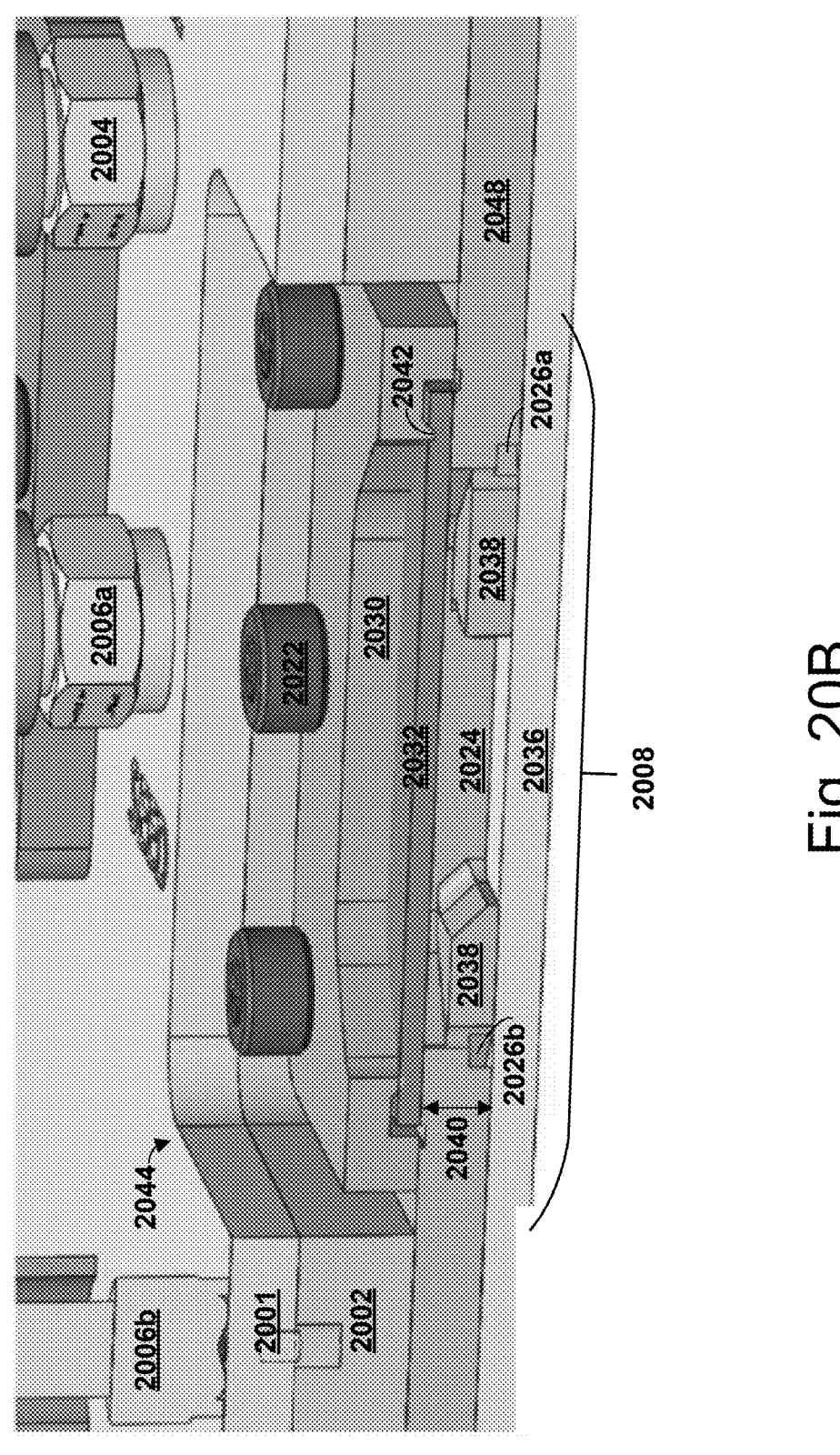
FIG. 20B shows an illustration of a perspective cutaway-view of an example microfluidic chip cell chamber of a cell chamber insert.

FIG. 20B shows an illustration of a perspective cutaway-view of an example microfluidic chip 2000 cell chamber 2024 and insert 2008. The cell chamber 2024 is constructed from the thermoplastic. The cell chamber 2024 is shaped to enable a required oxygen concentration (or oxygen concentration gradient) within the tissue in the cell chamber. The cell chamber insert 2008 houses the cell chamber 2024 and includes a clamp 2030, a membrane 2032, a chamber wall layer 2048, and a bottom layer 2036. Fluid enters the cell chamber 2024 through an entry port 2026a and exits through an exit port 2026b. The membrane is an oxygen-permeable membrane to support oxygenation of the tissue during a static seeding period (e.g., 24 hours), prior to circulation of the fluid media.

The cell chamber 2024 is formed with the membrane 2032 on a top side and the bottom layer 2036 on the bottom side. The membrane 2032 is held in place with notches 2042 in the clamp 2030. Fasteners 2022 hold the clamp 2030 to the chamber wall layer 2048. The chamber wall layer 2048 is below the substrate 2002 layer and top layer 2001. The substrate 2002 includes the channels and chambers forming the fluid loop, with cutaway portion 2044 for the cell chamber 2024 and for the re-oxygenation chamber (not shown in FIG. 20B).

The cell chamber 2024 has a particular geometry to enable a precise oxygen gradient and precise shear stress within the cell chamber 2024. The cell wall layer 2048 is of a particular height (thickness) 2040. In some implementations, the height is approximately 3 mm. In some implementations, the height 2040 is approximately 2 mm. The height 2040 of the cell wall layer 2048 is a basis for the height of a waterfall feature 2038 in the cell chamber 2024. As previously described, the waterfall feature 2038 causes a particular oxygen gradient in the cell chamber 2024 that enables the tissue throughout the cell chamber to receive enough oxygen at low flow rates (e.g., <3 mL/hour) of fluid media through the cell chamber 2024. The low flow rates of the fluid media through the cell chamber 2024 ensure that a shear on the cells of the tissue are below a given threshold. The low shear stress on the cells of the tissue enables increased cell survival, relative to cells experiencing a higher shear stress from faster flow rates Geometries of the cell chamber 2024 are described in further detail with respect to FIGS. 22A-23B.

Figure 20C:
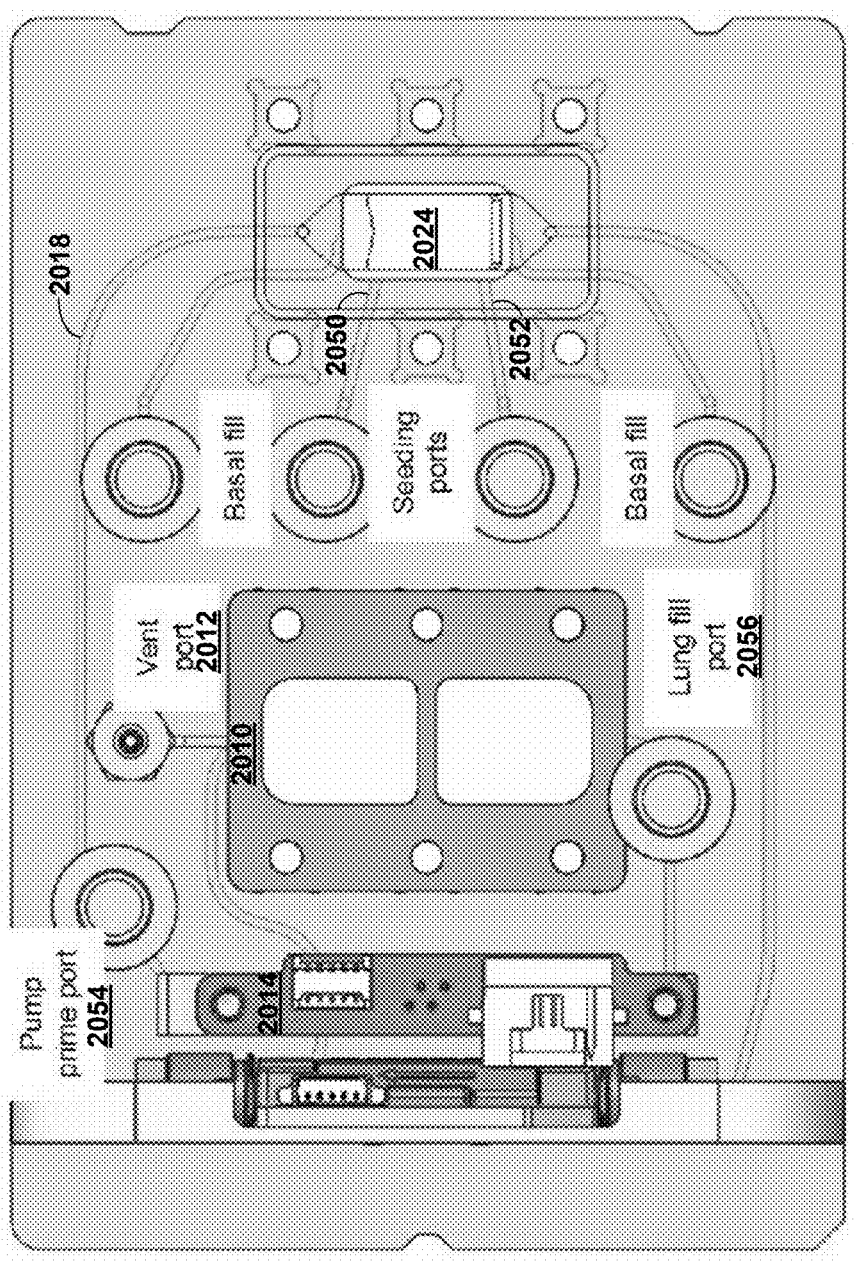
FIG. 20C shows an illustration of a top-view of an example microfluidic chip including a cell chamber insert.

FIG. 20C shows an illustration of a top-view of an example microfluidic chip 2060. Microfluidic chip 2060 is similar to microfluidic chip 2000, and includes illustrations of alternative microfluidic channels 2018 and additional ports. For example, the microfluidic chip 2060 includes a pump priming port 2054. The pump priming port 2054 enables a user to prime the pump 2014 with fluid media. The microfluidic chip 2060 includes a re-oxygenation chamber fill port 2056. The port 2056 enables the user to fill the re-oxygenation chamber 2010 with fluid media. The microfluidic chip 2060 is a two-compartment chip configured for recirculation of the fluid media. The microfluidic chip 2060 includes a loop for an apical side and a loop for a basal side.

The microfluidic paths 2018 are for microfluidic chip 2060 show how the fluid media are transported around the microfluidic chip. The channels 2050, 2052 from the seeding ports are straight in order to prevent or mitigate cell damage during seeding of the cell chamber 2024.

Figure 21A:
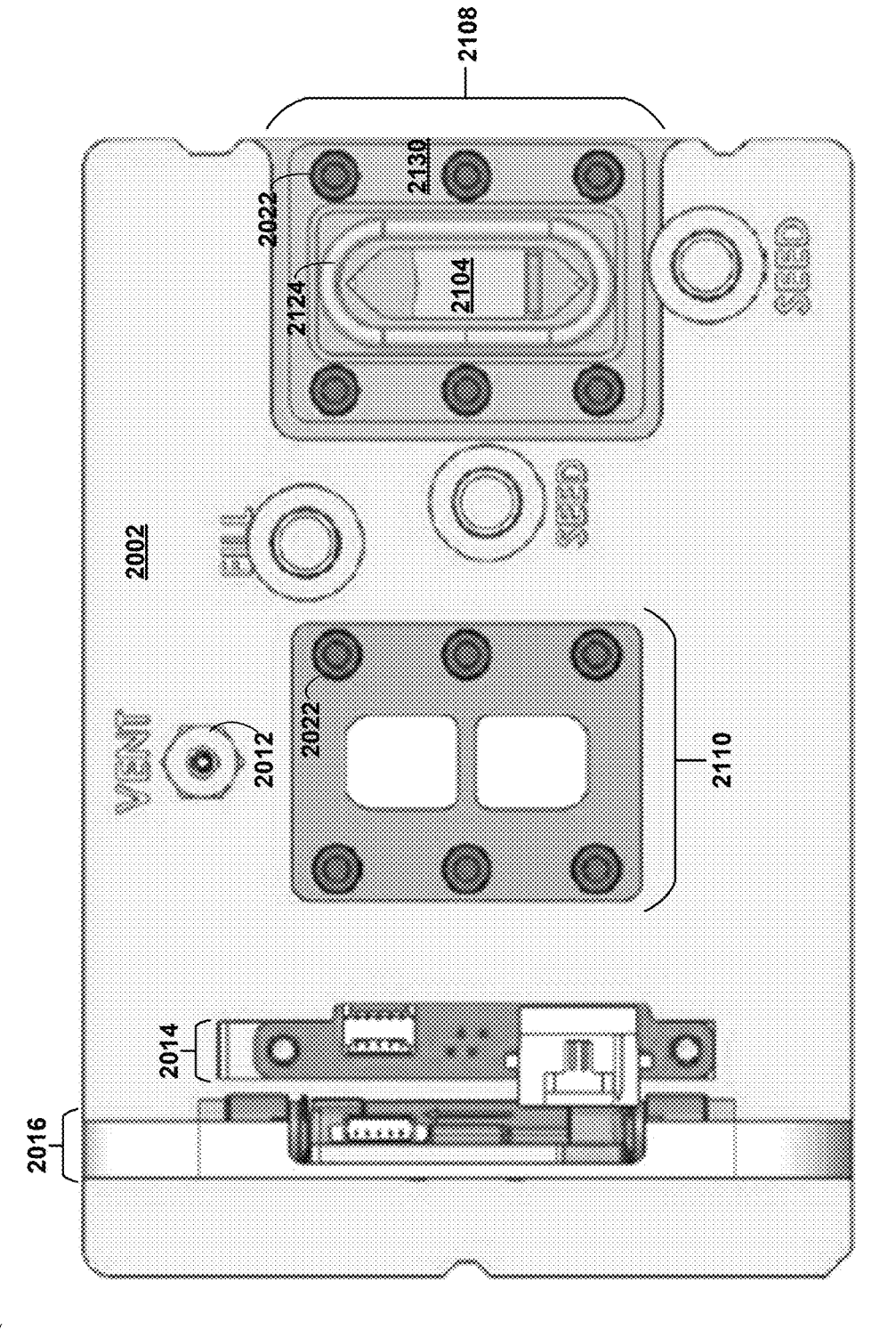
FIG. 21A shows an illustration of a top-view of an example microfluidic chip.

FIG. 21A shows an illustration of a top-view of an example microfluidic chip 2100 that does not include a valve or a cell chamber membrane. The microfluidic chip 2100 is similar to microfluidic chip 2000, except that the cell chamber 2104 includes a design that does not include a membrane. The cell chamber 2104 can be a modular portion (e.g., insert 2108) of the fluid loop that is configured to be removable from the substrate 2002. A cover 2130 of the cell chamber 2104 is held in place by fasteners 2022. The cover 2130 is a hard top cover made of COC or PC thermoplastic. In some implementations, other thermoplastics can be used (e.g., polystyrene or any such thermoplastic). The cover is not oxygen permeable, and therefore enables precise control of the oxygen gradient in the cell chamber 2104. A seal 2124, such as an O-ring seal, seals the cell chamber 2104 closed when the cover 2130 is fastened to the microfluidic chip 2100. As with previous microfluidic chips described herein, the microfluidic chip 2100 includes a re-oxygenation chamber 2110 that provides oxygen to the cell chamber 2104. The fluid media is circulated and recirculated by pump 2014, which can be any of the pumps described in this specification. A sensor 2016, such as a flow sensor, can be used to control the recirculation of the fluid media.

Figure 21C:
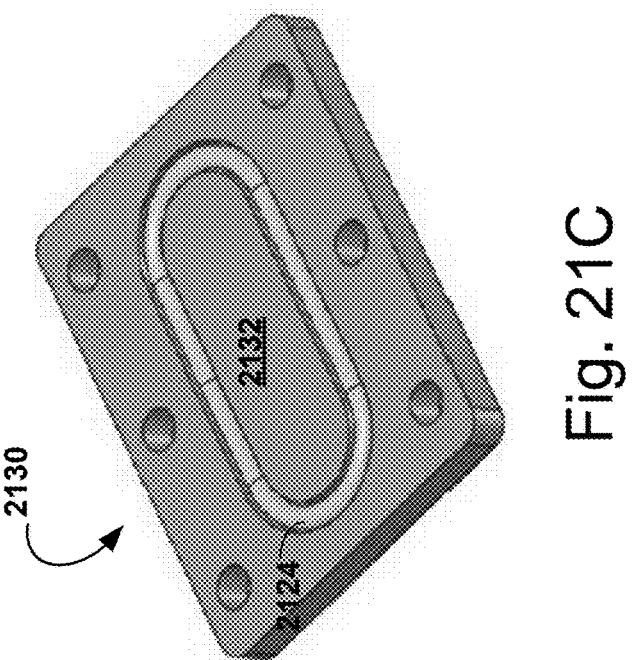
FIG. 21C shows an illustration of a floating microfluidic chip cell chamber insert cover.
Figure 21B:
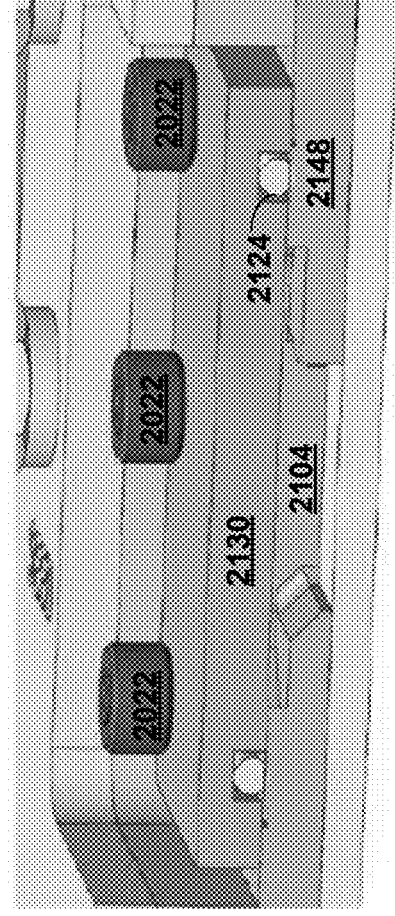
FIG. 21B shows an illustration of a perspective cutaway-view of an example microfluidic chip cell chamber insert.
Figure 21B:

FIG. 21B shows an illustration of a perspective cutaway-view of an example microfluidic chip cell chamber insert 2100. The cell chamber insert 2108 includes a solid cover 2130 which can be made of a thermoplastic (e.g., COC or PC). The cover 2310 is affixed to the cell chamber wall layer 2148 by the fasteners 2022. The cell chamber wall layer 2148 forms the geometry of the cell chamber 2104 of the insert 2108, as described in relation to FIG. 20B. The fasteners 2022 press the cover 2130 onto the cell chamber wall layer 2148 so that the seal 2124 seals the chamber.

FIG. 21C shows an illustration of a floating microfluidic chip cell chamber insert cover 2130. The cover 2130 includes the seal 2124 which encircles a region 2132 that forms the top of the cell chamber 2104.

Figure 21D:
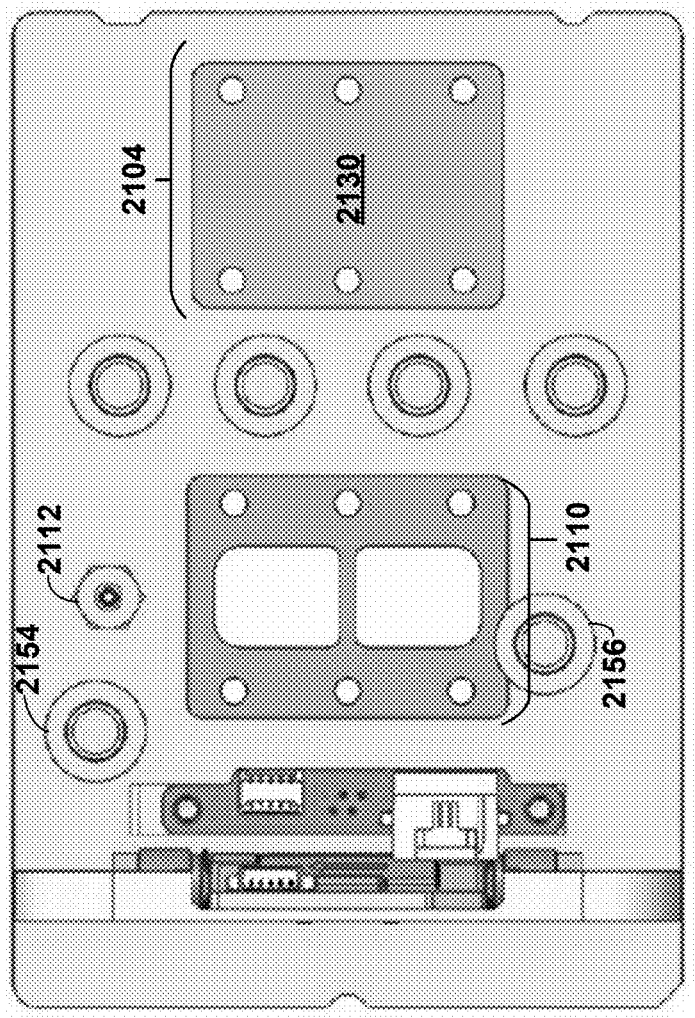
FIG. 21D shows an illustration of a top-view of an example microfluidic chip cell chamber.

FIG. 21D shows an illustration of a top-view of an example microfluidic chip 2160. The microfluidic chip 2160 is a two-compartment chip that is configured for recirculation of the fluid media. The cell chamber 2104 is included in the microfluidic chip 2160. The microfluidic chip 2160 includes a loop for an apical side and a loop for a basal side. Generally, the basal loop is stagnant while the apical side is recirculated. Similar to the microfluidic chip 2060 of FIG. 20C, the microfluidic chip 2160 include a pump priming port 2154 and a re-oxygenation chamber fill port 2156. The cell chamber 2104 includes the solid cover 2130.

Figure 21E:
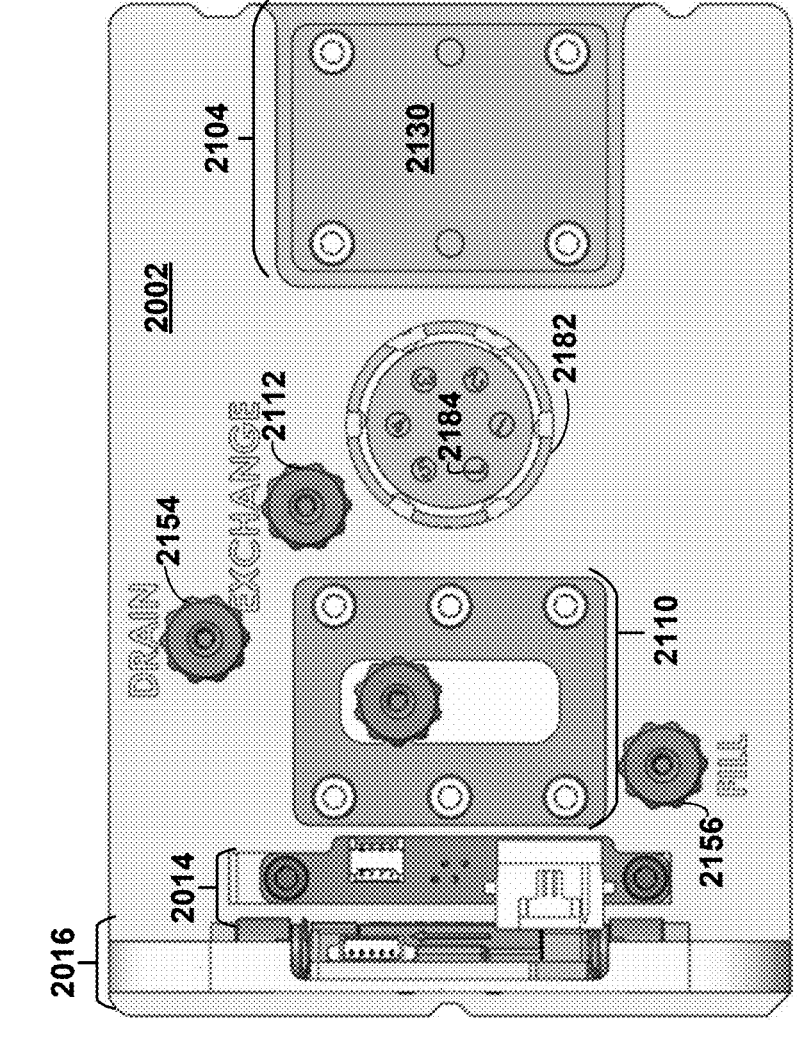
FIG. 21E shows an illustration of a top-view of the microfluidic chip of FIGS. 21A-D including a sampling carousel.

FIG. 21E shows an illustration of a top-view of a microfluidic chip 2180, similar to microfluidic chip 2100 of FIGS. 21A-D. The microfluidic chip 2180 includes a sampling carousel 2182, which can be similar to carousel 1402 described previously in relation to FIGS. 14A-14C. In some implementations, the sampling carousel 2182 includes a separate molded component that attaches to the microfluidic chip 2182. In some implementations, the carousel 2182 is retained in the microfluidic chip 2180 by the substrate layer 2002. In some implementations, a bottom of the carousel (not shown) includes a mechanical feature (e.g., a gear, extension member, etc.) configured to interface with a corresponding feature (e.g., a corresponding gear) in a support module (e.g., support module 630). The mechanical feature on the carousel 2182 enables an automatic indexing of the sampling carousel 2182 for each sampling well 1-7. For example, when the sampling carousel 2182 is in a particular position, fluid media flows through the sampling carousel, filling a given sample chamber (e.g., one of chambers 1-7). When it is time to collect a sample, a motor in the support module 630 indexes to a next position. The captured fluid media is retained in the sample chamber. The fluid media can be removed (e.g., at the end of an experiment) by a user. A top 2184 of the sampling carousel will have a layer that is able to be pierced (e.g., foil) that allows a user to extract discrete samples using a pipette.

A position of the sampling carousel 2182 is sensed by a sensor (not shown) in the support module 630 to ensure that the carousel correctly indexes between positions. For example, a Hall-effect sensor in the support module 630 can be used to detect magnets in the sampling carousel 2182 to determine position. In another example, a position is tracked using a light sensor or using a motor encoder in the support module. In some implementations, a stepper motor can be used. Other similar position tracking approaches can be used.

Figure 21F:
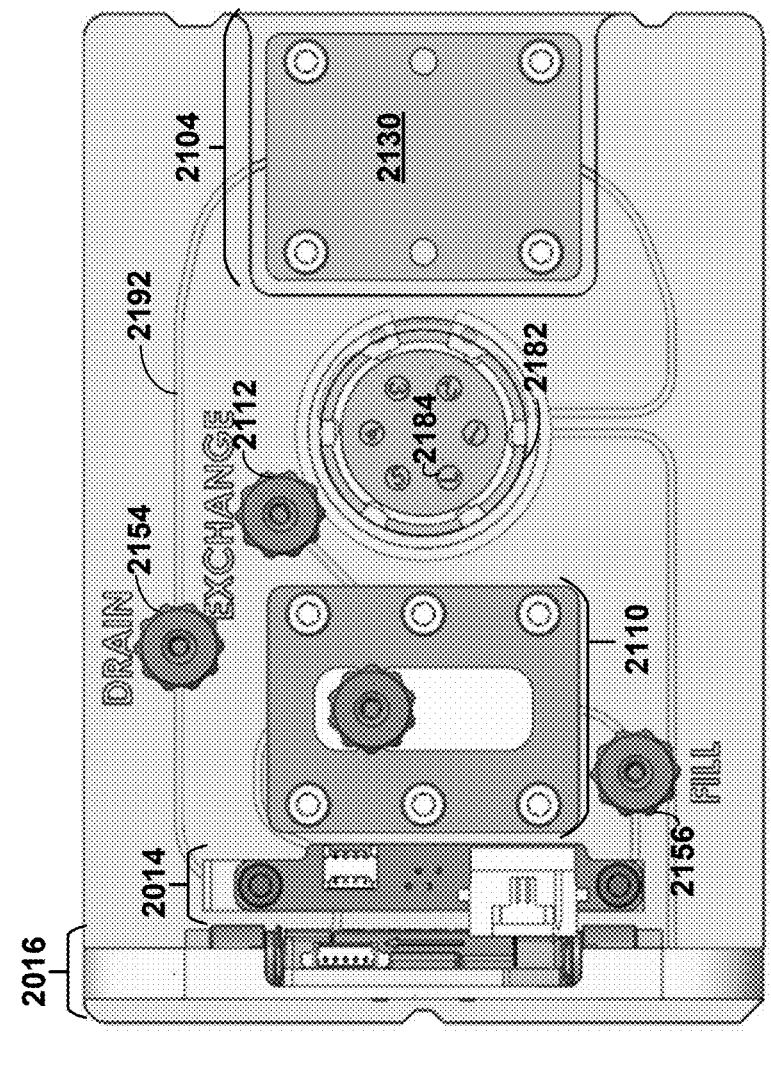
FIG. 21F shows an illustration of a top-view of the microfluidic chip of FIGS. 21A-E including a sampling carousel with a substrate layer removed.

FIG. 21F shows an illustration of a top-view of the microfluidic chip 2182 of FIGS. 21A-E including a sampling carousel with a substrate layer removed. A fluid circulation channel 2192 is shown on the microfluidic chip 2180.

Figure 21G:
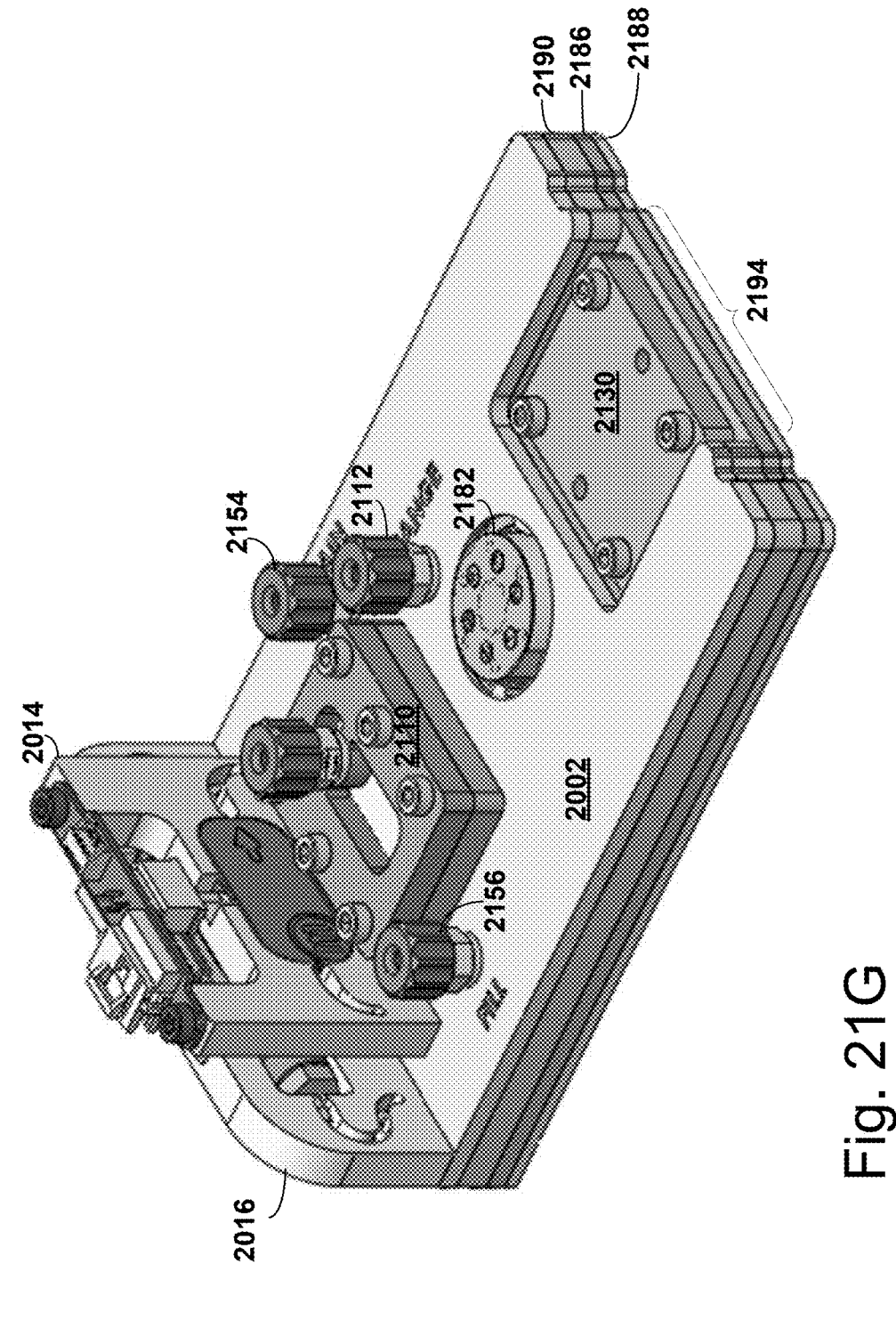
FIG. 21G includes an illustration of a perspective view of the microfluidic chip of FIGS. 21A-E showing a cell chamber insert.

FIG. 21G includes an illustration of a perspective view 2182 of the microfluidic chip of FIGS. 21A-E showing a cell chamber insert 2194. As described herein, the insert 2194 is a top-loading insert. The cover 2130 is placed on top of a cell chamber (not shown) that is formed in the cell chamber layer 2186 of the microfluidic chip 2180. The removable cover 2130 allows a user to seed the cell chamber with cells without injecting through ports. Rather, the cells can be seeded and perfusion can occur by directly applying (e.g., injecting) the cells onto a permeable membrane of the insert 2194. In some implementations, the insert 2194 can be a bottom-loading insert in which a cover is coupled to the bottom layer 2188 of the microfluidic chip 2180. Fluid media can flow through the cell chamber of the insert 2194 as well as the sampling carousel 2182, being circulated by the pump 2014 through the re-oxygenation chamber 2110 as previously described.

Figures 22A, 22B:
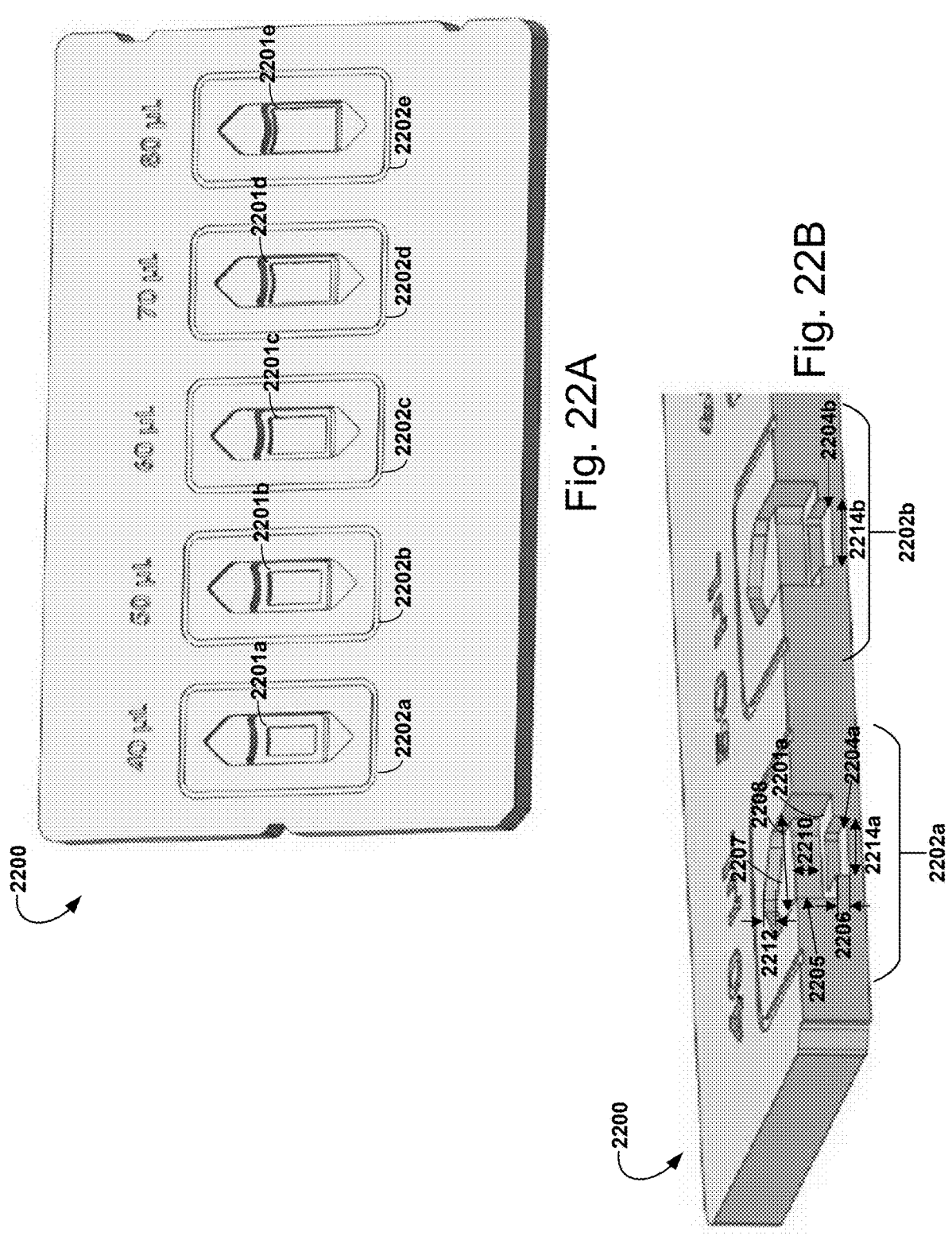
FIG. 22A shows an illustration of a perspective view of cell chambers for an example microfluidic chip.
FIG. 22B shows an illustration of a cutaway side-view of cell chambers for an example microfluidic chip.

FIG. 22A shows an illustration of a perspective view of cell chambers 2202a-e for an example microfluidic chip. In some implementations, the cell chambers 202a-e are each configured for tissue hosted in a gel. For example, the gel-embedded cells are introduced into the cell chamber below the shelf 2201. Although the individual cell chambers 2202a-e are shown as part of a common layer 2200, the cell chambers are included in separate microfluidic chips. The layer 2200 is shown for example purposes to indicate different possible configurations for the cell chambers 2202a-e. For example, the volume for cell chamber 2202a is 40 μL. The volume of the cell chamber 2202a is the volume available for gel-embedded cells. For example, the volume for cell chamber 2202b is 50 μL. For example, the volume for cell chamber 2202c is 60 μL. For example, the volume for cell chamber 2202d is 70 μL. For example, the volume for cell chamber 2202e is 80 μL. The volume for each chamber (e.g., 2204a-b) is adjusted by changing the size of respective shelves 2201a-e. A given cell chamber 2202 includes a waterfall design in which the respective shelf 2201 enables a lower shear on the cells of the hosted tissue within the chamber while allowing a fast enough flow rate of the fluid media to oxygenate the tissue. The exact size of the cell chamber 2202 depends on the tissue hosted in the cell chamber. The exact possible geometries of the cell chamber 2202 are described in relation to FIG. 22B.

FIG. 22B shows an illustration of a cutaway side-view of cell chambers 2022a and 2202b. The cell chambers 2202a-b are configured so that replicas may each may be included in respective example microfluidic chips. The cell chamber 2202a includes a well 2204a that is configured to host gel-embedded cells with a particular volume. For example, the gel-embedded cells can include liver cells. The well 2204a has a width 2214a, a height 2206, and a depth. The well 2204a size depends on the amount of tissue to be hosted within the cell chamber 2202a. Fluid media traverses within the cell chamber 2202a over the gel-embedded cells. The fluid media is within a larger well 2205 defined by a height 2210 and a width 2208. The height 2210 is the height of a waterfall feature within the cell chamber 2202a. The waterfall feature includes a step from a first level of the cell chamber 2202 to a second level of the cell chamber. The step is a vertical wall inside the cell chamber within the flow path of the fluid media over the cells in the cell chamber. The waterfall feature causes the fluid media to oxygenate the tissue without causing high shear stress on the tissue above an unacceptable threshold that would cause cell death. The height of the waterfall feature 2210 can be 2 mm-3 mm. The shelf 2201a helps to define a volume for the gel wells 2204a, which defines the gel volume within the cell chamber 2202a. An upper shelf portion 2207 of the cell chamber 2202a forms the top of the waterfall feature. A thickness 2212 of the upper shelf portion 2207 can be 1 mm-2 mm.

Generally, if the tissue is seeded in gels in the defined volumes of wells 2204a-b, the top of the gel can be exposed to certain shear and $O_2$ tension. The upper shelf portion 2207 of the waterfall reduces the shear coming from the narrow channels, inversely proportional to width. When fluid media reaches to the waterfall feature, the waterfall decreases shear stress, since shear is inversely proportional to the square of the height 2210 of the waterfall feature.

The cell chamber 2202b includes a well 2204b with a smaller width 2214b. This enlarges the overall volume of the cell chamber 2202b by 10 μL relative to cell chamber 2202a. The size of the cell chamber 2202b is increased without changing a geometry of the waterfall feature, upper shelf, or larger well 2205.

Example cell chamber dimensions are now described. In some implementations, the cell chamber channel total height (heights 2210, 2206, and 2210) is 3 mm. In some implementations, the surface area of well (e.g., well 2204a-b) is 1 $cm^2$. In some implementations, the cell chamber total height is 2 mm. Examples of specific dimensions are provided in Table 2.

TABLE 2

| | Example Dimensions for a microfluidic chip 2000 | | | |
| --- | --- | --- | --- | --- |
| Category | Surface Area [$mm^2$] | Height [mm] | Volume ($mm^3$) | Volume (mL) |
| Re-oxygenation Chamber | 196.60 | 2.00 | 393.20 | 0.39 |
| Cell Channel (Cell Area) and Above) | 100.00 | 3.00 | 300.00 | 0.30 |

TABLE 2-continued

| | Surface Area [mm^2] | Height [mm] | Volume (mm^3) | Volume (mL) |
|---|---|---|---|---|
| Category | Example Dimensions for a microfluidic chip 2000 | | | |
| Cell Channel (Waterfall Tops) | 67.00 | 1.00 | 125.00 | 0.13 |
| Paths | 309.12 | 1.00 | 309.12 | 0.31 |
| Liquid Columns/Vertical Paths | N/A | N/A | 66.68 | 0.07 |
| Pump & Flow Sensor | N/A | N/A | 50.00 | 0.05 |
| Total Recirc | 672.72 | Variable | 1,244.00 | 1.24 |
| Drain Port | N/A | N/A | 78.51 | 0.08 |
| Fill Ports | N/A | N/A | 78.51 | 0.08 |
| Total Dead | 73.00 | | 157.03 | 0.16 |
| Total Volume | | | 1,401.03 | 1.40 |

Figure 23A:
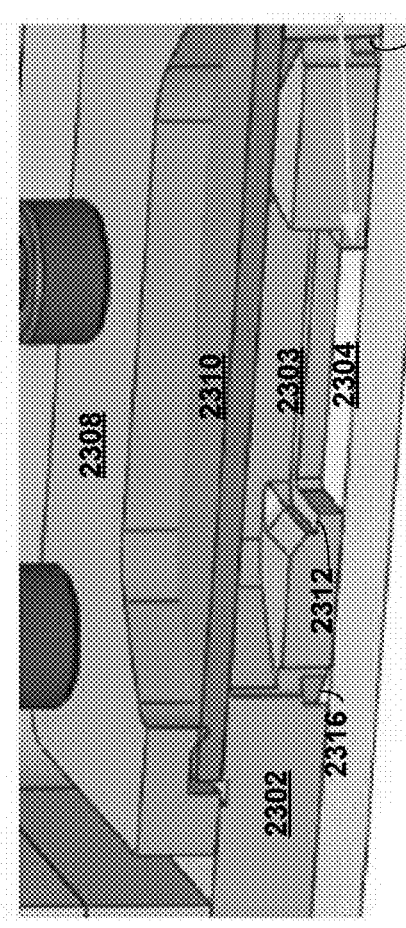
FIG. 23A shows an illustration of a cutaway side-view of a cell chamber insert for a microfluidic chip.
Figure 23A:

FIG. 23A shows an illustration of a cutaway side-view of a cell chamber insert 2300 for a microfluidic chip including a cell chamber 2303. In some implementations, the cell chamber 2303 is configured to host muscle tissue. The cell chamber insert 2300 can be based on the cell chamber 2202a-e of FIGS. 22A-B. The cell chamber insert 2300 includes a clamp 2308. The clamp 2308 can be formed from thermoplastic and fastened to the substrate of the microfluidic chip with fasteners. A membrane 2310 forms the top of the cell chamber 2303 that hosts the muscle cells. A well 2304 is formed within the cell chamber 2303. The well 2304 is formed by a shelf 2312 in the cell chamber wall layer 2302, similar to microfluidic chips as previously described. The shelf is part of a waterfall feature 2312 that reduces shear on the tissue within the well 2304. The cell chamber 2300 has an input port 2306 and an output port 2316. Generally, muscle cells are more sensitive to shear, and thus are protected in the gel. In some implementations, cancerous cells can be introduced into the well 2304 for PK/PD testing.

Figure 23B:
FIG. 23B shows a top-view of a cell chamber for a microfluidic chip.
Figure 23B:
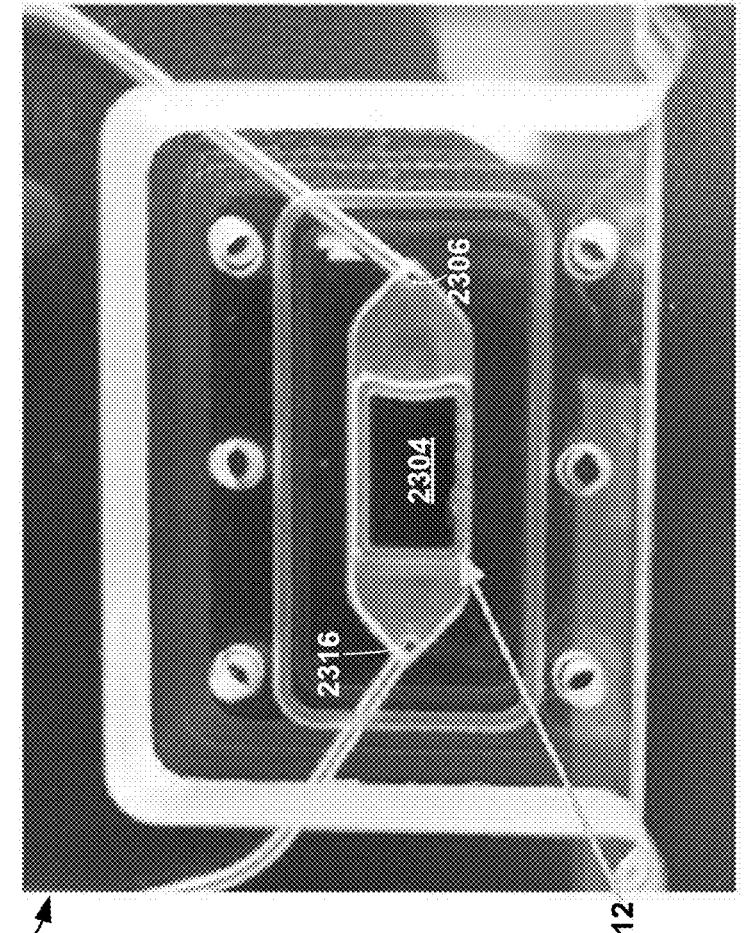

FIG. 23B shows a top-view of a cell chamber wall layer 2302 for a microfluidic chip. The cell chamber wall layer 2302 is formed from molded thermoplastic. The cell chamber well 2304 and shelf 3212 are visible in the clear material. In this example, the cell chamber well 2304 is configured to hold 70 μL of gel.

Figure 24A:
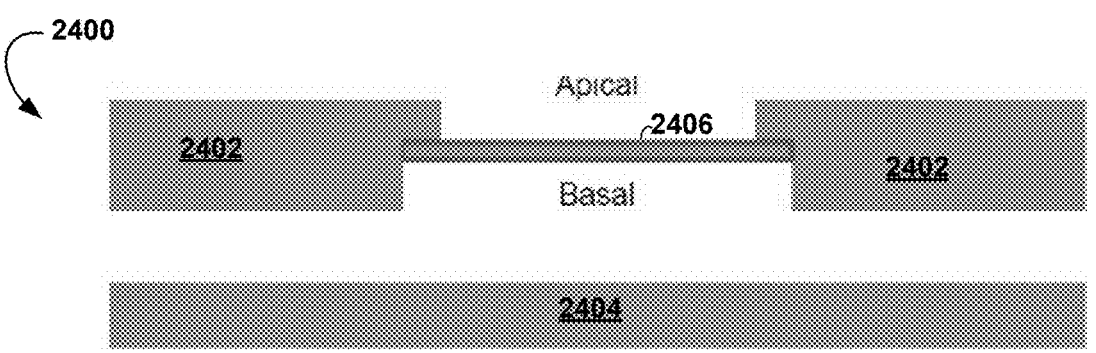
FIGS. 24A-D shows illustrations of side-views of a multi-compartment cell chamber of a microfluidic chip including different bonding configurations.

FIGS. 24A-D shows illustrations of side-views of a multi-compartment cell chamber 2400 of a microfluidic chip including different bonding configurations. The cell chamber 2400 can be included in any of the two-compartment microfluidic chips described herein. The bonding is formed from a heat sealing process which seals the membrane into place. A taut membrane is formed without large wrinkles. FIG. 24A shows a first option for sealing the membrane 2406. The membrane 2406 is first sealed to the apical portions 2402 of the thermoplastic (e.g., COC or PC). The bottom layer 2404 on the basal side of the membrane 2406 is then diffusion bonded to the apical portions 2042. This process provides precise control over the apical membrane surface area. No cover or additional pieces are required, and the cell chamber 2400 is monolithic.

Figure 24B:
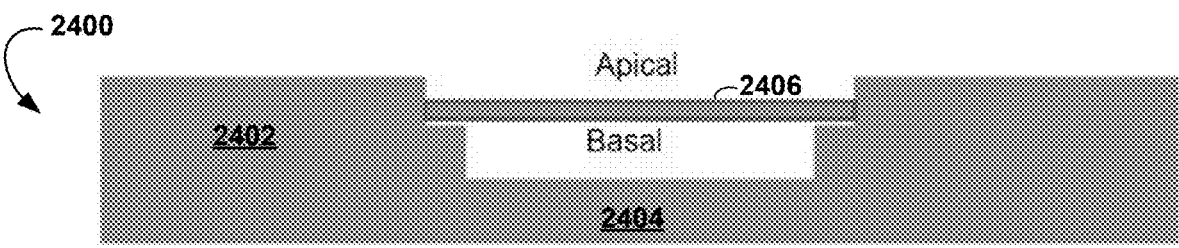

FIG. 24B shows a second option for sealing the membrane 2406 in the cell chamber 2400. The apical layer 2402 and the basal layer 2404 are diffusion bonded first. After the bonding is completed, the membrane 2406 is heat sealed to the apical layer 2402 from the apical side. This approach reduces a risk to damaging the membrane 2406 from the diffusion bonding of the apical layer 2402 to the basal layer 2404. No cover or additional pieces are required, and the cell chamber 2400 is monolithic.

Figure 24C:
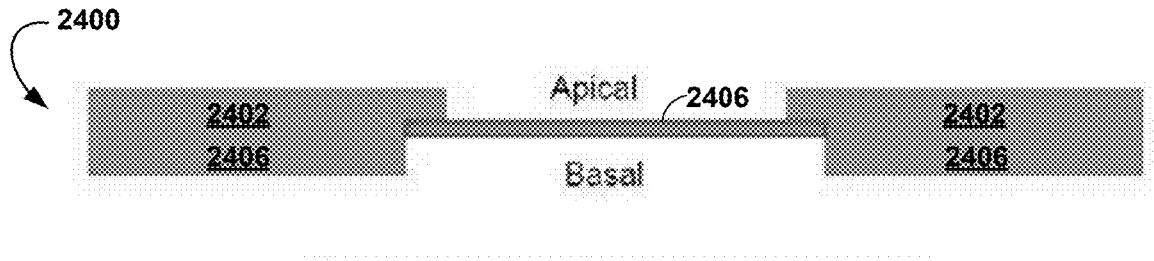

FIG. 24C shows a third option for bonding the membrane 2406 in the cell chamber 2400. The apical layer 2404 and basal layer 2406 are diffusion bonded. Then the membrane 2406 is heat sealed from the basal side of the bonded layer. Last, a cover 2410 is added to the cell chamber 2400. This process provides precise control of the apical surface area of the membrane 2406.

Figure 24D:
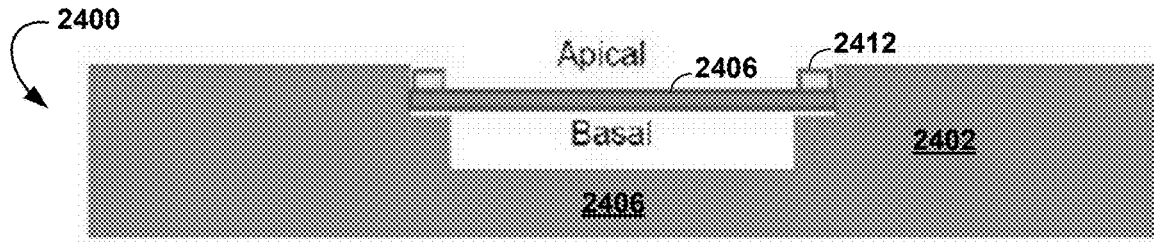

FIG. 24D shows a cell chamber 2400 with a fourth option for bonding the membrane 2406 to the chamber. The apical layer 2404 and basal layer 2406 are diffusion bonded. The membrane 2406 is heat sealed into place from the apical side of the cell chamber 2400. An additional insert 2412 is added to cover the portion of the membrane 2406 on the apical side which is covered on the basal side by the basal layer. This approach enables the easier apical membrane bonding approach with precise control over the size of the apical surface area of the membrane 2406. The insert 2412 can be conditioned to prevent cells from seeding onto the insert. The cell chambers are configured to be insertable and removable from the rest of the microfluidic chip.

Figure 25:
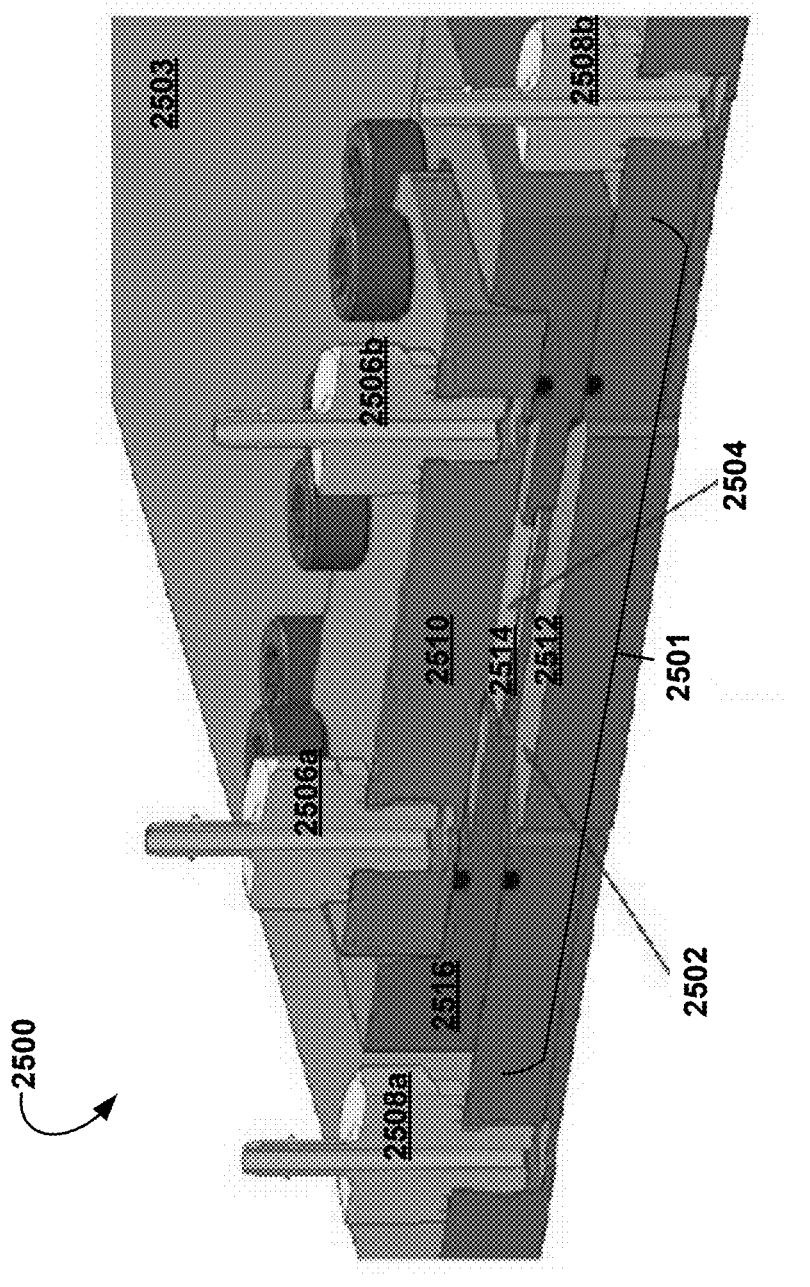
FIG. 25 shows an illustration of a perspective view of layers of a microfluidic chip including a multi-compartment cell chamber of a cell chamber insert.

FIG. 25 shows an illustration of a perspective view of layers of a portion of a microfluidic chip 2500 including a multi-compartment cell chamber insert 2501. The cell chamber insert 2501 includes a basal channel 2502 and an apical channel 2504 separated by a membrane 2514. The cell chamber insert 2501 can be formed as described in relation to FIGS. 24A-D. A substrate 2503 supports the cell chamber wall 2516.

The cell chamber insert 2501 is connected to a first apical port 2506a and a second apical port 2506b for fluid media flowing through the apical channel 2504. The first apical port 2506a and second apical port 2506b can be connected to the pump for apical fluid media flow or fluid media recirculation. In some implementations, the first apical port 2506a can enable sampling the fluid media received from the apical channel 2504 during recirculation of fluid media through the apical channel. In some implementations, the second apical port 2506b can enable sampling of the fluid media prior to entry into the apical channel 2504. Thus, the fluid media can be sampled on either side of the apical channel 2504 and the results compared. For example, sampling fluid media on either side of the apical channel 2504 can enable a determination of how the fluid media is changed while flowing through the apical channel, such as changes to an oxygen or a drug concentration level in the fluid media.

The cell chamber insert 2501 is connected to a first basal port 2508a and a second basal port 2508b for fluid media flowing through the basal channel 2502 (if applicable). The first basal port 2508a enables sampling the fluid media received from the basal channel 2502, such as during recirculation of fluid media through the basal channel. The second basal port 2508*b* enables sampling of the fluid media prior to entry into the basal channel 2502. Thus, the fluid media can be sampled on either side of the basal channel 2502 and the results compared. For example, sampling fluid media on either side of the basal channel 2502 can enable a determination of how the fluid media is changed while flowing through the basal channel, such as changes to an oxygen or a drug concentration level in the fluid media.

In some implementations, the fluid media in basal channel 2502 is stagnant, and fluid media does not flow through the basal channel 2502 as part of a basal loop. In some implementations, the basal channel 2502 fluid media is recirculated, and fluid flows through the basal channel. In some implementations, the basal channel 2502 includes fluid flow by a separate pump form the apical channel or by a same pump as the apical channel.

The compartments 2514, 2512 of the cell chamber each has a precise geometry for generating a particular oxygen gradient within tissue seeded in each of the basal channel 2502 and the apical channel 2504. A precise geometry includes a specific height, width, depth, or shape for the cell chamber compartments 2512, 2514 as configured for hosting a particular type of tissue in the cell chamber. As previously discussed, the cell chamber 2501 is configured to emulate conditions for tissue, such as human tissue, within the cell chamber, including a particular oxygen concentration within the fluid media. A cell chamber wall layer 2516 forms the removable frame of the insert 2501. This can be transferred to and from the rest of the microfluidic chip, e.g., before and after experimentation. The cell chamber wall layer 2516 also forms the geometry of the cell chamber walls for each of the apical channel 2504 and the basal channel 2502 In some implementations, each of the apical channel 2504 and the basal channel 2502 include a waterfall feature that enables faster flow rates of the fluid media, and therefore oxygen concentration over a particular threshold level, while also preventing shear stress on the tissue from exceeding a threshold value.

Figure 26:
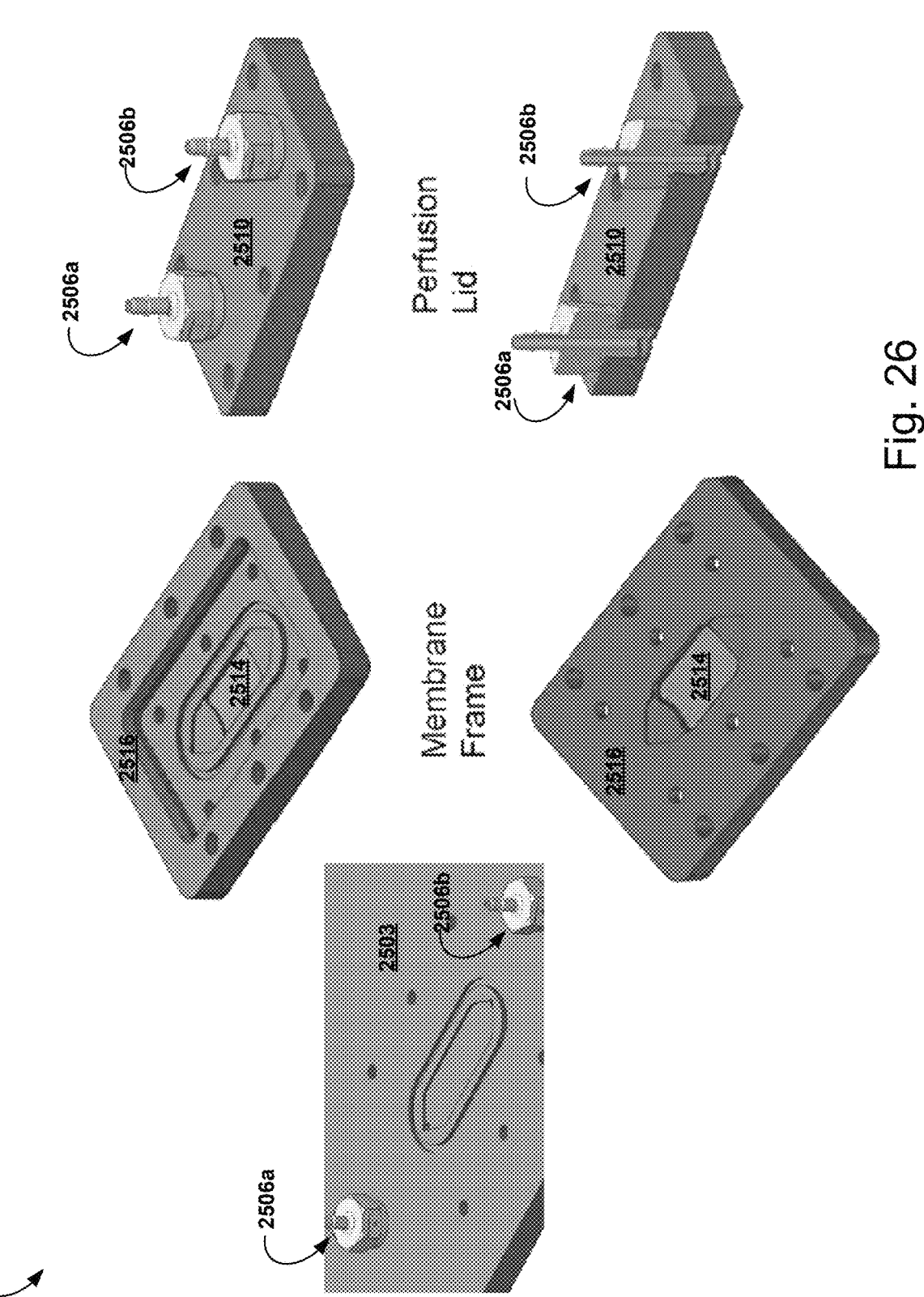
FIG. 26 shows an illustration of portions of the cell chamber of the microfluidic chip of FIG. 25.

FIG. 26 shows an illustration of portions of the cell chamber insert 2501 of the microfluidic chip of FIG. 25. The cell chamber wall layer 2516 forms the shape of the cell chamber and supports the membrane 2514. The membrane 2514 can be bonded to the cell chamber wall layer 2516 as described in relation to FIGS. 24A-D. The cell chamber cover 2510 is fastened to the cell chamber wall layer 2516 using fasteners. The cell chamber cover 2510 supports apical channel ports 2506*a-b*. The substrate 2503 supports the basal ports 2508*a-b*.

Figures 27A, 27B, 27C:
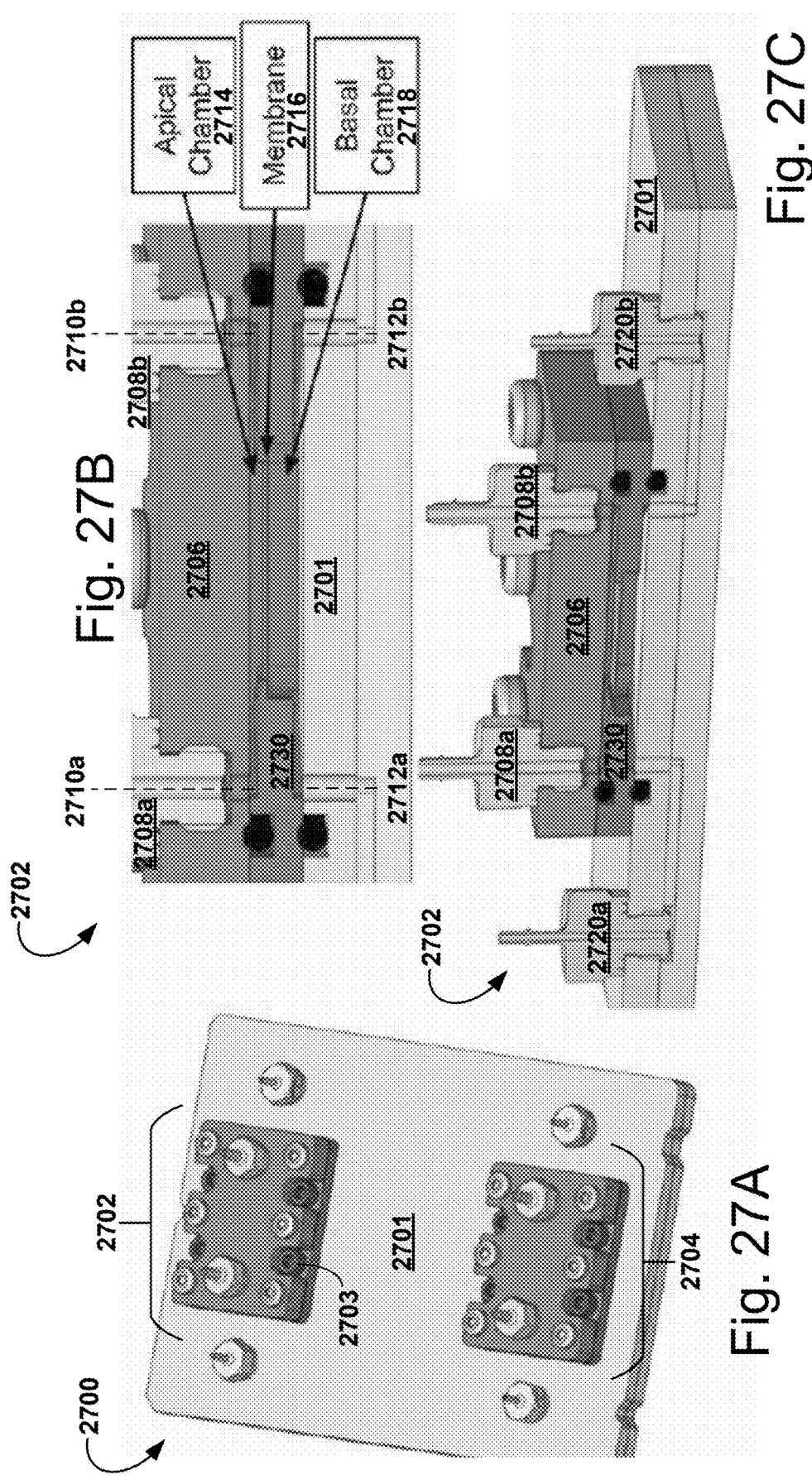
FIG. 27A shows an illustration of a perspective view of layers of a microfluidic chip including multiple instances of multi-compartment cell chamber insert.
FIG. 27B shows illustrations of portions of the multi-compartment chamber of FIG. 27A.
FIG. 27C shows an illustration of an embodiment of the multi-compartment chamber of FIG. 27A

FIG. 27A shows an illustration of a perspective view of layers of a microfluidic chip 2700 including a plurality of multi-compartment chamber inserts 2702, 2704. The microfluidic chip 2700 shows two cell chamber inserts 2702, 2704 that are each connected to a common substrate 2701. In some implementations, the microfluidic chip 2700 is configured to host different types of tissues, each type of tissue being hosting in a respective modular cell chamber 2702, 2704 insert. Each cell chamber 2702, 2704 insert is removable and replaceable with other cell chambers (not shown). Each cell chamber insert 2702, 2704 can have a different cell chamber geometry that is specialized for a particular type of tissue to be hosted within the cell chamber. In some implementations, the multi-compartment cell chambers 2702, 2704 are identical instances each configured to host a same type of tissue. The instances of the cell chambers 2702, 2704 can be disposable. For example, each cell chamber 2702,

2704 can be removable from the substrate 2701 by fasteners, such as fastener 2703. If a cell culture fails in a particular cell chamber 2702, 2704, the cell chamber can be replaced without replacement of the remaining components in the microfluidic chip 2700.

FIG. 27B shows illustrations of portions of the multi-compartment insert 2702 of FIG. 27A. The multi-compartment cell chamber inserts 2702, 2704 are each configured to host tissue (e.g., human tissue) for emulation of an in vitro environment for that tissue. The cell chamber 2702 includes an apical chamber 2714 and a basal chamber 2718 separated by a membrane 2716. The cells of the tissue are seeded onto the membrane 2716. The membrane 2716 can be sealed as described with respect to FIGS. 25A-D. The membrane forms a porous barrier between the apical chamber 2714 and the basal chamber 2718. The membrane supports the cells seeded either side of the membrane. In some implementations, either side of the membrane can be coated with extracellular matrix (e.g. collagen) and the cells can adhere to the membrane. The attachment helps to cells to be polarized. (e.g. proximal tubule cells). In some implementations, the membrane 2716 is permeable or semi-permeable. In some implementations, the tissue covers the entire membrane 2716 to form the barrier between the basal chamber 2718 and the apical chamber 2714. For example, the tissue can be seeded onto the membrane 2716 and receive fluid media from each of the apical chamber 2714 and the basal chamber 2718. At the same time, the tissue prevents the fluid media of the apical chamber 2714 from entering the basal chamber 2718 and vice versa.

FIG. 27C shows an illustration of an embodiment of the multi-compartment chamber insert 2702 of FIG. 27A. A cover 2706 forms a top layer of the cell chamber 2702 and seals the apical chamber 2714. The substrate 2701 seals the basal chamber 2718 of the cell chamber 2702. Apical ports 2708*a-b* enable sampling to be performed on either side of the apical chamber 2714. Basal ports 2720*a-b* enable sampling to be performed on either side of the basal chamber 2718. In some implementations, the cell chamber 2702 is top-mounted onto the substrate 2701, as shown in FIGS. 27A-C.

The apical ports 2708*a-b* each have a respective passageway 2710*a-b*. The passageway 2710*a-b* enable sampling and/or perfusion through the cover 2706 for a top-mounted cell chamber 2702. The basal passageways 2712*a-b* allow the basal fluid media to flow to respective basal ports 2710*a-b* for sampling around the basal chamber 2718.

Figure 27D:
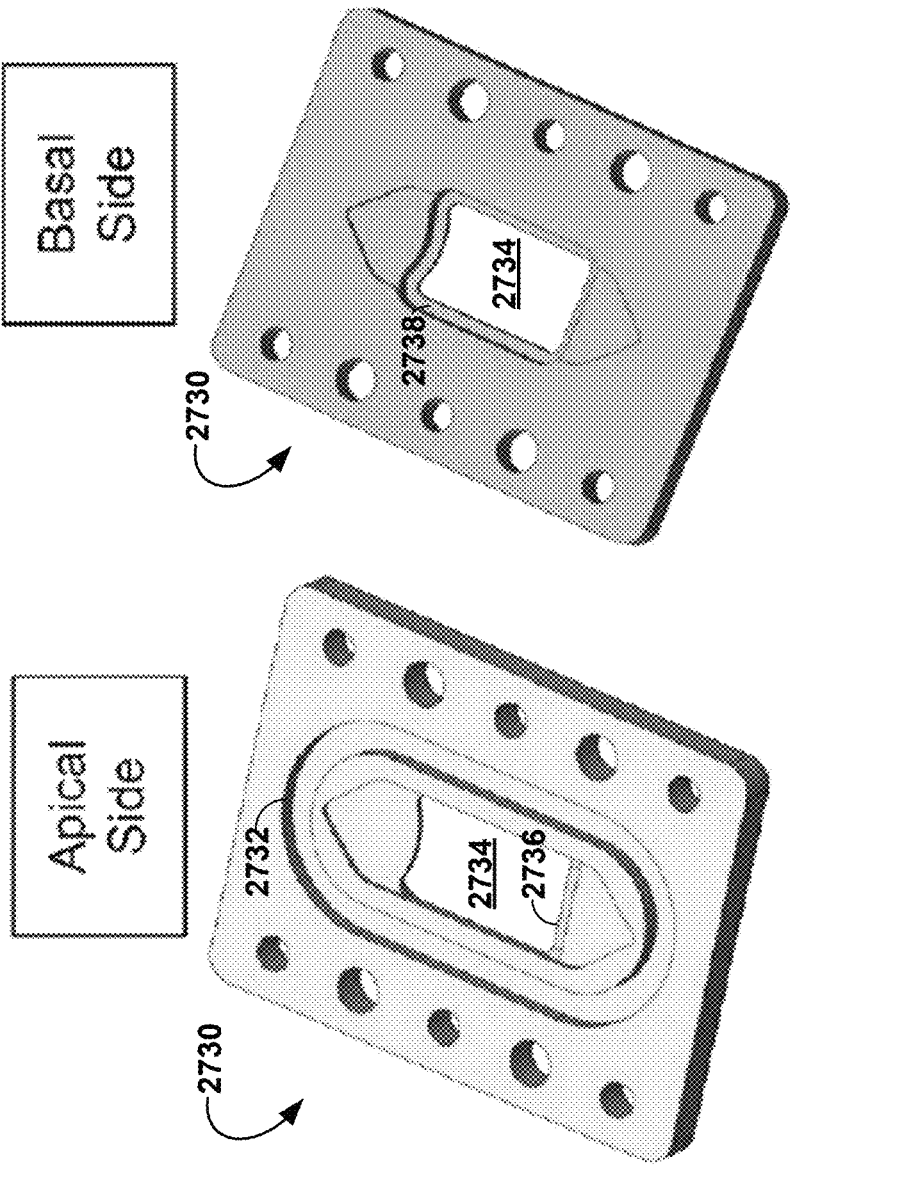
FIG. 27D shows an illustration of layers of the multi-compartment cell chamber insert of FIG. 27A.

FIG. 27D shows an illustration of a cell chamber wall 2730 of the multi-compartment cell chamber of FIG. 27A. The cell chamber wall 2730, also called a frame, is a cell wall layer for the cell chamber 2702. An apical side shows a channel 2732 for a seal (e.g., an O-ring) for sealing the apical chamber 2714. A gap 2734 enables a positioning of a membrane 2716 for acting as a permeable or semi-permeable barrier between the apical chamber 2714 and the basal chamber 2718. As previously indicated, the tissue is seeded onto the membrane. In the apical side, a waterfall feature 2736 is included to enable higher flow rates for the fluid media without causing shear stresses on the tissue to exceed a desirable threshold. The basal side of the cell chamber wall layer 2730 includes a shelf 2738 for sealing the membrane. The gap 2734 for the membrane is surrounded by the shelf 2738.

Figure 27E:
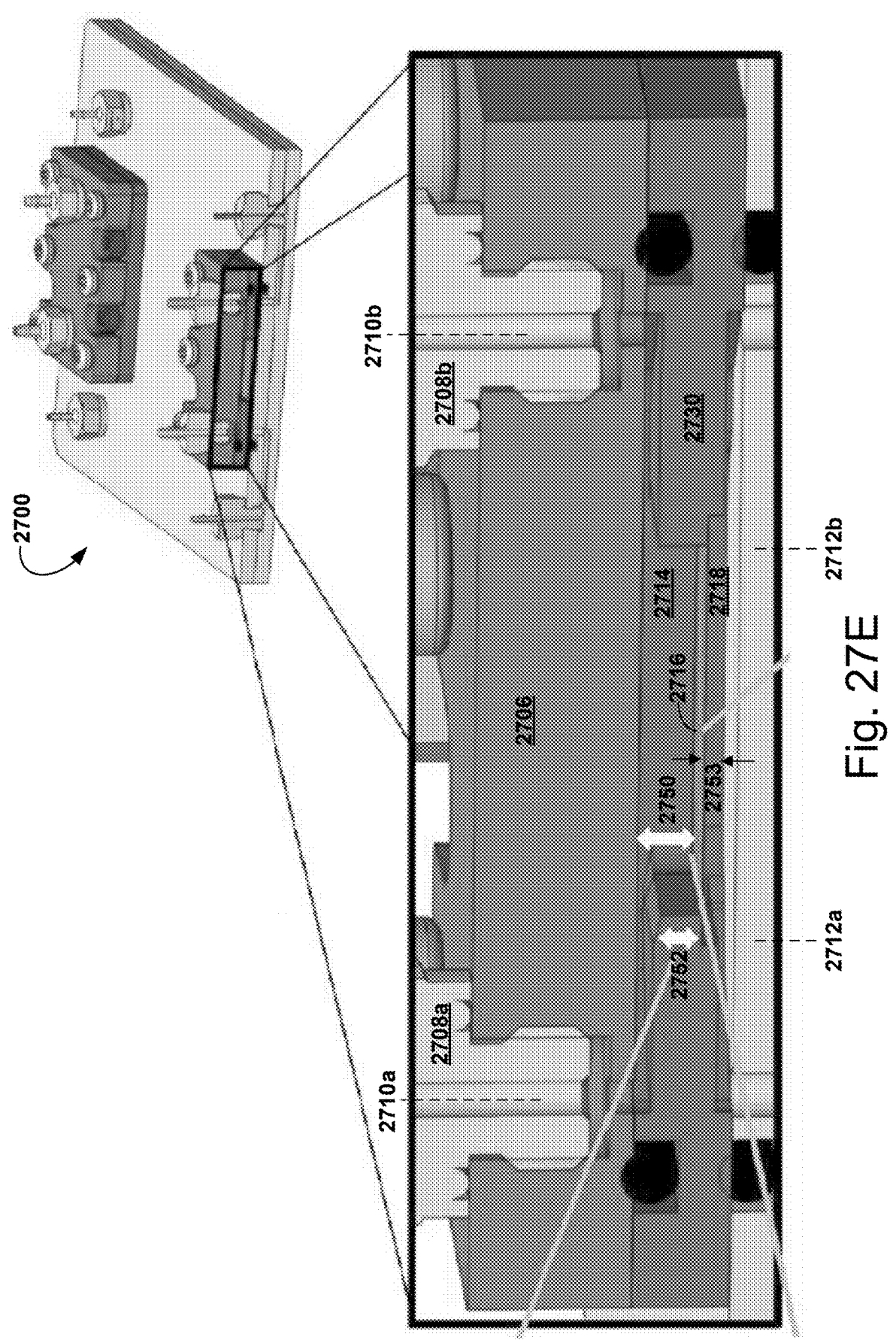
FIG. 27E shows a zoomed-in side-view of the cell chamber insert of the microfluidic chip.

FIG. 27E shows a zoomed-in side-view of the cell chamber insert 2702 of the microfluidic chip 2700. The cell chamber wall 2730 includes a heat seal shelf 2752. The cell chamber wall 2730 defines the apical chamber 2714 height 2750. The cell chamber wall 2730 enables heat sealing of the membrane 2716 without wrinkling the membrane. The heat seal shelf 2752 height is 1.5 mm. The apical chamber height 2752 is 2 mm. The basal channel height 2753 is 1 mm. This configuration reduces shear forces on the tissue in the apical chamber 2714 such that four times the flow rate causes a similar shear in comparison to an apical chamber having a height of 1 mm. For example, in another embodiment, the apical chamber height 2750 is 1 mm, the basal chamber height 2753 is 2 mm, and the heat seal shelf is 1 mm.

As previously discussed, the membrane 2716 provides attachment support for barrier tissues (e.g., endothelial and epithelial), to enable study of drug transport from the apical to basal side (or vice versa). Tissue types can include, for example, gut, kidney, or lung types. In some implementations, multicellular liver tissue can be constructed. For example, epithelial cells can be seeded on the apical side of membrane 2716, and liver sinusoidal endothelial cells (LSECs) can be seeded on the basal side of membrane 2716 under high shear flow. In some applications, if the tissue is seeded to apical side and flow is only on the basal side (or vice versa), the membrane 2716 assists in reducing shear forces on the tissue. The tissue can be seeded onto the membrane 2716 in the apical chamber 2714 or basal chamber 2718 (or both). In some implementations, the tissue is seeded inside a gel. The gel facilitates handling of the cell culture during the seeing process and increases a likelihood of a successful culture within the apical/basal compartments 2714, 2718 of the cell chamber insert 2702.

Figure 28:
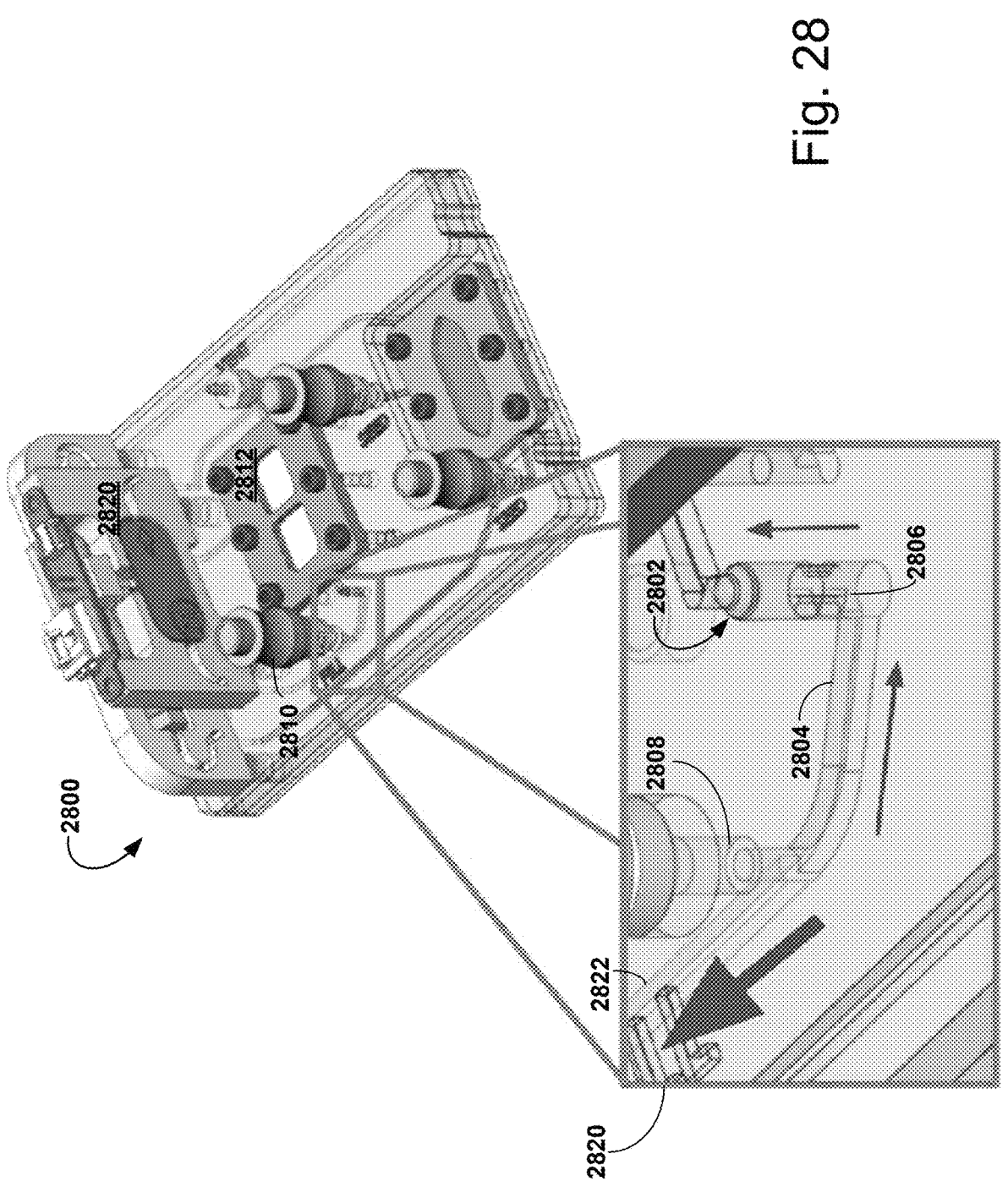
FIG. 28 shows an illustration of a valve for a media injection port of an example microfluidic chip of any of the foregoing figures.
Figures 29A, 29B:
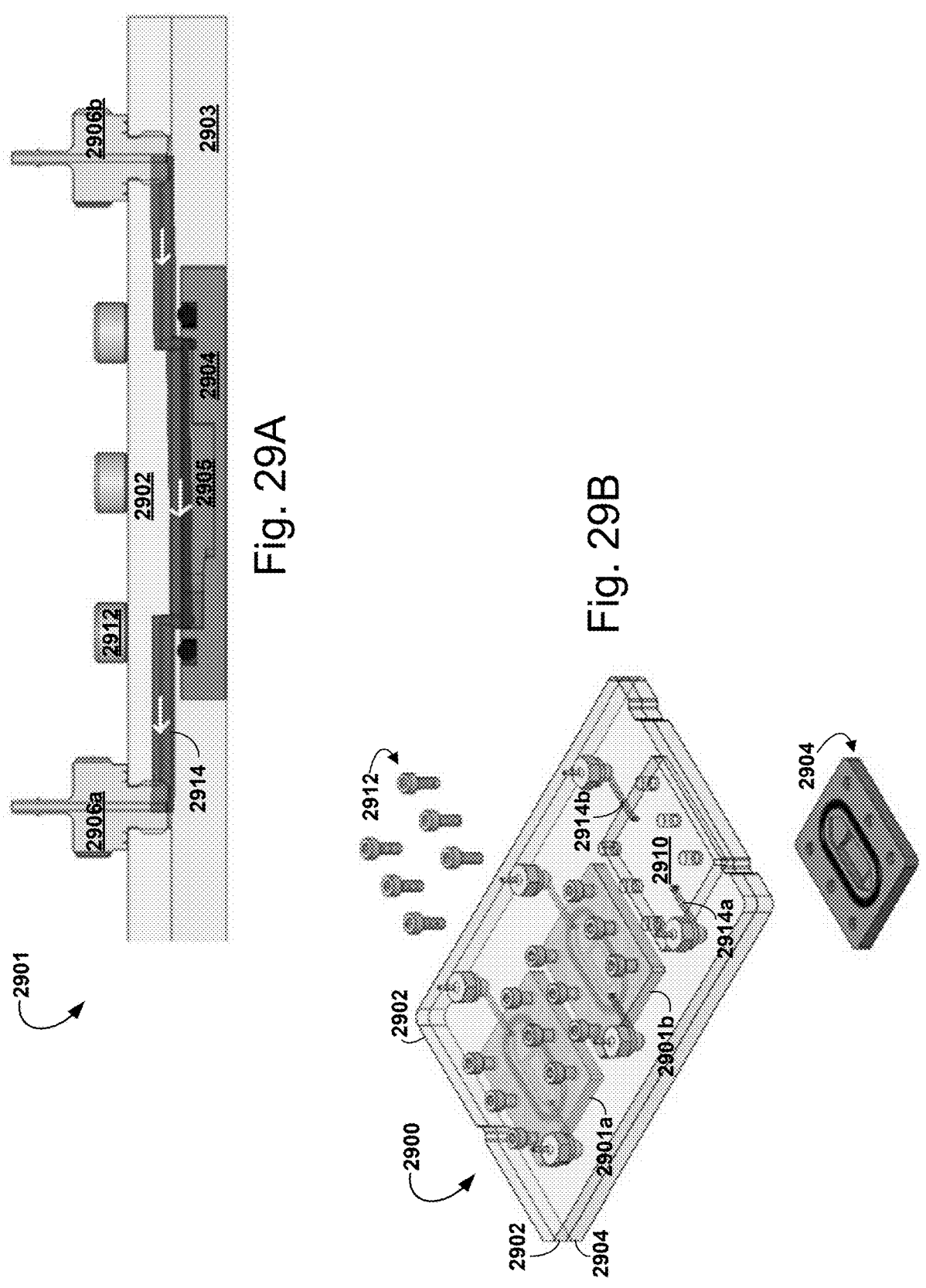
FIG. 29A shows an illustration of a side view of an example of a multi-chamber microfluidic chip cell chamber insert.
FIG. 29B shows an illustration of an exploded perspective view of an example of a multi-chamber microfluidic chip including the cell chamber of FIG. 29A, the microfluidic chip for combining different tissue types.

FIG. 28 shows an illustration of a valve for a media injection port 2810 of an example microfluidic chip 2800 of any of the foregoing figures. A zoomed-in portion 282— shows the channels 2822, 2804 connected to the injection port channel 2808. The media injection port 2810 enables a user to add or remove fluid media from the recirculating fluid loop of the microfluidic chip 2800. The media injection port 2810 includes a check valve 2802 that prevents air from entering the fluid loop when fluid media is being added to prime the fluid pump 2820. The check valve can include a ball valve 2806 that prevents air or fluid from moving back along channel 2804 into the recirculating chamber 2812. Fluid that is injected into the fluid loop moves along path 2820 toward the pump FIG. 29A shows an illustration of a side view of an example of a microfluidic chip cell chamber insert 2901 for a microfluidic chip 2900 for combining different tissue types. FIG. 29B shows an illustration of an exploded perspective view of an example of a multi-chamber microfluidic chip 2900 including the cell chamber 2901, the microfluidic chip 2900 for combining different tissue types in respective instances 2901a-c of the cell chamber. The multi-chamber microfluidic chip 2900 includes multiple instances of modular cell chamber 2901 inserts (such as cell chamber inserts described previously) on a single microfluidic chip 2900. The microfluidic chip 2900 shown in FIG. 29A is a portion of a full microfluidic chip system and is a portion of a recirculating fluid loop, but only the cell chamber instances 2901a-b are shown for simplicity.

Each modular cell chamber insert 2901 can be mounted in a port 2910 on the microfluidic chip 2900. In some implementations, the cell chambers are bottom mounted, as shown in FIG. 29B. The cell chambers 290a-b are each mounted with fasteners 2912. Channels 2914a-b are connected to ports 2906a-b for sampling fluid media up-flow and down-flow from the cell chamber 2901. The bottom-mounted modular cell chamber 2901 insert is formed by mounting the frame or cell chamber wall piece 2904 from underneath the substrate 2903 using fasteners 2912. The flow path 2914 across channels 2914a-b and the cell chamber channel 2905 traverses across the modular chamber below the top layer 2902.

Figure 30A:
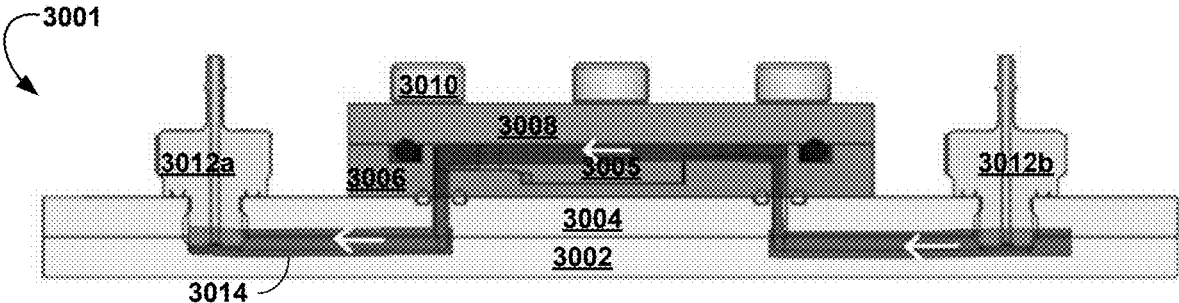
FIG. 30A shows an illustration of a side view of an example of a multi-chamber microfluidic chip cell chamber.
Figure 30B:
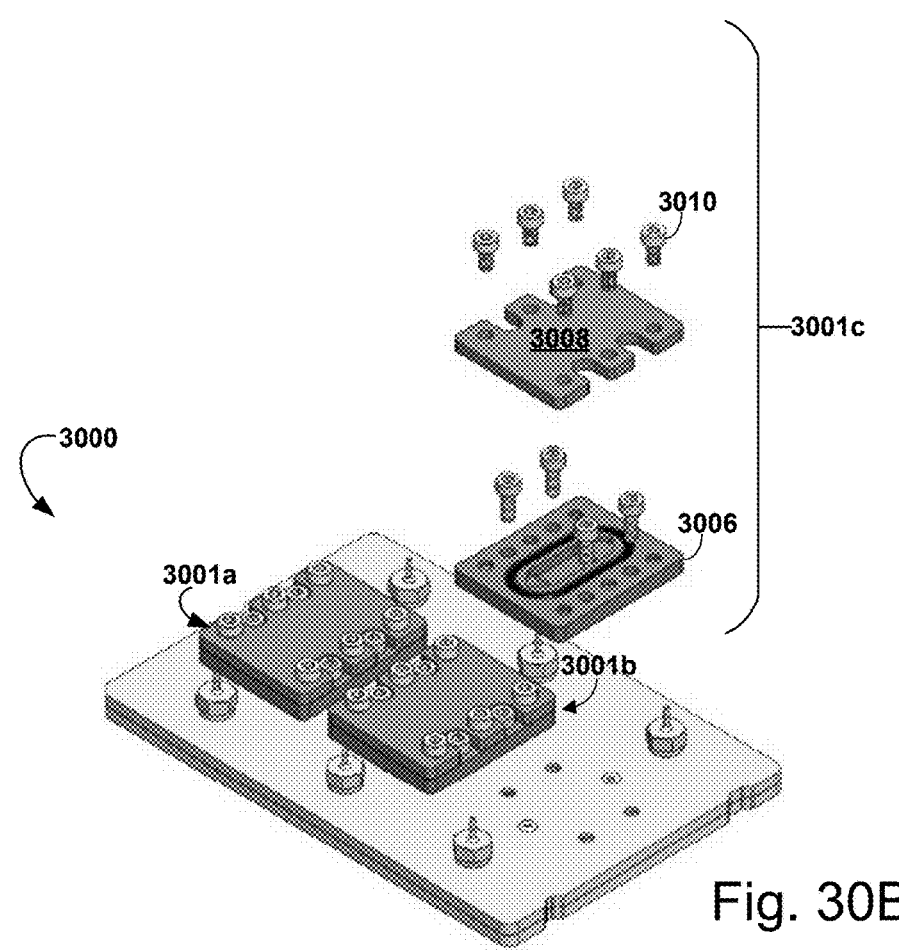
FIG. 30B shows an illustration of an exploded perspective view of an example of a multi-chamber MPS including the cell chamber of FIG. 30A, the microfluidic chip for combining different tissue types in different cell chamber inserts.

FIG. 30A shows an illustration of a side view of an example of a multi-chamber microfluidic chip cell chamber 3001. FIG. 30B shows an illustration of an exploded perspective view of an example instance of a multi-chamber microfluidic chip 3000 including the cell chamber insert 3001, the microfluidic chip 3000 configured for combining different tissue types using modular cell chamber insert instances 3001a-c. The cell chamber insert 3001 includes ports 3012a-b for sampling the fluid media up-flow and down-flow of the cell chamber channel 3005. The cell chamber 3001 includes a bottom layer 3014, a substrate 3004, a cell chamber wall layer 3006, and a cover 3008. In this example, the cell chamber insert 3001 is mounted to the top of the substrate 3004 of the microfluidic chip 3000. The cell chamber insert 3001 sits on top of the bottom layer 3002 and the substrate 3004. Fasteners 3010 secure the cover and cell chamber wall layer 3006 to the substrate 3004. A flow path 3014 goes up and over the substrate 3004, through the channel 3005, and down back under the substrate 3004.

Figure 31:
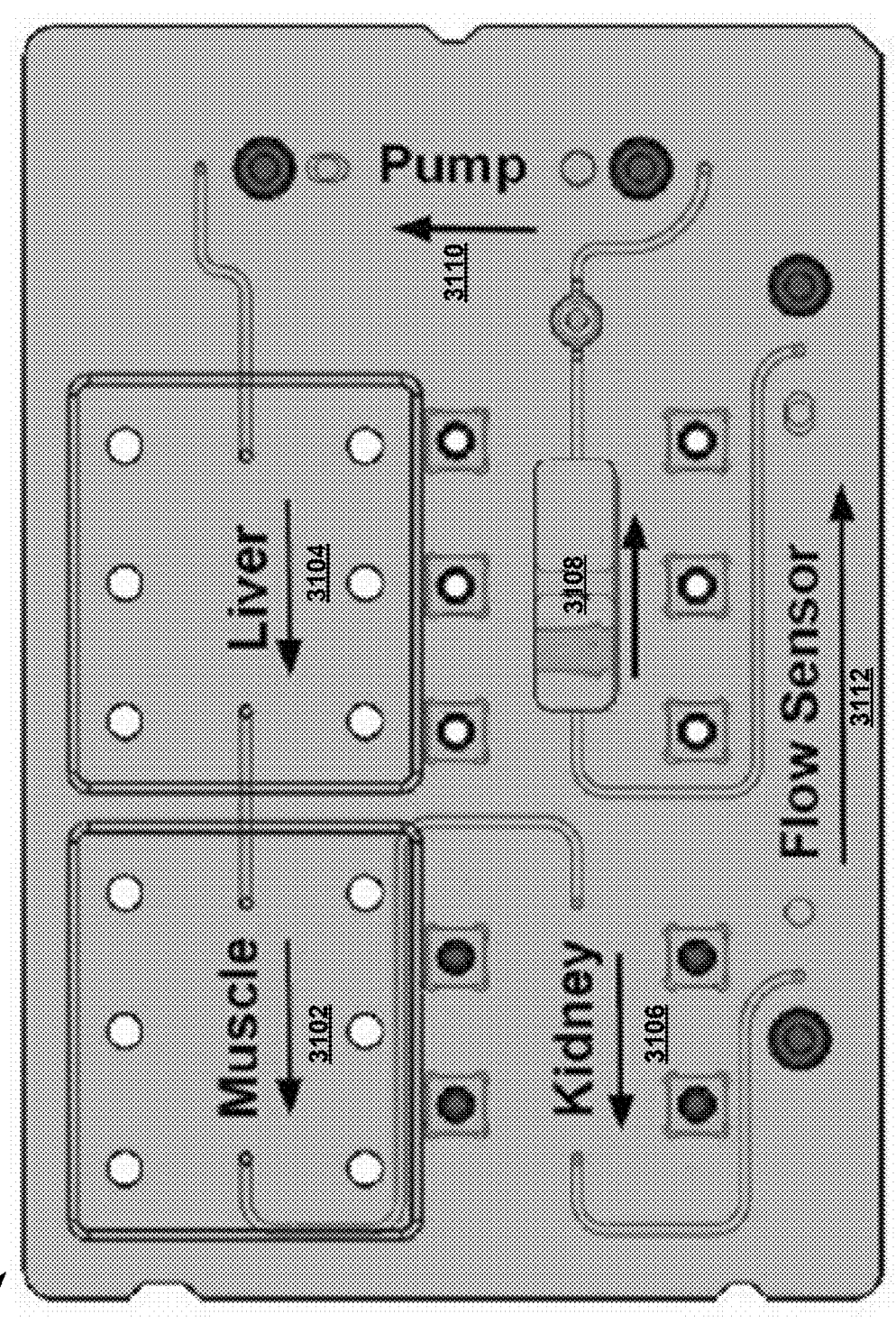
FIG. 31 shows an example of a layout for a multi-chamber microfluidic chip for combining different tissue types in different cell chamber inserts.

FIG. 31 shows an example of a layout for a multi-chamber microfluidic chip 3100 for combining different tissue types. Each of the cell chambers can be designed differently for a particular tissue type. For example, the microfluidic chip 3100 can include a multi-component chamber insert for a liver, and a single component chamber inset for muscle tissue. In some implementations, the muscle cell chamber can be optimized for cells embedded in a gel, while other cell chambers have cells seeded directly on a membrane or chamber wall. The microfluidic chip 3100 includes three different cell chambers, each hosting a different cell type. The microfluidic chip 3100 includes a liver cell chamber 3104, a muscle cell chamber 3102, and a kidney cell chamber 3106, each which can be included in a respective insert. A single re-oxygenation chamber 3108, is configured to add oxygen to the fluid loop as previously described. A single pump 3110 is configured to pump the fluid media through each of the cell chambers 3102, 3104, and 3106, the re-oxygenation chamber 3108, the optional flow sensor 3112, and each of the microfluidic channels connecting these elements. Generally, the multiple cell chambers are each in sequence in a single recirculation loop. In some implementations, the microfluidic chip includes apical flow to barrier function using a second pump. In some implementations, the insert is a single compartment (e.g., for liver tissue) or a dual compartment (e.g., for kidney tissue). For example, dual-single-dual in gut-liver-kidney configuration can be used for oral drug studies. For example, a lung-airway-liver-kidney configuration can be assembled for inhalation formulations. For example, a skin-liver-kidney configuration can be assembled for topical formulation. A two-organ set-up configuration can be assembled. Other such configurations are possible with different tissue types and insert types reconfigured in different orders in the fluid loop(s) as desired.

In the microfluidic chip 3100, the order of the cell chambers is shown such that the liver cell chamber 3104 is first after the re-oxygenation chamber 3108. In this example, the liver cell chamber 3104 is the first tissue to receive oxygenated fluid media. Because liver tissue requires more oxygen than muscle or kidney tissue, the liver cell chamber 3104 is positioned first in the sequence. The muscle cell chamber 3102 that hosts muscle tissue is positioned second after the re-oxygenation chamber 3108. The kidney cell chamber 3106 that hosts kidney tissue is the third cell chamber in the sequence after the re-oxygenation chamber 3108. Each of the cell chambers 3102, 3104, and 3108 can be either-top mounted or bottom-mounted, as described previously. Generally, the inserts can be changed in size or mentations, the surface area of well (e.g., well 2204*a-b*) is 1 cm$^2$. In some implementations, the cell chamber total height is 2 mm. Examples of specific dimensions are provided in Table 3.

TABLE 3

| Example Dimensions for a single channel of microfluidic chip 3300 | | | | |
|---|---|---|---|---|
| Category | Surface Area [mm^2] | Height [mm] | Volume (mm^3) | Volume (mL) |
| Re-oxygenation chamber | 196.60 | 2.00 | 393.20 | 0.39 |
| Cell Channel (Cell Area and Above) | 100.00 | 3.00 | 300.00 | 0.30 |
| Cell Channel (Waterfall inlet) | 43.39 | 1.00 | 43.39 | 0.04 |
| Cell Channel (Waterfall outlet) | 38.17 | 2.00 | 76.34 | 0.08 |
| Paths | 212.20 | 1.00 | 212.20 | 0.21 |
| Fittings to Pump | N/A | N/A | 209.10 | 0.21 |
| Pump | N/A | N/A | 76.58 | 0.08 |
| Other ports collection area | N/A | N/A | 58.90 | 0.06 |
| Total Recirc | | | 1,369.71 | 1.37 |
| Access Ports | N/A | N/A | 94.25 | 0.09 |
| Total Dead Volume | | | 94.25 | 0.09 |
| Total Chip Volume | | | 1,463.95 | 1.46 | geometry to accommodate different tissue types. In some implementations, the same inset geometry can be used to support different tissue types in different instances of the insert. The order can be changed to any combination or order as desired for the experiment.

Figure 32B:
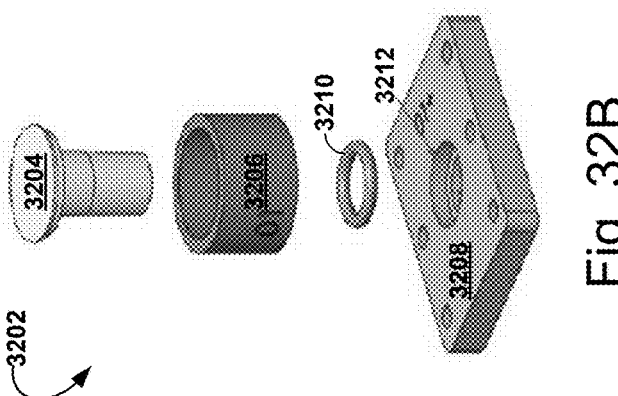
FIGS. 32A-C show examples of a transwell adapter for a microfluidic chip insert.
Figure 32A:
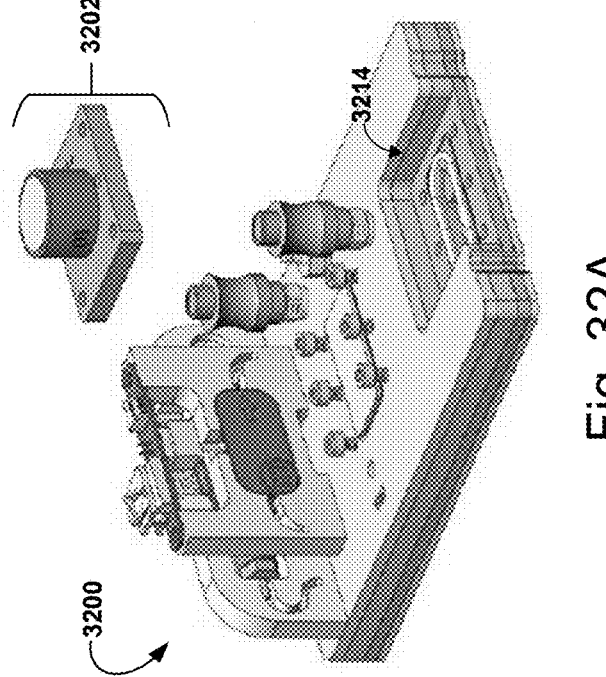
Figure 32C:
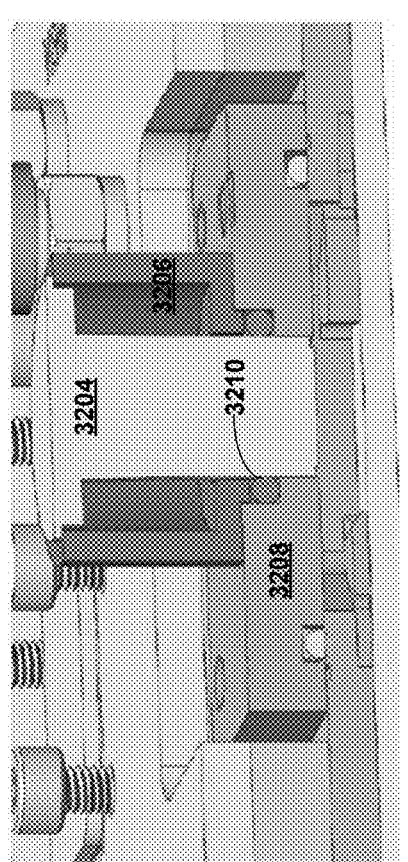

FIGS. 32A-C show examples of a transwell adapter 3202 for a microfluidic chip 3200. Generally, cells are seeded and cultured statically on a transwell and then transferred to the recirculating microfluidic chip 3200. The adapter 3202 holds the transwell tight during the basal perfusion. The drug samples can be collected on either side. Generally, the frame inserts are perfusable version of conventional transwells (static).

The adapter 3202 receives a transwell 3204 by a sheath 3206. A cover 3208 is coupled to a seal 3210 to seal the adapter to the cover. The cover 3208 is similar to the covers previously described, and includes a cutout portion 3212 to receive the sheath 3206. FIG. 32A shows an example of the transwell adapter 3202 attached to the cover 3028 removed from the cell chamber cavity 3214 that hosts the cell chamber. FIG. 32B shows an exploded view of the transwell adapter. FIG. 32C shows a side-view including a cross-section of the transwell adapter 3202. Generally, the transwell adapter 2302 is configured to interface with a cell chamber insert.

Figure 33:
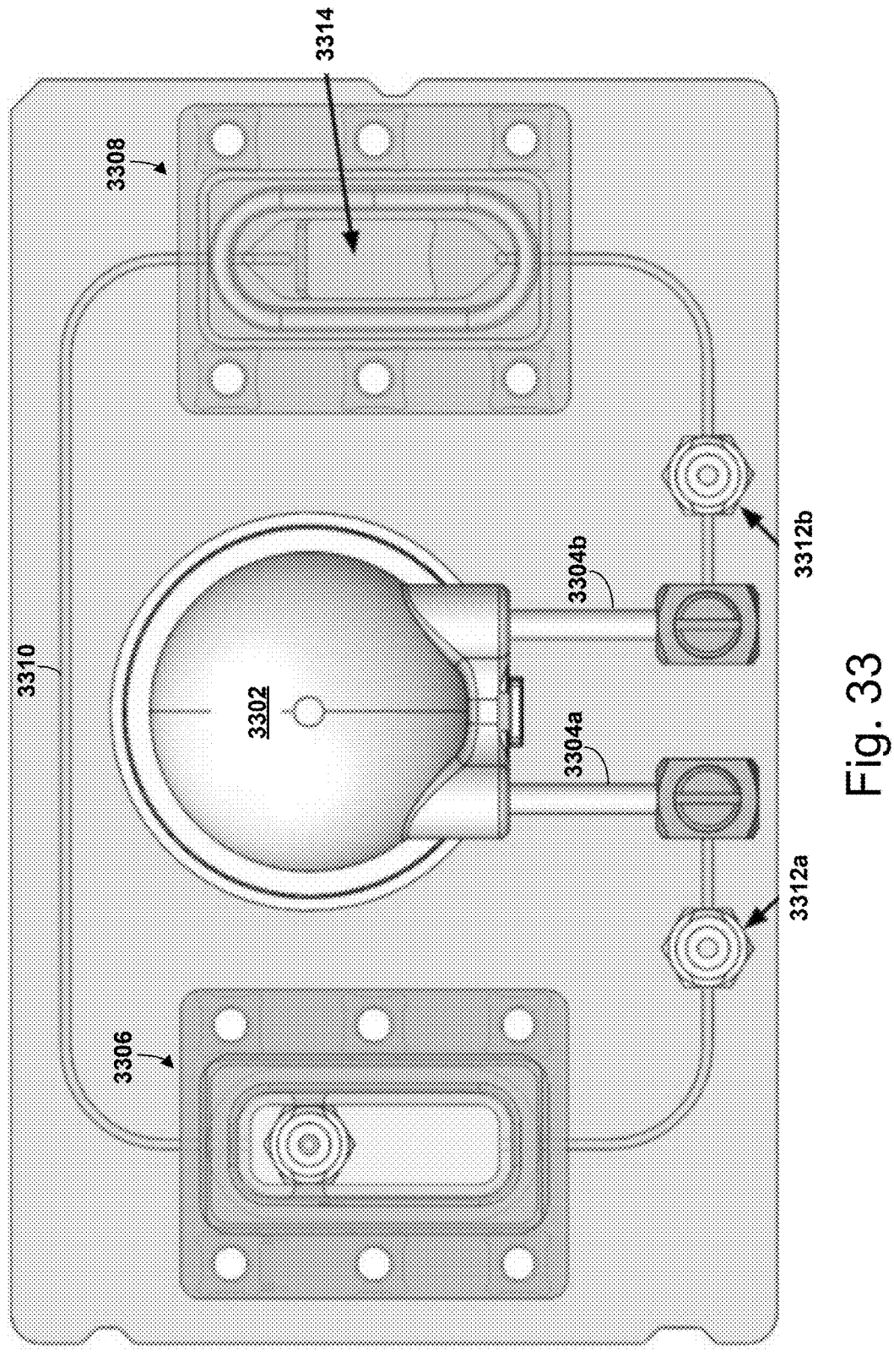
FIG. 33 shows a bottom view of an example microfluidic chip including a peristaltic pump.

FIG. 33 shows a bottom view of an example microfluidic chip 3300 including a peristaltic pump 3302. The microfluidic chip 3300 can be similar to the microfluidic chips previously described. The microfluidic chip 3300 includes an insert 3308 including a cell chamber 3314, similar to inserts previously described. The microfluidic chip 3300 includes a re-oxygenation chamber 3306, similar to re-oxygenation chambers previously described. The microfluidic chip 3300 includes microfluidic passages 3310 forming a fluid loop. A peristaltic pump 3302 is included to circulate the fluid media through the fluid loop. The peristaltic pump 3302 has ports 3304*a-b* for fluid intake and output. Access ports 3312*a-b* enable access to the fluid loop (e.g., for adding/removing fluid media). In some implementations, a channel feature (not shown) is added to smooth flow from the peristaltic pump 3302.

Figures 34A, 34B:
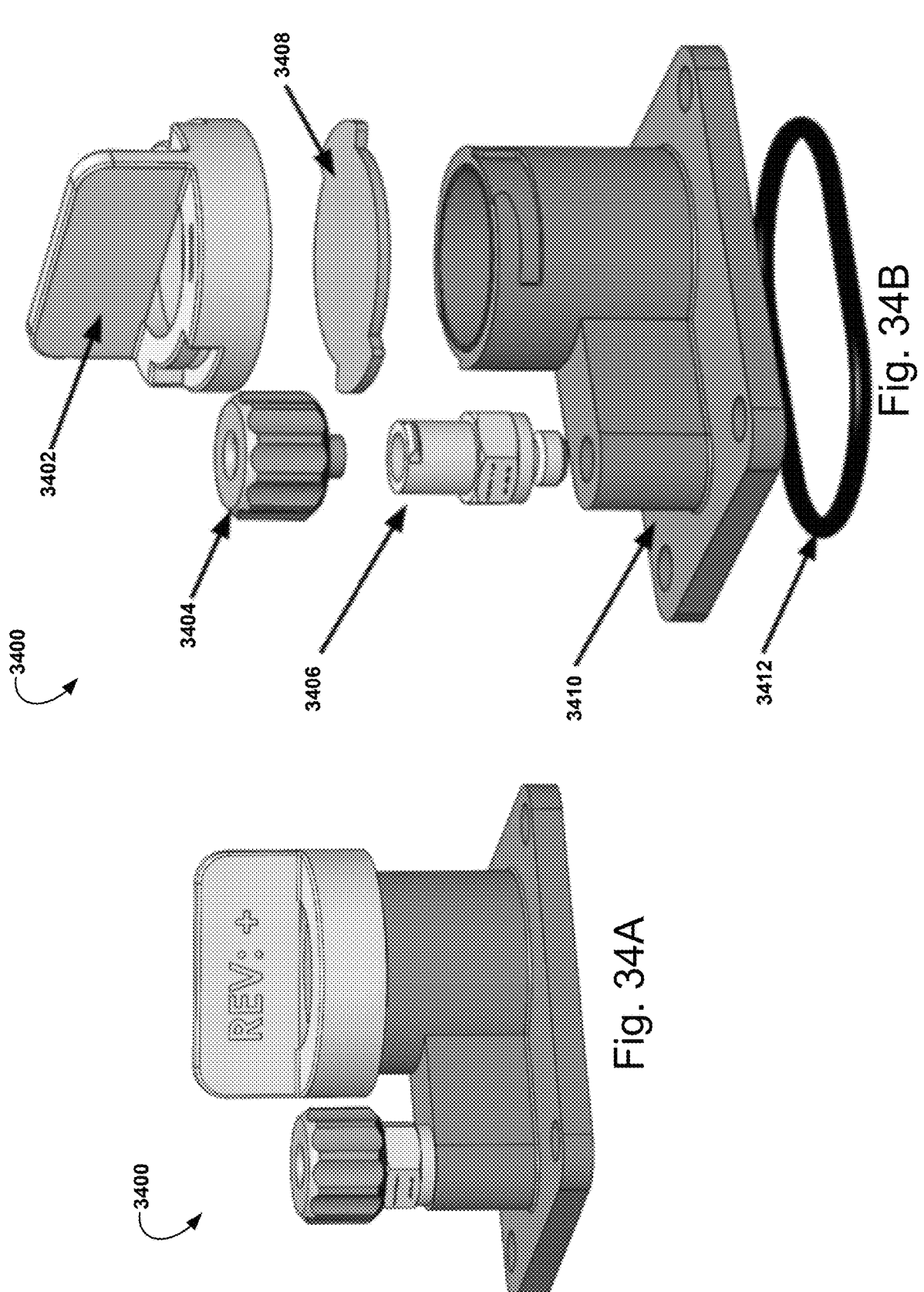
FIGS. 34A-B show perspective views of examples of a re-oxygenation chamber cover.

Example cell chamber dimensions are now described. In some implementations, the cell chamber channel total height (heights 2210, 2206, and 2210) is 3 mm. In some imple- FIGS. 34A-B show perspective views of examples of a re-oxygenation chamber cover 3400. The cover 3400 can be used to enable oxygenation of the re-oxygenation chambers described herein. The cover 3400 includes a membrane cap 3402, a vent cap 3404, an oxygenation chamber vent 3406, a membrane 3408, a frame 3410, and a seal 3412. The membrane cap 3402 covers the membrane when the microfluidic chip is not in use or is adding oxygen to the fluid loop. The cap 3402 protects the membrane 3408. The cap 3404 seals the vent 3406 if venting is not desired or when the re-oxygenation chamber is not being used. The cap 3404 can be twisted on/off or latched by another mechanical means. The vent 3406 enables air to vent from the oxygenation chamber. The frame 3410 provides a mechanical base for the membrane and helps to set an oxygenation rate for the fluid in the re-oxygenation chamber. The seal 3412 prevents air escaping from the fluid loop. The membrane 3408 allows a particular concentration of oxygen to enter the oxygenation chamber.

Figure 35:
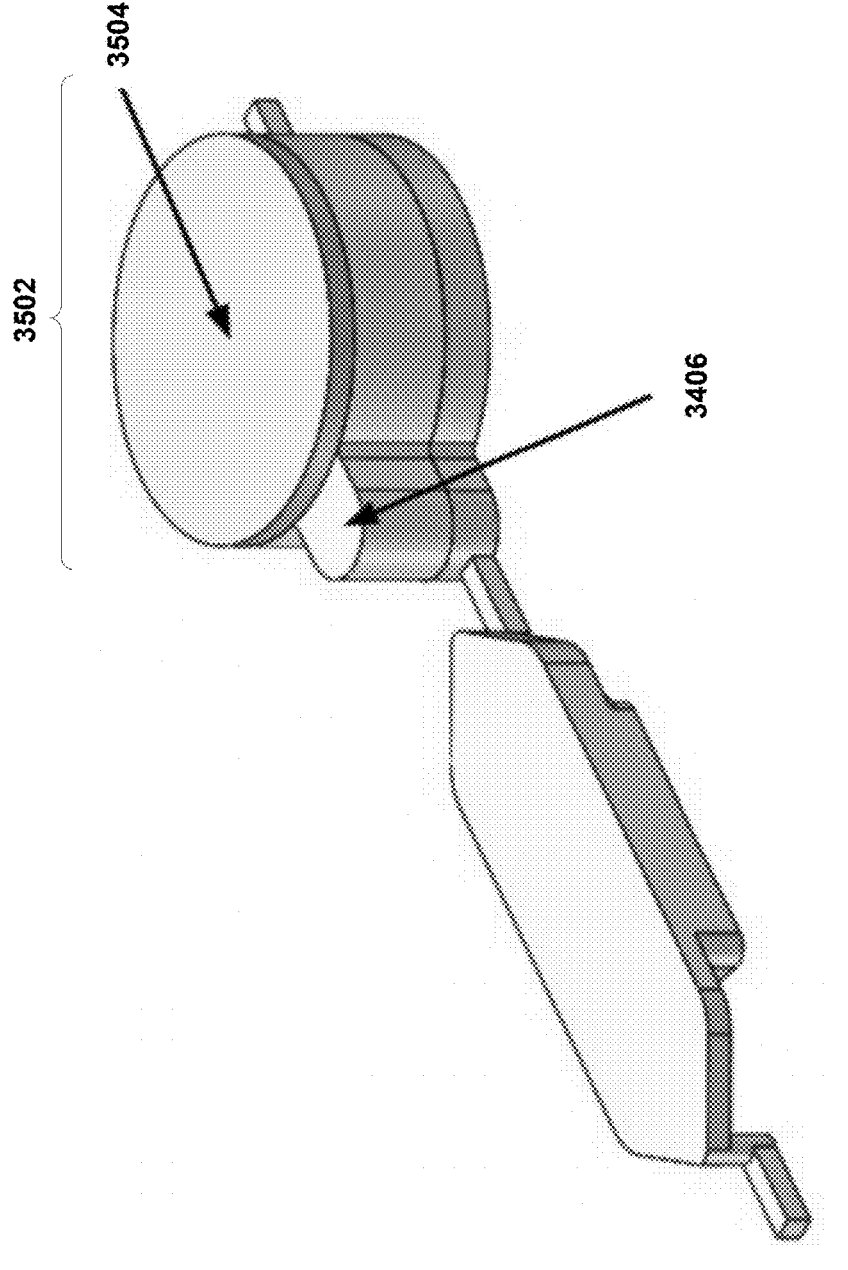
FIG. 35 shows a perspective view of a re-oxygenation chamber.

FIG. 35 shows a perspective view of a re-oxygenation chamber 3500. The re-oxygenation chamber 3500 has a circular chamber 3502 with an oxygen permeable membrane 3504, similar to re-oxygenation chambers previously described. The re-oxygenation chamber 3502 has a relatively larger volume (e.g., 0.52 mL) compared to chamber 900 of FIG. 9 (e.g., 0.4 mL). A port can be placed on the chamber 3500 in an extension 3406.

Figure 36A:
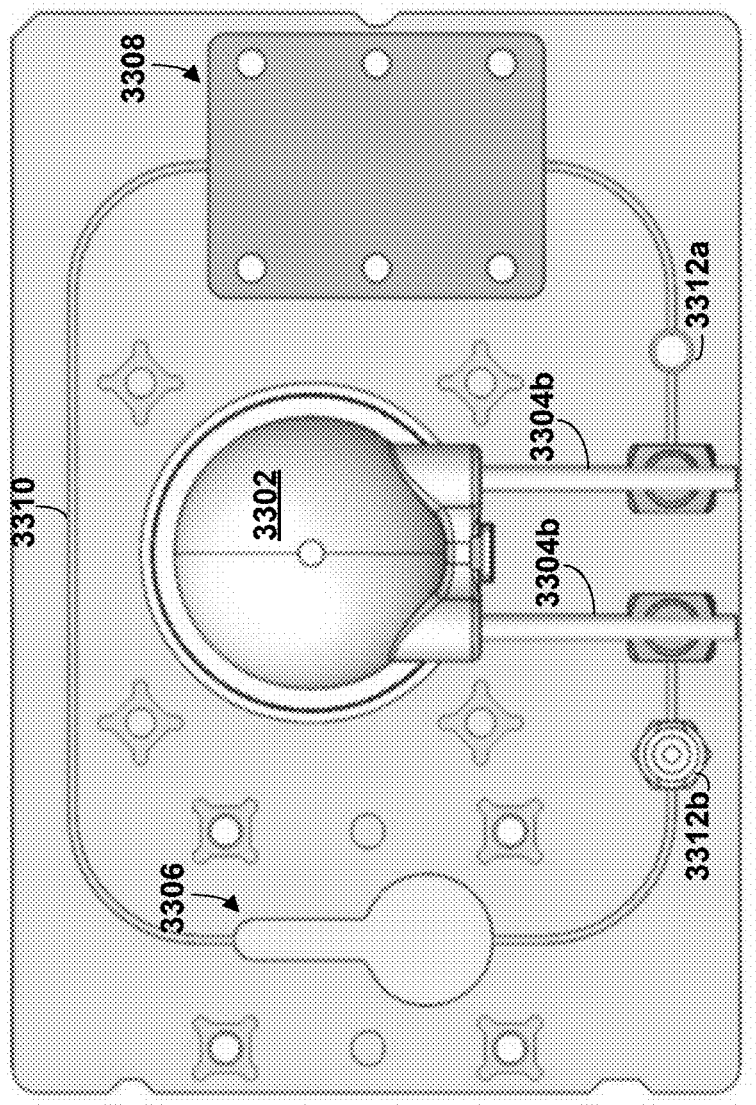
FIG. 36A shows a top view of the microfluidic chip of FIG. 33, including a peristaltic pump.
Figure 36B:
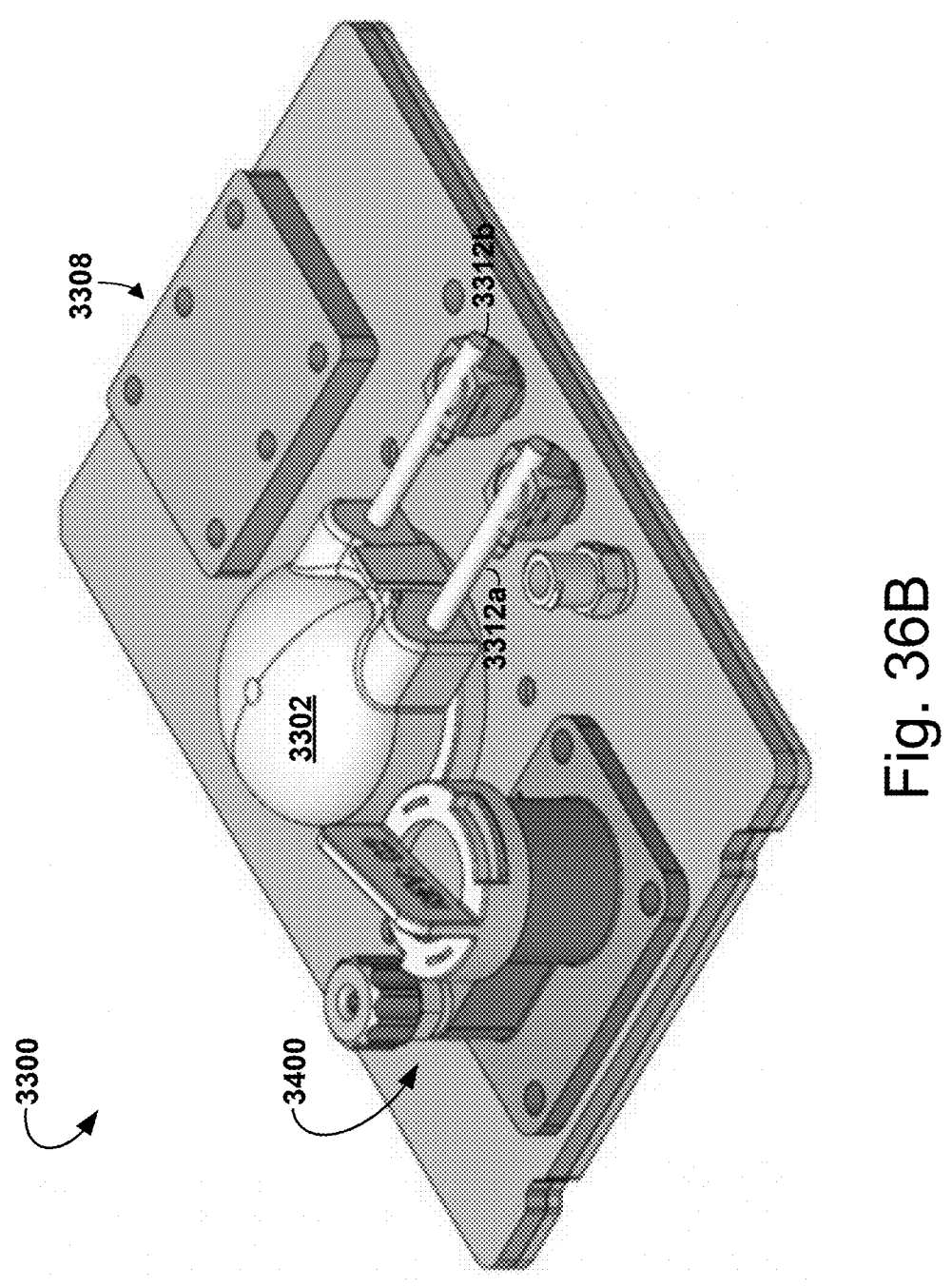
FIG. 36B shows a perspective view of the microfluidic chip of FIG. 33, including a peristaltic pump.

FIG. 36A shows a top view of the microfluidic chip 3300 of FIG. 33 including a peristaltic pump 3602. FIG. 36B shows a perspective view of the microfluidic chip 3300 of FIG. 33 including a peristaltic pump 3302. The re-oxygenation chamber cover 3400 is shown for covering the chamber 3306. In some implementations, a diaphragm pump is used instead of a peristaltic pump 3302.

Figure 37A:
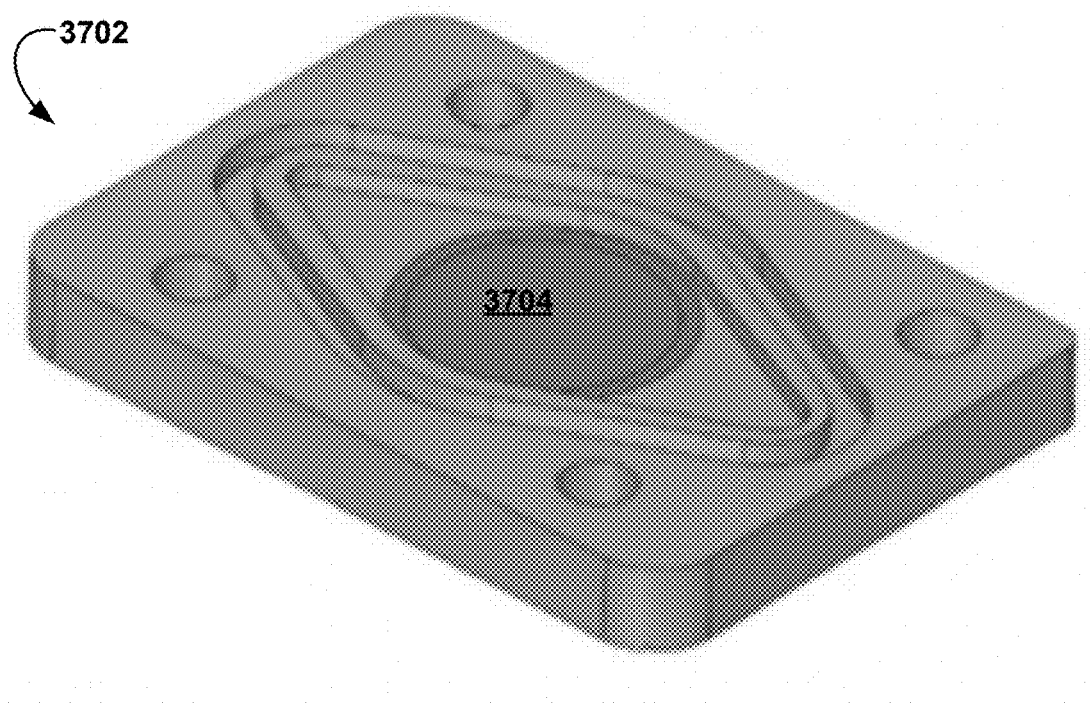
FIG. 37A shows a perspective view of a cover 3702 for a microfluidic chip insert 3700.
Figure 37A:
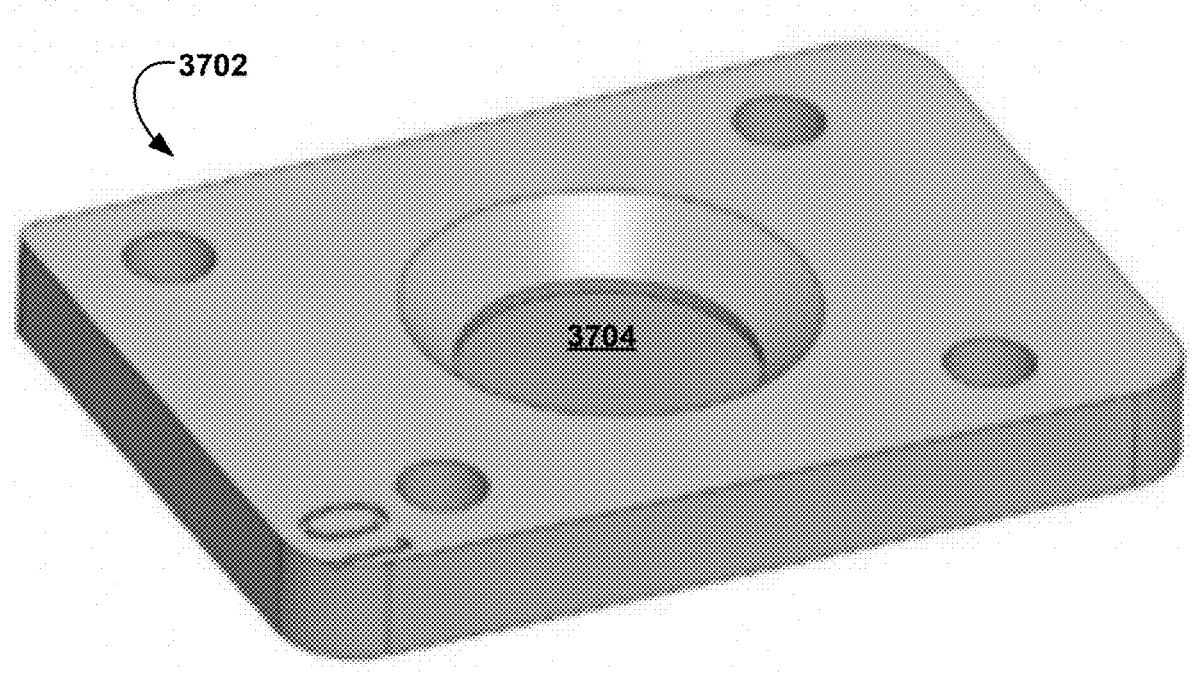
Figure 37B:
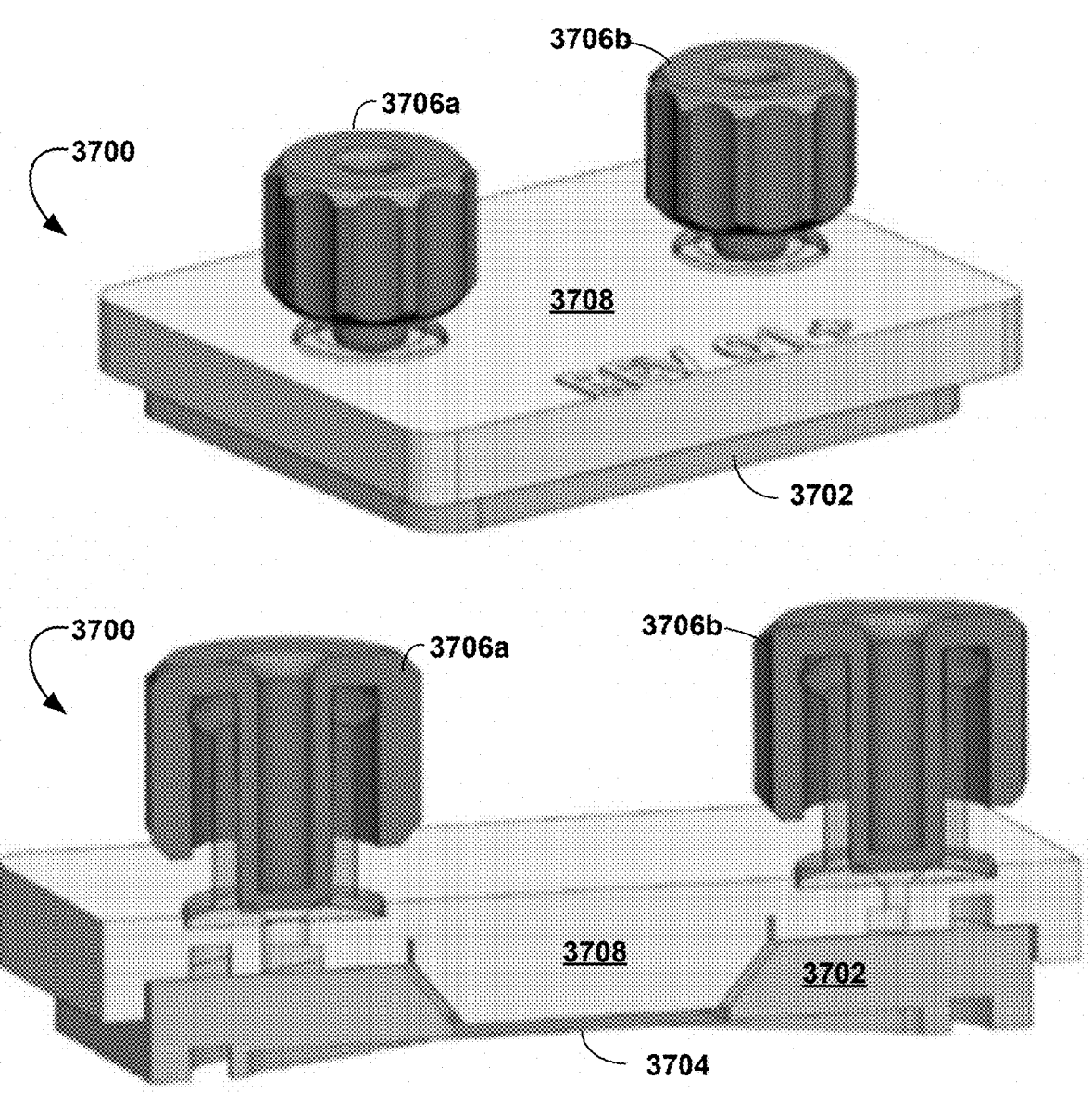
FIGS. 37B-C show cross-sections of an insert including the cover of FIG. 37A.
Figure 37C:
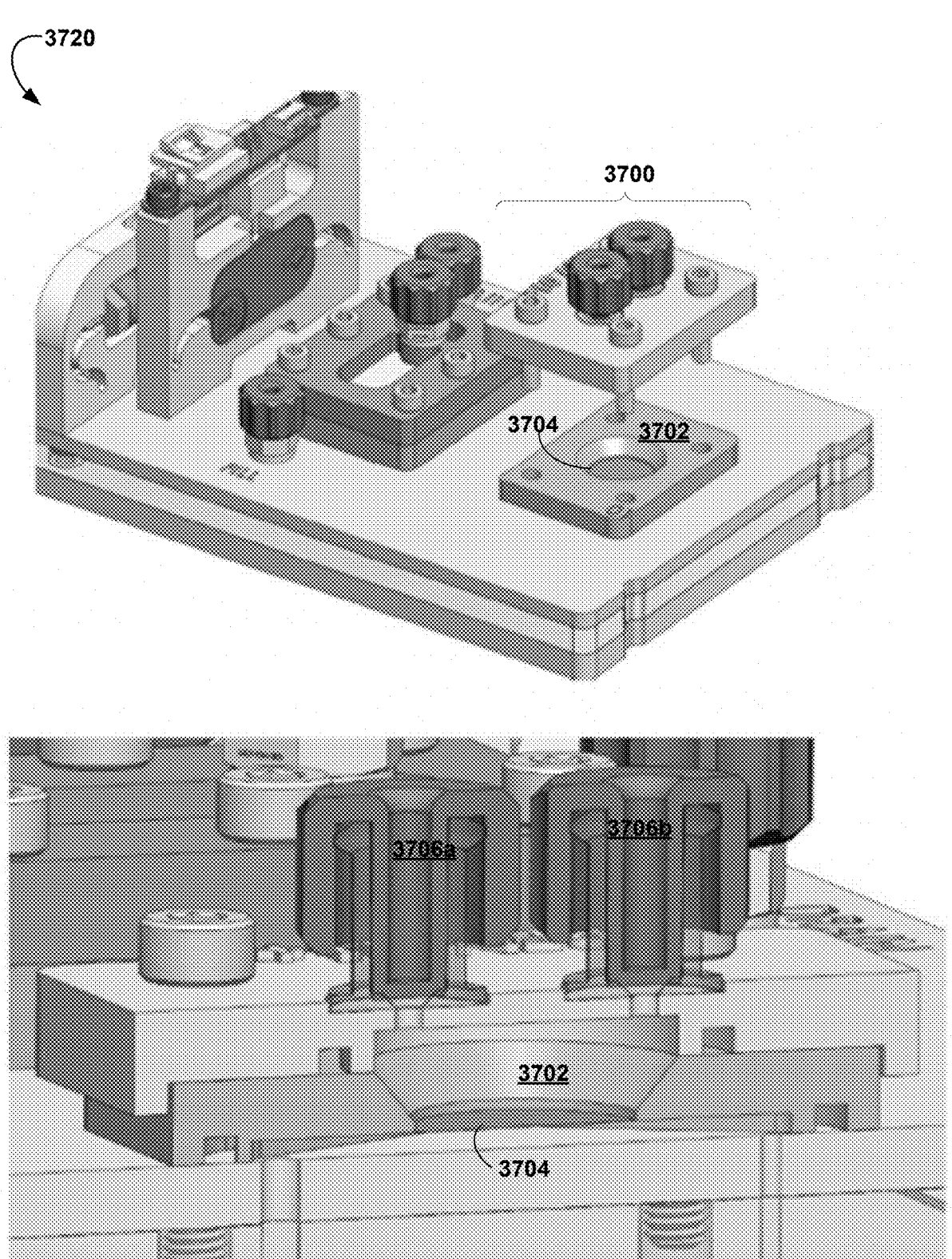

FIG. 37A shows a perspective view of a transwell frame 3702 for a microfluidic chip insert 3700. FIGS. 37B-C show cross-sections of an insert 3700 including the perfusion cover 3708 of FIG. 37A for a microfluidic chip 3720. The transwell frame 3702 supports a membrane 3704 configured to cover the cell chamber. Fasteners 3706*a-b* secure the perfusion cover 3708 to the transwell frame 3702. The membrane 3704 can be circular.

Figure 38B:
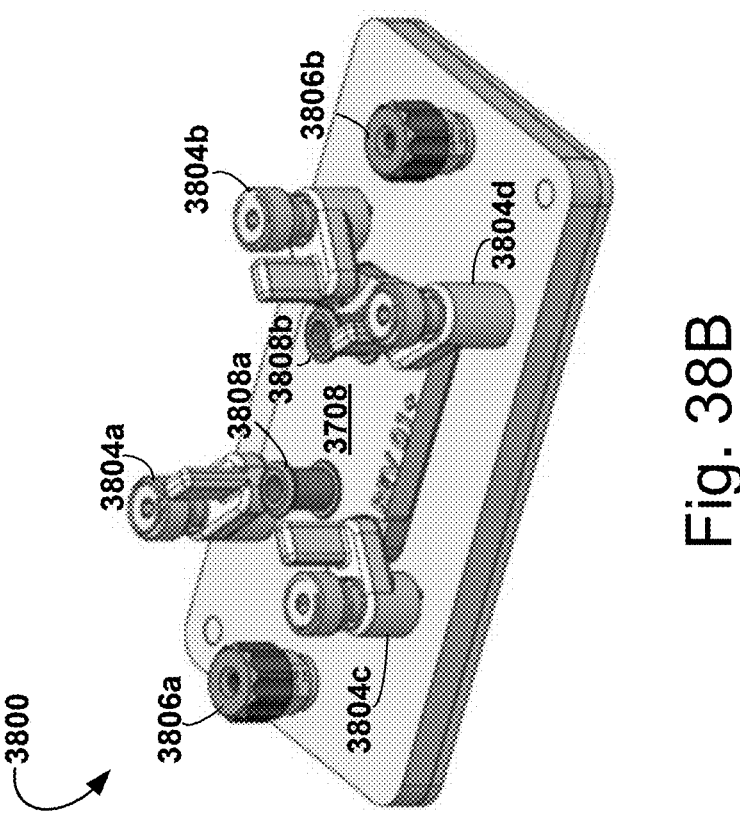
FIGS. 38A-B show views of a seeding insert for a microfluidic chip, such as the microfluidic chips described previously.
Figure 38A:
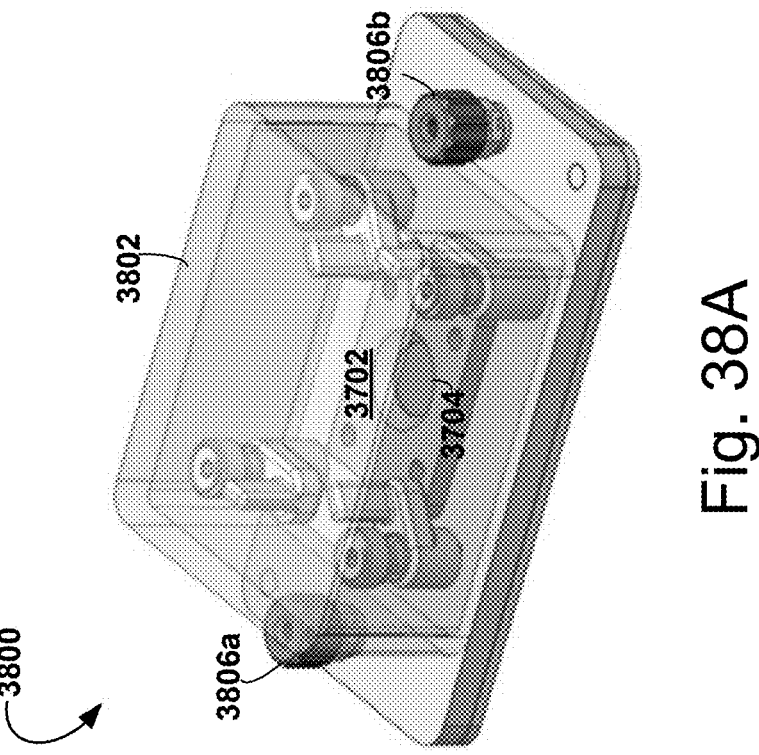

FIGS. 38A-B show views of a seeding insert 3800 for a microfluidic chip, such as the microfluidic chips described previously. The insert 3800 can be a multi-compartment insert, similar to those previously described (e.g., in relation to FIGS. 24A-26, and so forth). The insert 3800 is configured for seeding and maturation of tissue in the transwell frame 3702. Ports, such as Luer ports 3806*a-b*, provide access to a basal channel. The cover perfusion cover 3708 can be secured with clamps 3804*a* and 3804*d*, while the clamps 3804*b-c* can secure the transwell frame 3702. These clamps 3804*a-d* are movable to clamp the cover 3708 and frame 3702 in place or allow the cover to be removed (e.g., while seeding the tissue). A seeding cover 3802 can be placed over the open transwell frame 3702 during seeding. The cover 3802 can be clear to allow observation of the maturing tissue in the transwell frame 3702. Ports 3808*a-b*, which can include Luer ports, enable access to an apical channel of the insert 3800.

Generally, the insert 3800 enables tissue to mature on the insert relatively quickly. For example, epithelial and endothelial tissues can be matured on this chip faster with greater physiological result. Tubes are directly connected to ports 3806*a-b*, 3808*a-b* to perfuse the system. Perfusion can be driven by standard peristaltic pumps, diaphragm and other pumping systems. The insert 3800 can be configured for flow-through or recirculation operation. Recirculation saves the insert 3800 from wasting fluid media. Once the tissue matures, the insert 3800 can be transferred to one of the microfluidic chips described herein (e.g., single or multi-organ) for drug studies.

Figures 39A, 39B, 39C:
FIGS. 39A-C each show a perspective view of an example cell chamber geometry.

FIGS. 39A-C each show a perspective view of an example transwell frame geometry. FIG. 39A shows a transwell frame insert 3900*a* having an apical side 3902*a* and a basal side 3904*a*. In some implementations, the apical side 3902*a* has a volume of about 404 µL, and the basal side 3904*a* has a volume of about 212 µL. FIG. 39B shows a transwell frame insert having a second geometry. In some implementations, the apical side 3902*b* associated with transwell frame insert 3900*b* has a volume of about 160 µL, and the basal side (not shown) has a volume of about 212 µL. FIG. 39C shows a transwell frame insert having a second geometry. In some implementations, the chamber 3906 associated with transwell frame insert 3900*c* has an apical side has a volume of about 781 µL, and the basal side has a volume of about 212 µL. In some implementations, the transwell frame 3912 and perfusion cover 3910 of insert 3900*c* each has an altered geometry compared to the geometry of the transwell frame 3702 and cover 3708. These volumes are examples, and can be changed for different applications. In some implementations, the chambers 3902*a-b* and 3906 are configured to limit shear at high flow rates. For example, a 300 mL/hr flow rate can have an average shear stress of 1 dyne/cm². Generally, about 67% of the cell chamber area of the transwell chambers 390*a-b* are between 0.9-1.1 dyne/cm². Generally, about 17% of the cell chamber area has higher stresses than 1.1 dyne/cm². Generally, about 16% of the cell chamber area of the transwell chambers 3902*a-b* and 3906 have lower stresses than 0.9 dyne/cm².

Reference is made in detail to implementations, examples of which are illustrated in the accompanying drawings. In the previous description, numerous specific details are set forth in order to provide a thorough understanding of the various described implementations. However, it are apparent to one of ordinary skill in the art that the various described implementations may be practiced without these specific details. In other instances, well-known methods, procedures, components, circuits, and networks have not been described in detail so as not to unnecessarily obscure aspects of the implementations.

Several features are described that can each be used independently of one another or with any combination of other features. However, any individual feature may not address any of the problems discussed above or might only address one of the problems discussed above. Some of the problems discussed above might not be fully addressed by any of the features described in this specification. Although headings are provided, data related to a particular heading, but not found in the section having that heading, may also be found elsewhere in this description.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Software implementations of the described subject matter can be implemented as one or more computer programs. Each computer program can include one or more modules of computer program instructions encoded on a tangible, non-transitory, computer-readable computer-storage medium for execution by, or to control the operation of, data processing apparatus. Alternatively, or additionally, the program instructions can be encoded in/on an artificially generated propagated signal. For example, the signal can be a machine-generated electrical, optical, or electromagnetic signal that is generated to encode information for transmission to suitable receiver apparatus for execution by a data processing apparatus. The computer-storage medium can be a machine-readable storage device, a machine-readable storage substrate, a random or serial access memory device, or a combination of computer-storage mediums.

The terms "data processing apparatus," "computer," and "electronic computer device" (or equivalent as understood by one of ordinary skill in the art) refer to data processing hardware. For example, a data processing apparatus can encompass all kinds of apparatus, devices, and machines for processing data, including by way of example, a programmable processor, a computer, or multiple processors or computers. The apparatus can also include special purpose logic circuitry including, for example, a central processing unit (CPU), a field programmable gate array (FPGA), or an application specific integrated circuit (ASIC). In some implementations, the data processing apparatus or special purpose logic circuitry (or a combination of the data processing apparatus or special purpose logic circuitry) can be hardware- or software-based (or a combination of both hardware- and software-based). The apparatus can optionally include code that creates an execution environment for computer programs, for example, code that constitutes processor firmware, a protocol stack, a database management system, an operating system, or a combination of execution environments. The present disclosure contemplates the use of data processing apparatuses with or without conventional operating systems, for example, LINUX, UNIX, WINDOWS, MAC OS, ANDROID, or IOS.

A computer program, which can also be referred to or described as a program, software, a software application, a module, a software module, a script, or code, can be written in any form of programming language. Programming languages can include, for example, compiled languages, interpreted languages, declarative languages, or procedural languages. Programs can be deployed in any form, including as stand-alone programs, modules, components, subroutines, or units for use in a computing environment. A computer program can, but need not, correspond to a file in a file system. A program can be stored in a portion of a file that holds other programs or data, for example, one or more scripts stored in a markup language document, in a single file dedicated to the program in question, or in multiple coordinated files storing one or more modules, sub programs, or portions of code. A computer program can be deployed for execution on one computer or on multiple computers that are located, for example, at one site or distributed across multiple sites that are interconnected by a communication network. While portions of the programs illustrated in the various figures may be shown as individual modules that implement the various features and functionality through various objects, methods, or processes, the programs can instead include a number of sub-modules, third-party services, components, and libraries. Conversely, the features and functionality of various components can be combined into single components as appropriate. Thresholds used to make computational determinations can be statically, dynamically, or both statically and dynamically determined.

The methods, processes, or logic flows described in this specification can be performed by one or more programmable computers executing one or more computer programs to perform functions by operating on input data and generating output. The methods, processes, or logic flows can also be performed by, and apparatus can also be implemented as, special purpose logic circuitry, for example, a CPU, an FPGA, or an ASIC.

Computers suitable for the execution of a computer program can be based on one or more of general and special purpose microprocessors and other kinds of CPUs. The elements of a computer are a CPU for performing or executing instructions and one or more memory devices for storing instructions and data. Generally, a CPU can receive instructions and data from (and write data to) a memory. A computer can also include, or be operatively coupled to, one or more mass storage devices for storing data. In some implementations, a computer can receive data from, and transfer data to, the mass storage devices including, for example, magnetic, magneto optical disks, or optical disks. Moreover, a computer can be embedded in another device, for example, a mobile telephone, a personal digital assistant (PDA), a mobile audio or video player, a game console, a global positioning system (GPS) receiver, or a portable storage device such as a universal serial bus (USB) flash drive.

Computer readable media (transitory or non-transitory, as appropriate) suitable for storing computer program instructions and data can include all forms of permanent/non-permanent and volatile/non-volatile memory, media, and memory devices. Computer readable media can include, for example, semiconductor memory devices such as random access memory (RAM), read only memory (ROM), phase change memory (PRAM), static random access memory (SRAM), dynamic random access memory (DRAM), erasable programmable read-only memory (EPROM), electrically erasable programmable read-only memory (EEPROM), and flash memory devices. Computer readable media can also include, for example, magnetic devices such as tape, cartridges, cassettes, and internal/removable disks. Computer readable media can also include magneto optical disks and optical memory devices and technologies including, for example, digital video disc (DVD), CD ROM, DVD+/−R, DVD-RAM, DVD-ROM, HD-DVD, and BLU-RAY. The memory can store various objects or data, including caches, classes, frameworks, applications, modules, backup data, jobs, web pages, web page templates, data structures, database tables, repositories, and dynamic information. Types of objects and data stored in memory can include parameters, variables, algorithms, instructions, rules, constraints, and references. Additionally, the memory can include logs, policies, security or access data, and reporting files. The processor and the memory can be supplemented by, or incorporated in, special purpose logic circuitry.

Implementations of the subject matter described in the present disclosure can be implemented on a computer having a display device for providing interaction with a user, including displaying information to (and receiving input from) the user. Types of display devices can include, for example, a cathode ray tube (CRT), a liquid crystal display (LCD), a light-emitting diode (LED), and a plasma monitor. Display devices can include a keyboard and pointing devices including, for example, a mouse, a trackball, or a trackpad. User input can also be provided to the computer through the use of a touchscreen, such as a tablet computer surface with pressure sensitivity or a multi-touch screen using capacitive or electric sensing. Other kinds of devices can be used to provide for interaction with a user, including to receive user feedback including, for example, sensory feedback including visual feedback, auditory feedback, or tactile feedback. Input from the user can be received in the form of acoustic, speech, or tactile input. In addition, a computer can interact with a user by sending documents to, and receiving documents from, a device that is used by the user. For example, the computer can send web pages to a web browser on a user's client device in response to requests received from the web browser.

The term "graphical user interface," or "GUI," can be used in the singular or the plural to describe one or more graphical user interfaces and each of the displays of a particular graphical user interface. Therefore, a GUI can represent any graphical user interface, including, but not limited to, a web browser, a touch screen, or a command line interface (CLI) that processes information and efficiently presents the information results to the user. In general, a GUI can include a plurality of user interface (UI) elements, some or all associated with a web browser, such as interactive fields, pull-down lists, and buttons. These and other UI elements can be related to or represent the functions of the web browser.

Implementations of the subject matter described in this specification can be implemented in a computing system that includes a back end component (for example, as a data server), or that includes a middleware component (for example, an application server). Moreover, the computing system can include a front-end component, for example, a client computer having one or both of a graphical user interface or a Web browser through which a user can interact with the computer. The components of the system can be interconnected by any form or medium of wireline or wireless digital data communication (or a combination of data communication) in a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) (for example, using 802.11 a/b/g/n or 802.20 or a combination of protocols), all or a portion of the Internet, or any other communication system or systems at one or more locations (or a combination of communication networks). The network can communicate with, for example, Internet Protocol (IP) packets, frame relay frames, asynchronous transfer mode (ATM) cells, voice, video, data, or a combination of communication types between network addresses.

The computing system can include clients and servers. A client and server can generally be remote from each other and can typically interact through a communication network. The relationship of client and server can arise by virtue of computer programs running on the respective computers and having a client-server relationship.

Cluster file systems can be any file system type accessible from multiple servers for read and update. Locking or consistency tracking may not be necessary since the locking of exchange file system can be done at application layer. Furthermore, Unicode data files can be different from non-Unicode data files.

While this specification contains many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

In the foregoing description, embodiments of the invention have been described with reference to numerous specific details that may vary from implementation to implementation. The description and drawings are, accordingly, to be regarded in an illustrative rather than a restrictive sense. The sole and exclusive indicator of the scope of the invention, and what is intended by the applicants to be the scope of the invention, is the literal and equivalent scope of the set of claims that issue from this application, in the specific form in which such claims issue, including any subsequent correction. Any definitions expressly set forth herein for terms contained in such claims shall govern the meaning of such terms as used in the claims. In addition, when we use the term "further comprising" or "further including" in the foregoing description or following claims, what follows this phrase can be an additional step or entity, or a sub-step/sub-entity of a previously-recited step or entity.

Particular implementations of the subject matter have been described. Other implementations, alterations, and permutations of the described implementations are within the scope of the following claims as are apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations, and it should be understood that the described program components and systems can generally be integrated together in a single software product or packaged into multiple software products.

Accordingly, the previously described example implementations do not define or constrain the present disclosure. Other changes, substitutions, and alterations are also possible without departing from the spirit and scope of the present disclosure.

Furthermore, any claimed implementation is considered to be applicable to at least a computer-implemented method; a non-transitory, computer-readable medium storing computer-readable instructions to perform the computer-implemented method; and a computer system comprising a computer memory interoperably coupled with a hardware processor configured to perform the computer-implemented method or the instructions stored on the non-transitory, computer-readable medium.

A number of embodiments of these systems and methods have been described. Nevertheless, it are understood that various modifications may be made without departing from the spirit and scope of this disclosure.

What is claimed is:

1. A microfluidic chip, comprising:
a pump configured to pump a fluid media through a fluid circuit;
a cell chamber in the fluid circuit, the cell chamber supporting a plurality of cells, the cell chamber configured to receive the fluid media including oxygen for exposing the plurality of cells to the fluid media including the oxygen; and
a re-oxygenation chamber configured to add oxygen to the fluid media circulating in the fluid circuit,
wherein the cell chamber forms part of an insert that is removable from the re-oxygenation chamber and pump of the fluid circuit
wherein the cell chamber comprises a waterfall feature, the waterfall feature including a step from a first level of the cell chamber to a second level of the cell chamber.

2. The microfluidic chip of claim 1, further comprising:
a flow sensor configured to measure a flow rate of the fluid media in the fluid circuit; and
a controller in communication with the flow sensor and the pump, the controller configured to:
obtain data specifying a desired flow rate of the fluid media;
receive a signal specifying the flow rate measured by the flow sensor; and
generate, in response to receiving the signal specifying the flow rate, a pump control signal configured to cause the pump to pump the fluid media at the desired flow rate.

3. The microfluidic chip of claim 1, further comprising a valve, the valve being moveable to a first position that allows the fluid media to circulate in the fluid circuit through the cell chamber, and the valve being moveable to a second position that isolates the cell chamber from the fluid circuit to enable seeding of the cell chamber with the cells.

4. The microfluidic chip of claim 1, further comprising a sample carousel, the sample carousel comprising one or more sample chambers configured to store a portion of the fluid media.

5. The microfluidic chip of claim 1, wherein the re-oxygenation chamber comprises an oxygen permeable membrane for receiving oxygen from an environment outside of the fluid circuit.

6. The microfluidic chip of claim 1, further comprising a pH sensor configured to measure a pH of the fluid media.

7. The microfluidic chip of claim 1, wherein the fluid circuit comprises a resistive tubing configured to limit a flow rate in the fluid circuit.

8. The microfluidic chip of claim 1, further comprising:
 a first oxygen concentration sensor configured to measure oxygen concentration in the fluid media at an input of the cell chamber; and
 a second oxygen concentration sensor configured to measure the oxygen concentration in the fluid media at an output of the cell chamber.

9. The microfluidic chip of claim 1, further comprising an air inlet port configured to provide oxygen to the re-oxygenation chamber, and an air outlet port configured to remove air from the re-oxygenation chamber.

10. The microfluidic chip of claim 1, further comprising a second fluid circuit comprising a second cell chamber, the second fluid circuit configured to circulate second fluid media that is isolated from the fluid media of the fluid circuit.

11. The microfluidic chip of claim 1, further comprising a sampling port configured to enable removal of a portion of the fluid media from the fluid circuit.

12. The microfluidic chip of claim 1, wherein the cell chamber comprises a seed port for seeding the cell chamber and a waste port for removing waste cells from the cell chamber.

13. The microfluidic chip of claim 1, wherein the step is 2-3 mm in height.

14. The microfluidic chip of claim 1, wherein the insert includes a platform for perfusion of cells, for seeding cells, or both.

15. The microfluidic chip of claim 14, wherein the platform includes a permeable membrane configured to allow the fluid media to pass through and supports the plurality of cells.

16. The microfluidic chip of claim 1, wherein the insert includes a top cover configured to be coupled to a top of a substrate to seal the cell chamber.

17. The microfluidic chip of claim 1, wherein the insert includes a bottom cover configured to be coupled to a bottom layer to seal the cell chamber, the bottom cover including the cell chamber.

18. The microfluidic chip of claim 1, wherein the cell chamber includes a single compartment.

19. The microfluidic chip of claim 1, wherein the cell chamber includes a dual-compartment configuration including an apical side and a basal side.

20. The microfluidic chip of claim 1, wherein the cell chamber is a first cell chamber, the microfluidic chip further comprising a second cell chamber configured to receive the fluid media in sequence with the first cell chamber.

21. The microfluidic chip of claim 1, further comprising a transwell adapter for interfacing the cell chamber with a transwell.

22. The microfluidic chip of claim 1, wherein the cell chamber is part of an insert that is configured for seeding the plurality of cells, the microfluidic chip further comprising:
 one or more clamps configured to secure the insert; and
 a seeding cover configured to cover the insert.

23. The microfluidic chip of claim 1, further comprising a port for removal of the fluid media, the port comprising a valve enabling complete removal of fluid media from the fluid circuit.

24. A support module, comprising:
 a controller; and
 a platform configured to receive the microfluidic chip of any of claims 1-12, the platform configured to couple the microfluidic chip to the controller for communicating data between the controller and the pump of the microfluidic chip.

25. The support module of claim 24, further comprising a user interface configured to enable a user to input control parameters for controlling operation of the microfluidic chip, the control parameters comprising one or more of a pump speed, an oxygen concentration in the cell chamber, and a pump speed of the pump.

26. The support module of claim 24, further comprising a memory port configured to receive a memory device, the memory configured to store one or more configuration parameters for operation of the microfluidic chip and data received from the microfluidic chip.

27. The support module of claim 24, wherein the controller is configured to:
 receive identifier data from the microfluidic chip;
 obtain one or more control parameters that are associated with the identifier; and
 automatically control operation of the microfluidic chip in accordance with the one or more control parameters.

28. The support module of claim 24, wherein the controller is configured to control operation of a plurality of instances of the microfluidic chip in parallel.

29. The support module of claim 24, further comprising a mechanical device configured to interface with a sampling carousel on the microfluidic chip, wherein the mechanical device is configured to control a position of the sampling carousel during operation of the microfluidic chip.

30. The support module of claim 24, further comprising:
 a port configured to interface a sensor with the microfluidic chip for detecting at least one of an oxygen level in the fluid media, a pH of the fluid media, or both.

* * * * *